US011725247B2

(12) United States Patent
Frampton et al.

(10) Patent No.: US 11,725,247 B2
(45) Date of Patent: Aug. 15, 2023

(54) METHODS OF TREATING CANCER

(71) Applicants: FOUNDATION MEDICINE, INC., Cambridge, MA (US); VANDERBILT UNIVERSITY, Nashville, TN (US)

(72) Inventors: Garrett Michael Frampton, Somerville, MA (US); Roman Yelensky, Newton, MA (US); James Xin Sun, Newton, MA (US); Douglas Buckner Johnson, Nashville, TN (US); Christine Marie Lovly, Nashville, TN (US); Jeffrey Alan Sosman, Brentwood, TN (US); David Fabrizio, Cambridge, MA (US); Philip James Stephens, Lexington, MA (US); Vincent A. Miller, West Orange, NJ (US)

(73) Assignees: FOUNDATION MEDICINE, INC., Cambridge, MA (US); VANDERBILT UNIVERSITY, Nashville, TN (US)

( * ) Notice: Subject to any disclaimer, the term of this patent is extended or adjusted under 35 U.S.C. 154(b) by 1210 days.

(21) Appl. No.: 16/080,421

(22) PCT Filed: Feb. 27, 2017

(86) PCT No.: PCT/US2017/019733
§ 371 (c)(1),
(2) Date: Aug. 28, 2018

(87) PCT Pub. No.: WO2017/151517
PCT Pub. Date: Sep. 8, 2017

(65) Prior Publication Data
US 2019/0085403 A1    Mar. 21, 2019

Related U.S. Application Data

(60) Provisional application No. 62/301,510, filed on Feb. 29, 2016.

(51) Int. Cl.
| | |
|---|---|
| C12Q 1/6886 | (2018.01) |
| C07K 16/28 | (2006.01) |
| G16H 50/30 | (2018.01) |
| G16H 50/20 | (2018.01) |
| A61P 35/00 | (2006.01) |
| G16B 20/00 | (2019.01) |
| G06F 17/15 | (2006.01) |
| A61K 39/00 | (2006.01) |

(52) U.S. Cl.
CPC ............ *C12Q 1/6886* (2013.01); *A61P 35/00* (2018.01); *C07K 16/2818* (2013.01); *G06F 17/15* (2013.01); *G16B 20/00* (2019.02); *G16H 50/20* (2018.01); *G16H 50/30* (2018.01); *A61K 2039/505* (2013.01); *C12Q 2600/106* (2013.01); *C12Q 2600/156* (2013.01)

(58) Field of Classification Search
CPC ...... C12Q 1/6886; G16H 50/30; G16H 50/20; A61P 35/00; G16B 20/00; C07K 16/2818; G06F 17/15
See application file for complete search history.

(56) References Cited

U.S. PATENT DOCUMENTS

| | | | |
|---|---|---|---|
| 4,366,241 A | 12/1982 | Tom et al. | |
| 4,376,110 A | 3/1983 | David et al. | |
| 4,517,288 A | 5/1985 | Giegel et al. | |
| 4,816,567 A | 3/1989 | Cabilly et al. | |
| 4,837,168 A | 6/1989 | de Jaeger et al. | |
| 4,987,071 A | 1/1991 | Cech et al. | |
| 5,093,246 A | 3/1992 | Cech et al. | |
| 5,116,742 A | 5/1992 | Cech et al. | |
| 5,223,409 A | 6/1993 | Ladner et al. | |
| 5,225,539 A | 7/1993 | Winter | |
| 5,491,224 A | 2/1996 | Bittner et al. | |
| 5,547,835 A | 8/1996 | Koster | |
| 5,585,089 A | 12/1996 | Queen et al. | |
| 5,605,798 A | 2/1997 | Koster | |
| 5,693,761 A | 12/1997 | Queen et al. | |
| 5,693,762 A | 12/1997 | Queen et al. | |
| 6,277,569 B1 | 8/2001 | Bittner et al. | |
| 6,455,258 B2 | 9/2002 | Bastian et al. | |
| 7,943,743 B2 | 5/2011 | Korman et al. | |
| 8,008,449 B2 | 8/2011 | Korman et al. | |
| 8,354,509 B2 † | 1/2013 | Carven | |
| 8,609,089 B2 | 12/2013 | Langermann et al. | |
| 11,066,709 B2 | 7/2021 | Klijn et al. | |
| 11,279,767 B2 | 3/2022 | Bourgon et al. | |
| 11,300,570 B2 | 4/2022 | Fabrizio et al. | |
| 2003/0143204 A1 | 7/2003 | Lewis et al. | |

(Continued)

FOREIGN PATENT DOCUMENTS

| | | |
|---|---|---|
| CN | 105209919 A | 12/2015 |
| EP | 519596 B1 | 2/2005 |

(Continued)

OTHER PUBLICATIONS

Rizvi et al ("Mutational Landscape Determines Sensitivity to PD-1 Blockade in Non-Small Cell Lung Cancer" Cancer Immunology (2015) vol. 348(6230), pp. 124-128 (Year: 2015).*
International Search Report and Written Opinion received in International Application No. PCT/US2017/019733, dated Aug. 11, 2017.
Albertson (1984). "Localization of the ribosomal genes in Caenorhabditis elegans chromosomes by in situ hybridization using biotin-labeled probes," The EMBO Journal. 3:1227-1234.

(Continued)

*Primary Examiner* — Jerry Lin
(74) *Attorney, Agent, or Firm* — Morrison & Foerster LLP

(57) ABSTRACT

Methods and compositions for treating cancer such as melanomas are disclosed.

16 Claims, 16 Drawing Sheets
Specification includes a Sequence Listing.

(56) References Cited

U.S. PATENT DOCUMENTS

| | | |
|---|---|---|
| 2003/0166282 A1 | 9/2003 | Brown et al. |
| 2003/0224432 A1 | 12/2003 | Myers et al. |
| 2004/0038278 A1 | 2/2004 | Tzertzinis et al. |
| 2004/0086884 A1 | 5/2004 | Beach et al. |
| 2010/0028330 A1 | 2/2010 | Collins et al. |
| 2010/0029498 A1 | 2/2010 | Gnirke et al. |
| 2012/0039906 A1 | 2/2012 | Olive |
| 2012/0114649 A1 | 5/2012 | Langermann et al. |
| 2012/0208706 A1 | 8/2012 | Downing et al. |
| 2013/0309254 A1 | 11/2013 | Samuels et al. |
| 2014/0287937 A1 | 9/2014 | So et al. |
| 2014/0296081 A1 | 10/2014 | Diehn et al. |
| 2014/0336996 A1 | 11/2014 | Sun et al. |
| 2016/0009805 A1 | 1/2016 | Kowanetz et al. |
| 2017/0175197 A1 | 6/2017 | Gatalica et al. |
| 2017/0275689 A1 | 9/2017 | Maguire et al. |
| 2018/0045727 A1 | 2/2018 | Spetzler et al. |
| 2018/0231554 A1 | 8/2018 | Schatton et al. |
| 2018/0282417 A1 | 10/2018 | Higgs et al. |
| 2018/0291074 A1 | 10/2018 | Chan et al. |
| 2018/0363066 A1 | 12/2018 | Chalmers et al. |
| 2018/0371099 A1 | 12/2018 | Bourgon et al. |
| 2019/0025308 A1 | 1/2019 | Cummings et al. |
| 2019/0218618 A1 | 7/2019 | Klijn et al. |
| 2019/0219586 A1 | 7/2019 | Fabrizio et al. |
| 2022/0056531 A1 | 2/2022 | Trabucco et al. |
| 2022/0090205 A1 | 3/2022 | Klijn et al. |
| 2022/0153861 A1 | 5/2022 | Bourgon et al. |
| 2022/0412981 A1 | 12/2022 | Fabrizio et al. |

FOREIGN PATENT DOCUMENTS

| | | |
|---|---|---|
| EP | 430402 B2 | 3/2008 |
| JP | 2016520800 A | 7/2016 |
| JP | 2017537087 A | 12/2017 |
| JP | 2018502828 A | 2/2018 |
| JP | 2019535237 A | 12/2019 |
| WO | WO-1986001533 A1 | 3/1986 |
| WO | WO-1987002671 A1 | 5/1987 |
| WO | WO-1988009810 A1 | 12/1988 |
| WO | WO-1989010134 A1 | 11/1989 |
| WO | WO-1990002809 A1 | 3/1990 |
| WO | WO-1991000906 A1 | 1/1991 |
| WO | WO-1991010741 A1 | 7/1991 |
| WO | WO-1991017271 A1 | 11/1991 |
| WO | WO-1992001047 A1 | 1/1992 |
| WO | WO-1992003917 A1 | 3/1992 |
| WO | WO-1992003918 A1 | 3/1992 |
| WO | WO-1992009690 A2 | 6/1992 |
| WO | WO-1992015679 A1 | 9/1992 |
| WO | WO-1992018619 A1 | 10/1992 |
| WO | WO-1992020791 A1 | 11/1992 |
| WO | WO-1993001288 A1 | 1/1993 |
| WO | WO-1994016101 A2 | 7/1994 |
| WO | WO-1994021822 A1 | 9/1994 |
| WO | WO-1996029431 A2 | 11/1996 |
| WO | WO-2006121168 A1 | 11/2006 |
| WO | WO-2007005874 A2 | 1/2007 |
| WO | WO-2009101611 A1 | 8/2009 |
| WO | WO-2009114335 A2 | 9/2009 |
| WO | WO-2010077634 A1 | 7/2010 |
| WO | WO-2012092426 A1 | 7/2012 |
| WO | WO-2013070634 A1 | 5/2013 |
| WO | WO-2014151006 A2 | 9/2014 |
| WO | WO-2014183078 A1 | 11/2014 |
| WO | WO-2015095423 A2 | 6/2015 |
| WO | 2015103037 A2 | 7/2015 |
| WO | WO-2015116868 A2 | 8/2015 |
| WO | WO-2015164862 A1 | 10/2015 |
| WO | WO-2016018481 A2 | 2/2016 |
| WO | WO-2016077553 A1 | 5/2016 |
| WO | WO-2016081947 A2 | 5/2016 |
| WO | WO-2016089873 A1 | 6/2016 |
| WO | WO-2017151502 A1 | 9/2017 |
| WO | WO-2017151517 A1 | 9/2017 |
| WO | WO-2017151524 A1 | 9/2017 |
| WO | WO-2018068028 A1 | 4/2018 |
| WO | WO-2019018757 A1 | 1/2019 |

OTHER PUBLICATIONS

Andersen et al., (1993). "A conserved alternative splice in the von Recklinghausen neurofibromatosis (NF1) gene produces two neurofibromin isoforms, both of which have GTPase-activating protein activity," Molecular and Cellular Biology, 13(1):487-495.

Ars, et al., (2000). "Mutations affecting mRNA splicing are the most common molecular defects in patients with neurofibromatosis type 1," Human Molecular Genetics, 9(2):237-247.

Bahary et al., (2017). "Genomic profiling of circulating tumor DNA (ctDNA) from patients (pts) with pancreatic ductal adenocarcinoma (PDA)," J Clin Oncol., 35(15):4128. Abstract Only.

Balch et al., (2009). "Final Version of 2009 AJCC Melanoma Staging and Classification," Journal of Clinical Oncology, 27(36):6199-6206.

Barbas et al., (1991). "Assembly of combinatorial antibody libraries on phage surfaces: the gene III site," PNAS, 88(18):7978-7982.

Bardoli et al., (2016). "The PD-1/PD-L 1 axis in the pathogenesis of urothelial bladder cancer and evaluating its potential as a therapeutic target," Future Oncol., 12(5):595-600.

Barringer et al., (1990). "Blunt-end and single-strand ligations by *Escherichia coli* ligase: influence on an in vitro amplification scheme," Gene, 89(1):117-122.

Bartel et al., (1993). "Isolation of New Ribozymes from a Large Pool of Random Sequences," Science, 261(5127):1411-1418.

Beidler et al., (1988). "Cloning and high level expression of a chimeric antibody with specificity for human carcinoembryonic antigen," The Journal of Immunology, 141(11):4053-4060.

Ben-Salem et al., (2014). "The mutational spectrum of the NF1 gene in neurofibromatosis type I patients from UAE," Child's Nervous System, 30:1183-1189.

Bernards et al., (1992). "Complete Human NF1 cDNA Sequence: Two Alternatively Spliced mRNAs and Absence of Expression in a Neuroblastoma Line," DNA and Cell Biology, 11(10):727-734.

Bertola et al., (2005). "Neurofibromatosis-Noonan syndrome: Molecular evidence of the concurrence of both disorders in a patient," American Journal of Medical Genetics, 136A(3):242-245.

Bettegowda et al., (2014). "Detection of Circulating Tumor DNA in Early- and Late-Stage Human Malignancies," Sci Transl Med., 6(224):224ra24, 25 pages.

Better et al., (1988). "*Escherichia coli* Secretion of an Active Chimeric Antibody Fragment," Science, 240(4855):1041-1043.

Bidnur et al., (2016). "Inhibiting Immune Checkpoints for the Treatment of Bladder Cancer," Bladder Cancer, 2(1):15-25.

Billy et al., (2001). "Specific interference with gene expression induced by long, double-stranded RNA in mouse embryonal teratocarcinoma cell lines," PNAS, 98(25):14428-14433.

Boulandet et al., (2000). "NF1 gene analysis focused on CpG-rich exons in a cohort of 93 patients with neurofibromatosis type 1," Human Mutation, 16(3):274-275, 7 pages.

Breslow, (1970). "Thickness, cross-sectional areas and depth of invasion in the prognosis of cutaneous melanoma," Annals of Surgery, 172(5):902-908.

Bruggeman et al., (1991). "Human antibody production in transgenic mice: expression from 100 kb of the human IgH locus," European Journal of Immunology, 21(5):1323-1326.

Bruggeman et al., (1993). "Designer mice: the production of human antibody repertoires in transgenic animals," The Year in Immunology, 7:33-40.

Butler et al., (2008). "ALLPATHS: De novo assembly of whole-genome shotgun microreads," Genome Research, 18:810-820.

Cancer Genome Atlas Network, (2015). "Genomic Classification of Cutaneous Melanoma," Cell, 161(7):1681-1696.

Cancer Genome Atlas Research Network, (2014). "Comprehensive molecular characterization or urothelial bladder carcinoma," Nature, 507:315-22.

(56) References Cited

OTHER PUBLICATIONS

Carell et al., (1994). "A Novel Procedure for the Synthesis of Libraries Containing Small Organic Molecules," Angewandte Chemie International Edition in English, 33(20):2059-2061.
Carell et al., (1994). "A Solution-Phase Screening Procedure for the Isolation of Active Compounds from a Library of Molecules," Angewandte Chemie International Edition in English, 33(20):2061-2064.
Caris Life Sciences, (2016). "Total Mutational Load—Immune Checkpoint Inhibitors Response," Available online at <https://www.carismolecularintelligence.com/wp-content/uploads/2016/12/TN0291-v1_ Total-Mutational-Load-Immunotherapy-REVERSED-PAGES.pdf>, 2 pages.
Casey et al., (2016). "MYC regulates the antitumor immune response through CD47 and PD-L1," Science, 352(6282):227-231.
Castro et al., (2015). "Mismatch repair deficiency associate with complete remission to combination programmed cell death ligan immune therapy in a patient with sporadic urothelial carcinoma: immunotheranostic considerations," J ImmunoTher Cancer, 3:58.
Cawthon et al., (1990). "A major segment of the neurofibromatosis type 1 gene: cDNA sequence, genomic structure, and point mutations," Cell, 62(1):193-201.
Cazier et al., (2014). "Whole-genome sequencing of bladder cancers reveals somatic CDKN1 A mutations and clinicopathological associations with mutation burden," Nat Commun, 5:4809.
Chalmers et al., (2017). "Analysis of 100,000 human cancer genomes reveals the landscape of tumor mutational burden," Genome Med., 9(1):34, 14 pages.
Champiat et al., (2014). "Exomics and immunogenics," Oncolmmunology, 3(1):e27817.
Cho et al., (1993). "An Unnatural Biopolymer," Science, 261 (5126):1303-1305, 3 pages.
Choudhury et al., (2015). "Low T-cell Receptor Diversity, High Somatic Mutation Burden, and High Neoantigen Load as Predictors of Clinical Outcome in Muscle-invasive Bladder Cancer," Eur Urol Focus, 2(4):445-452.
Clackson et al., (1991). "Making antibody fragments using phage display libraries," Nature, 352:624-628.
Clemens et al., (2000). "Use of double-stranded RNA interference in *Drosophila* cell lines to dissect signal transduction pathways," PNAS, 97(12):6499-6503.
Cohen et al., (1996). "Emerging Technologies for Sequencing Antisense Oligonucleotides: Capillary Electrophoresis and Mass Spectrometry," Advances in Chromatography, 1:127-162.
Communication pursuant to Rule 114(2) EPC for European Patent Application No. 17797468.0, dated Jul. 8, 2021 (10 pages).
Communication pursuant to Rule 114(2) EPC for European Patent Application No. 18750078.0, dated Jul. 19, 2021 (10 pages).
Cronin et al., (2004). "Measurement of Gene Expression in Archival Paraffin-Embedded Tissues: Development and Performance of a 92-Gene Reverse Transcriptase-Polymerase Chain Reaction Assay," The American Journal of Pathology, 164(1):35-42.
Cull et al., (1992). "Screening for receptor ligands using large libraries of peptides linked to the C terminus of the lac repressor," PNAS 89(5):1865-1869.
Cwirla et al., (1990). "Peptides on phage: a vast library of peptides for identifying ligands," PNAS, 87(16):6378-6382.
Dagogo-Jack et al., (2017). "Genomic profiling of circulating tumor DNA (ctDNA) from patients (pts) with B advanced non-small cell lung cancer (NSCLC)," J Clin Oncol, 35(15 suppl):9025, 3 pages.
De Luca et al., (2003). "NF1 gene analysis based on DHPLC," Human Mutation, 21(2):171-172.
De Luca et al., (2004). "Novel and recurrent mutations in the NF1 gene in Italian patients with neurofibromatosis type 1," Human Mutation, 23(6):629.
De Luca et al., (2005). "NF1 Gene Mutations Represent the Major Molecular Event Underlying Neurofibromatosis-Noonan Syndrome," The American Journal of Human Genetics, 77(6):1092-1101.

Devlin et al., (1990). "Random Peptide Libraries: a Source of Specific Protein Binding Molecules," Science, 249(4967):404-406.
DeWitt et al., (1993). "'Diversomers': an approach to nonpeptide, nonoligomeric chemical diversity," PNAS, 90(15):6909-6913.
Diaz et al., (2014). "Liquid Biopsies: Genotyping Circulating Tumor DNA," J Clin Oncol, 32(6):579-586.
Eisenhauer et al., (2009). "New response evaluation criteria in solid tumours: Revised RECIST guideline (version 1.1)," European Journal of Cancer, 45(2):228-247.
Elbashir et al., (2001). "Duplexes of 21-nucleotide RNAs mediate RNA interference in cultured mammalian cells," Nature, 411:494-498.
Erb et al., (1994). "Recursive deconvolution of combinatorial chemical libraries," PNAS, 91(24):11422-11426.
Extended European Search Report for European Patent Application No. 17760558.1, dated Oct. 15, 2019 (16 pages).
Extended European Search Report issued in European Application No. 17760555.7, dated Oct. 4, 2019, 8 pages.
Fabbri et al., (2011). "Analysis of the chronic lymphocytic leukemia coding genome: role of NOTCH1 mutational activation," Journal Of Experimental Medicine, 208(7):1389-1401.
Fahsold et al., (2000). "Minor lesion mutational spectrum of the entire NF1 gene does not explain its high mutability but points to a functional domain upstream of the GAP-related domain," The American Journal of Human Genetics, 66(3):790-818.
Fakhrejahani et al., (2015). "Immunotherapies for bladder cancer: a new hope," Curr Opin Urol., 25(6):586-596.
Faria et al., (2001). "Phosphoramidate oligonucleotides as potent antisense molecules in cells and in vivo," Nature Biotechnology, 19:40-44.
Felici et al., (1991). "Selection of antibody ligands from a large library of oligopeptides expressed on a multivalent exposition vector," Journal of Molecular Biology, 222(2):301-310.
Ferner et al., (2004). "Neurofibromatous neuropathy in neurofibromatosis 1 (NF1)," Journal of Medical Genetics, 41: 837-841.
Finger et al., (1997). "The human PD-1 gene: complete cDNA, genomic organization, and developmentally regulated expression in B cell progenitors," Gene, 197(1-2):177-87.
Fodor et al., (1993). "Multiplexed biochemical assays with biological chips," Nature, 364:555-556.
Forbes et al., (2014). "COSMIC: exploring the world's knowledge of somatic mutations in human cancer," Nucleic Acids Research, 43(D1):D805-D811.
FoundationOne, (2018). "Technical Information and Test Overview," Available online at <https://assets.contentful.com/vhribv12lmne/6YRrchSINOeSu48YwuesoY/caeec492925a7d569ce4e070866f709b/F1_-_Tech Specs.pdf>, 2 pages.
Frampton et al., (2013). "Development and validation of a clinical cancer genomic profiling test based on massively parallel DNA sequencing," Nature Biotechnology, 31(11):1023-1031.
Frampton et al., (2015). "Assessment of tumor mutation burden from >60,000 clinical cancer patients using comprehensive genomic profiling," J Clin Oncol., 34(15 suppl):11558, 3 pages.
Francisco et al., "Melanoma Genetics: From Susceptibility to Progression," in Melanoma—From Early Detection to Treatment (2016) InTech Publications, Chapter 4, pp. 83-136.
Fuchs et al., (1991). "Targeting Recombinant Antibodies to the Surface of *Escherichia coli*: Fusion to a Peptidoglycan Associated Lipoprotein," Bio/Technology, 9:1369-1372.
Gallop et al., (1994). "Applications of Combinatorial Technologies to Drug Discovery. 1. Background and Peptide Combinatorial Libraries," Journal of Medicinal Chemistry, 37(9):1233-1251.
Gandara et al., (2018). "Blood-based tumor mutational burden as a predictor of clinical benefit in nonsmall-cell lung cancer patients treated with atezolizumab," Nat Med., 24(9):1441-8.
Garon et al., (2015). "Pembrolizumab for the Treatment of Non-Small-Cell Lung Cancer," The New England Journal of Medicine, 372:2018-2028.
Garrard et al., (1991). "FAB Assembly and Enrichment in a Monovalent Phage Display System," Bio/Technology, 9:1373-1377.

(56) References Cited

OTHER PUBLICATIONS

Gasparini et al., (1996). "Scanning the first part of the neurofibromatosis type 1 gene by RNA-SSCP: Identification of three novel mutations and of two new polymorphisms," Human Genetics, 97: 492-495.
Gatalica et al., (2014). "Programmed Cell Death 1 (PD-1) and Its Ligand (PD-L 1) in Common Cancers and Their Correlation with Molecular Cancer Type," Cancer Epidemiol Biomarkers Prev, 23(12):2965-2970.
Gautier et al., (1987). "Alpha-DNA. IV: Alpha-anomeric and beta-anomeric tetrathymidylates covalently linked to intercalating oxazolopyridocarbazole. Synthesis, physicochemical properties and poly (rA) binding," Nucleic Acids Research, 15(16):6625-6641.
Gerlinger et al., (2013). "Ultra-deep T cell receptor sequencing reveals the complexity and intratumour heterogeneity of T cell clones in renal cell carcinomas," The Journal of Pathology, 231(4):424-432.
Ghasemzadeh et al., (2016). "New strategies in bladder cancer: a second coming for immunotherapy," Clin Cancer Research, 22(4):793-801.
Ginzinger et al., (2000). "Measurement of DNA Copy Number at Microsatellite Loci Using Quantitative PCR Analysis," Cancer Research, 60(19):5405-5409.
Gnirke et al., (2009). "Solution hybrid selection with ultra-long oligonucleotides for massively parallel targeted sequencing," Nature Biotechnology, 27(2):182-189.
Govindan et al., (2012). "Genomic landscape of non-small cell lung cancer in smokers and neversmokers," Cell, 150(6):1121-34 and supplemental content, 24 pages.
Gram et al., (1992). "In vitro selection and affinity maturation of antibodies from a naïve combinatorial immunoglobulin library," PNAS, 89:3576-3580.
Green et al., (1994). "Antigen-specific human monoclonal antibodies from mice engineered with human Ig heavy and light chain YACs," Nature Genetics, 7:13-21.
Griffin et al., (1993). "DNA sequencing. Recent innovations and future trends," Applied Biochemistry and Biotechnology, 38(1-2):147-159.
Griffiths et al., (1993). "Human anti-self antibodies with high specificity from phage display libraries," The EMBO Journal, 12(2):725-734.
Guatelli et al., (1990). "Isothermal, in vitro amplification of nucleic acids by a multienzyme reaction modeled after retroviral replication," PNAS, 87(5):1874-1878.
Gubin et al., (2014). "Checkpoint Blockade Cancer Immunotherapy Targets Tumour-Specific Mutant Antigens," Nature, 515(7528):577-81, 32 pages.
Gubin et al., (2015). "The odds of immunotherapy success," Science, 350(6257):158-159.
Gui et al., (2011). "Frequent mutations of chromatin remodeling genes in transitional cell carcinoma of the bladder," Nat Genet, 43(9):875-8, 14 pages.
Hamid et al., (2013). "Safety and tumor responses with lambrolizumab (anti-PD-1) in melanoma," The New England Journal of Medicine, 369(2):134-144.
Han et al., (2001). "Evaluation of denaturing high performance liquid chromatography (DHPLC) for the mutational analysis of the neurofibromatosis type 1 (NF1) gene," Human Genetics, 109:487-497.
Hansen et al., (2016). "PD-L1 Testing in Cancer: Challenges in Companion Diagnostic Development," JAMA Oncology, 2(1):15-16.
Haselhoff et al., (1988). "Simple RNA enzymes with new and highly specific endoribonuclease activities," Nature, 334:585-591.
Hawkins et al., (1992). "Selection of phage antibodies by binding affinity: Mimicking affinity maturation," Journal of Molecular Biology, 226(3):889-896.
Hay et al., (1992). "Bacteriophage cloning and *Escherichia coli* expression of a human IgM Fab," Human Antibodies and Hybridomas, 3(2):81-85.

Helene et al., (1992). "Control of gene expression by triple helix-forming oligonucleotides. The antigene strategy," Annals of the New York Academy of Sciences, 660:27-36.
Helene, (1991). "The anti-gene strategy: control of gene expression by triplex-forming-oligonucleotides," Anti-cancer Drug Design, 6(6):569-584.
Henick et al., (2014). "The PD-1 pathway as a therapeutic target to overcome immune escape mechanisms in cancer," Expert Opin Ther Targets., 18(12):1407-20.
Herbst et al., (2014). "Predictive correlates of response to the anti-PD-L1 antibody MPDL3280A in cancer patients," Nature, 515:563-567.
Hodis et al., (2012). "A Landscape of Driver Mutations in Melanoma," Cell, 150(2):251-263.
Hoogenboom et al., (1991). "Multi-subunit proteins on the surface of filamentous phage: methodologies for displaying antibody (Fab) heavy and light chains," Nucleic Acids Research, 19(15):4133-4137.
Houghten et al., (1992). "The use of synthetic peptide combinatorial libraries for the identification of bioactive peptides," Biotechniques, 13(3):412-421.
Howitt et al., (2015). "Association of Polymerase e-Mutated and Microsatellite-Instable Endometrial Cancers With Neoantigen Load, Number of Tumor-Infiltrating Lymphocytes, and Expression of PD-1 and PL-L 1," JAMA Oncol., 1(9):1319-23.
Hudson et al., (1997). "Novel and recurrent mutations in the neurofibromatosis type 1 (NF1) gene," Human Mutation, 9(4):366-367.
Hugo et al., (2016). "Genomic and Transcriptomic Features of Response to Anti-PD-1 Therapy in Metastatic Melanoma," Cell, 165(1):35-44.
Huse et al., (1989). "Generation of a Large Combinatorial Library of the Immunoglobulin Repertoire in Phage Lambda," Science, 246(4935):1275-1281.
Hyrup et al., (1996). "Peptide Nucleic Acids (PNA): Synthesis, properties and potential applications," Bioorganic & Medicinal Chemistry, 4(1):5-23.
Inoue et al., (1987). "Sequence-dependent hydrolysis of RNA using modified oligonucleotide splints and RNase H," FEBS Letters, 215(2):327-330.
Inoue et al., (1987). "Synthesis and hybridization studies on two complementary nona(2'-O-methyl)ribonucleotides," Nucleic Acids Research, 15(15):6131-6148.
International Preliminary Report on Patentability for International Patent Application No. PCT/US2017/019682, dated Sep. 4, 2018 (8 pages).
International Preliminary Report on Patentability for International Patent Application No. PCT/US2017/019763, dated Sep. 4, 2018 (19 pages).
International Preliminary Report on Patentability for International Patent Application No. PCT/US2017/055669, dated Apr. 9, 2019 (13 pages).
International Preliminary Report on Patentability for International Patent Application No. PCT/US2018/043074, dated Jan. 21, 2020 (9 pages).
International Search Report and Written Opinion for International Patent Application No. PCT/US2017/019682, dated Apr. 24, 2017 (17 pages).
International Search Report and Written Opinion for International Patent Application No. PCT/US2017/019763, dated Aug. 2, 2017 (25 pages).
International Search Report and Written Opinion for International Patent Application No. PCT/US2017/055669, dated Jan. 8, 2018 (17 pages).
International Search Report and Written Opinion for International Patent Application No. PCT/US2018/043074, dated Oct. 29, 2018 (13 pages).
Jing et al., (2016). "PD-I/PD-LI blockades in non-small-cell lung cancer therapy," Onco Targets Ther., 9:489-502.
Johnson et al., (2015). "Clinical Activity of Ipilimumab in Acral Melanoma: A Retrospective Review," The Oncologist, 20(6):648-652.

(56) References Cited

OTHER PUBLICATIONS

Johnson et al., (2015). "Impact of NRAS Mutations for Patients with Advanced Melanoma Treated with Immune Therapies," Cancer Immunology Research, 3(3):288-295.
Johnson et al., (2017). "Targeted Next Generation Sequencing Identifies Markers of Response to PD-1 Blockade," Cancer Immunol Res., 4(11):959-67.
Jones et al., (1986). "Replacing the complementarity-determining regions in a human antibody with those from a mouse," Nature, 321(6069):552-525.
Kallioniemi et al., (1992). "ERBB2 amplification in breast cancer analyzed by fluorescence in situ hybridization," PNAS, 89(12):5321-5325.
Kates et al., (2016). "Immune checkpoint inhibitors: a new frontier in bladder cancer," World J Urol., 34(1):49-55.
Kaufmann et al., (2001). "Spinal neurofibromatosis without café-au-lait macules in two families with null mutations of the NF1 gene," American Journal of Human Genetics, 69(6):1395-1400.
Kim et al., (2015). "Emerging immunotherapies for bladder cancer," Curr Opin Oncol., 27(3):191-200, 19 pages.
Kim, (2016). "Immune checkpoint blockade therapy for bladder cancer treatment," Investig Clin Urol., 57(Suppl 1):S98-S105 (2016).
Klose et al., (1998). "Selective Disactivation of Neurofibromin GAP Activity in Neurofibromatosis Type 1 (NF1)," Human Molecular Genetics, 7(8):1261-1268.
Kluwe et al., (2002). "NF1 mutations in neurofibromatosis 1 patients with plexiform neurofibromas," Human Mutation, 19(3):309.
Kluwe et al., (2003). "Molecular study of frequency of mosaicism in neurofibromatosis 2 patients with bilateral vestibular schwannomas," Journal of Medical Genetics, 40:109-114.
Knowles et al., (2015). "Molecular biology of bladder cancer: new insights into pathogenesis and clinical diversity," Nature Reviews Cancer, 15(1):25-41, 28 pages.
Kowanetz et al., (2017). "Tumor Mutation Burden (TMB) is Associated with Improved Efficacy of Atezolizumab in 1 Land 2L+ NSCLC Patients," J Thorac Oncol., 12(1):S321-2 OA20.01. Abstract.
Krauthammer et al., (2012). "Exome sequencing identifies recurrent somatic RAC1 mutations in melanoma," Nature Genetics, 44:1006-1014, 30 pages.
Krauthammer et al., (2015). "Exome sequencing identifies recurrent mutations in NF1 and RASopathy genes in sun-exposed melanomas," Nature Genetics, 47(9):996-1002, 25 pages.
Krkljus et al., (1998). "Analysis of CpG C-to-T mutations in neurofibromatosis type 1," Human Mutation, 11(5):411, 11 pages.
Kurtoglu et al., (2015). "Elevating the Horizon: Emerging Molecular and Genomic Targets in the Treatment of Advanced Urothelial Carcinoma," Clin Genitourin Cancer, 13(5):410-20, 23 pages.
Kwoh et al., (1989). "Transcription-based amplification system and detection of amplified human immunodeficiency virus type 1 with a bead-based sandwich hybridization format," PNAS, 86(4):1173-1177.
Lam et al., (1991). "A new type of synthetic peptide library for identifying ligand-binding activity," Nature, 354:82-84.
Lam, (1997). "Mini-review. Application of combinatorial library methods in cancer research and drug discovery," Anti-cancer Drug Design, 12(3):145-167.
Landegren et al., (1988). "A ligase-mediated gene detection technique," Science, 241(4869):1077-1080.
Larkin et al., (2015). "Combined Nivolumab and Ipilimumab or Monotherapy in Untreated Melanoma," The New England Journal of Medicine, 373(1):23-34.
Le et al., (2015). "PD-1 Blockade in Tumors with Mismatch-Repair Deficiency," N Engl J Med., 372(26):2509-2520.
Legrand et al., (2018). "Association of high tissue TMB and atezolizumab efficacy across multiple tumor types," J Clin Oncol., 36(15 suppl):12000, 3 pages.
Lemaitre et al., (1987). "Specific antiviral activity of a poly(L-lysine)-conjugated oligodeoxyribonucleotide sequence complementary to vesicular stomatitis virus N protein mRNA initiation site," PNAS, 84(3):648-652.
Letsinger et al., (1989). "Cholesteryl-conjugated oligonucleotides: synthesis, properties, and activity as inhibitors of replication of human immunodeficiency virus in cell culture," PNAS, 86(17):6553-6556.
Li et al., (1992). "Somatic mutations in the neurofibromatosis 1 gene in human tumors," Cell, 69(2):275-281.
Li et al., (1995). "Genomic organization of the neurofibromatosis 1 gene (NF1)," Genomics, 25(1):9-18.
Liu et al., (1987). "Chimeric mouse-human IgG1 antibody that can mediate lysis of cancer cells," PNAS, 84(10):3439-3443.
Liu et al., (1987). "Production of a mouse-human chimeric monoclonal antibody to CD20 with potent Fc-dependent biologic activity," The Journal of Immunology, 139(10):3521-3526.
Liu et al., (2000). "Genomic Organization of a New Candidate Tumor Suppressor Gene, LRP1B," Genomics, 69(2):271-274.
Liu et al., (2000). "LRP-DIT, a Putative Endocytic Receptor Gene, Is Frequently Inactivated in Non-Small Cell Lung Cancer Cell Lines," Cancer Research, 60(7):1961-1967.
Llosa et al., (2015). "The Vigorous Immune Microenvironment of Microsatellite Instable Colon Cancer Is Balanced by Multiple Counter-Inhibitory Checkpoints," Cancer Discov., 5(1):43-51.
Lonberg et al., (1994). "Antigen-specific human antibodies from mice comprising four distinct genetic modifications," Nature, 368:856-859.
Luke et al., (2013). "Clinical activity of ipilimumab for metastatic uveal melanoma: a retrospective review of the Dana-Farber Cancer Institute, Massachusetts General Hospital, Memorial Sloan-Kettering Cancer Center, and University Hospital of Lausanne experience," Cancer, 119(20):3687-3695.
Maby et al., (2015). "Correlation between Density of COB+ T-cell Infiltrate in Microsatellite Unstable Colorectal Cancers and Frameshift Mutations: A Rationale for Personalized Immunotherapy," Cancer Res., 75(17):3446-55.
Maher, (1992). "DNA triple-helix formation: an approach to artificial gene repressors?," Bioessays, 14(12):807-815.
Marchuk et al., (1991). "cDNA cloning of the type 1 neurofibromatosis gene: complete sequence of the NF1 gene product," Genomics, 11(4): 931-940.
Marcq et al., (2015). "Targeting immune checkpoints: New opportunity for mesothelioma treatment?" Cancer Treat Rev., 41(10):914-24.
Martin et al., (1990). "The GAP-related domain of the neurofibromatosis type 1 gene product interacts with ras p21," Cell, 63(4):843-849.
Masuda et al., (1999). "Analysis of chemical modification of RNA from formalin-fixed samples and optimization of molecular biology applications for such samples," Nucleic Acids Research, 27(22):4436-4443.
Mattocks et al., (2004). "Automated comparative sequence analysis identifies mutations in 89% of NF1 patients and confirms a mutation cluster in exons 11-17 distinct from the GAP related domain," Journal of Medical Genetics, 41(4):E48.
Maxam et al., (1977). "A new method for sequencing DNA," PNAS, 74(2):560-564.
Maynard et al., (1997). "Characterization and significance of nine novel mutations in exon 16 of the neurofibromatosis type 1 (NF1) gene," Human Genetics, 99(5):674-676.
Melero et al., (2015). "Evolving synergistic combinations of targeted immunotherapies to combat cancer," Nat Rev Cancer, 15(8):457-72.
Meng et al., (2015). "Predictive biomarkers in PD-1/PD-L 1 checkpoint blockade immunotherapy," Cancer Treat Rev, 41(10):868-76.
Messiaen et al., (1999). "Exon 10b of the NF1 gene represents a mutational hotspot and harbors a recurrent missense mutation Y489C associated with aberrant splicing," Genetics in Medicine, 1(6):248-253.
Metzker, (2010). "Sequencing technologies—the next generation," Nature Reviews Genetics, 11(1):31-46.
Millis et al., (2015). "Molecular Profiling of Infiltrating Urothelial Carcinoma of Bladder and Nonbladder Oriain," Clin Genitourin Cancer, 13(1):e37-49.
Morrison et al., (1984). "Chimeric human antibody molecules: mouse antigen-binding domains with human constant region domains," PNAS, 81(21):6851-6855.

(56) References Cited

OTHER PUBLICATIONS

Morrison, (1985). "Transfectomas provide novel chimeric antibodies," Science, 229(4719):1202-1207.
Morse et al., (2017). "Elevated tumor mutational burden and prolonged clinical response to anti-PD-L1 antibody in platinum-resistant recurrent ovarian cancer," Gynecol Oncol Rep., 21:78-80.
Naeve et al., (1995). "Accuracy of automated DNA sequencing: a multi-laboratory comparison of sequencing results," Biotechniques, 19(3):448-453.
Nath et al., (1998). "Fluorescence in situ hybridization (FISH): DNA probe production and hybridization criteria," Biotechnic & Histochemistry, 73(1):6-22.
Nemethova et al., (2013). "Thirty-nine novel neurofibromatosis 1 (NF1) gene mutations identified in Slovak patients," Annals of Human Genetics, 77(5):364-379.
Nikolaev et al., (2011). "Exome sequencing identifies recurrent somatic MAP2K1 and MAP2K2 mutations in melanoma," Nature Genetics, 44(2):133-139.
Nishi et al., (1991). "Differential expression of two types of the neurofibromatosis type 1 (NF1) gene transcripts related to neuronal differentiation," Oncogene, 6(9):1555-1559.
Nishimura et al., (1987). "Recombinant human-mouse chimeric monoclonal antibody specific for common acute lymphocytic leukemia antigen," Cancer Research, 47(4):999-1005.
Nissan et al., "Loss of NF1 in Cutaneous Melanoma Is Associated with RAS Activation and MEK Dependence," Cancer Research (2014) vol. 74, No. 8, pp. 2340-2350.
Nystrom et al., (2009). "Noonan syndrome and neurofibromatosis type I in a family with a novel mutation in NF1," Clinical Genetics, 76(6):524-534.
Oi et al., (1986). "Chimeric antibodies," BioTechniques, 4(3):214-221.
Perry-O'Keefe et al., (1996). "Peptide nucleic acid pre-gel hybridization: an alternative to southern hybridization," PNAS, 93(25):14670-14675.
Peters et al., (1999). "A novel mutation L1425p in the GAP-region of the NF1 gene detected by temperature gradient gel electrophoresis (TGGE)," Human Mutation, 13(4):337.
Peters et al., (2022). "Atezolizumab versus chemotherapy in advanced or metastatic NSCLC with high blood-based tumor mutational burden: primary analysis of BFAST cohort C randomized phase 3 trial," Nat Med. 28(9):1831-1839, 23 pages.
Pinkel et al., (1988). "Fluorescence in situ hybridization with human chromosome-specific libraries: detection of trisomy 21 and translocations of chromosome 4," PNAS, 85(23):9138-9142.
Pinkel et al., (1998). "High resolution analysis of DNA copy number variation using comparative genomic hybridization to microarrays," Nature Genetics, 20(2):207-211.
Ponti et al., (2011). "Clinico-pathological and biomolecular findings in Italian patients with multiple cutaneous neurofibromas," Hereditary Cancer in Clinical Practice, 9(1):6.
Postow et al., (2013). "Ipilimumab for patients with advanced mucosal melanoma," Oncologist, 18(6):726-732.
Powles et al., (2014). "MPDL3280A (anti-PD-L 1) treatment leads to clinical activity in metastatic bladder cancer," Nature, 515(7528):558-62.
Redman et al., (2016). "Advances in immunotherapy for melanoma," BMC Medicine, 14(1):20, 11 pages.
Rizvi et al., (2015). "Activity and safety of nivolumab, an anti-PD-1 immune checkpoint inhibitor, for patients with advanced, refractory squamous non-small-cell lung cancer (CheckMate 063): a phase 2, single-arm trial," The Lancet Oncology, 16(3):257-265, 21 pages.
Robert et al., (2015). "Nivolumab in previously untreated melanoma without BRAF mutation," The New England Journal of Medicine, 372(4):320-30.
Robert et al., (2015). "Pembrolizumab versus Ipilimumab in Advanced Melanoma," The New England Journal of Medicine, 372(26):2521-2532.
Rooney et al., (2015). "Molecular and Genetic Properties of Tumors Associated with Local Immune Cytolytic Activity," Cell, 160(1-2):48-61.
Rosenberg et al., (2016). "Atezolizumab in patients with locally advanced and metastatic urothelial carcinoma who have progressed following treatment with platinum-based chemotherapy: a singlearm, multicentre, phase 2 trial," Lancet, 387(10031):1909-20 and supplementary appendix, 37 pages.
Rothe et al., (2014). "Plasma circulating tumor DNA as an alternative to metastatic biopsies for mutational analysis in breast cancer," Ann Oncol., 25(10):1959-1965.
Sanger et al., (1977). "DNA sequencing with chain-terminating inhibitors," PNAS, 74(12):5463-5467.
Schumacher et al., (2015). "Biomarkers in Cancer Immunotherapy," Cancer Cell, 27(1):12-14.
Schumacher et al., (2015). "Neoantigens in cancer immunotherapy," Science, 348(6230):69-74.
Scott et al., (1990). "Searching for peptide ligands with an epitope library," Science, 249(4967):386-390.
Search Report received for Chinese Patent Application No. 201780074244.6 dated Sep. 3, 2020, 7 pages.
Search Report received for Taiwanese Patent Application No. 106134604 dated Feb. 17, 2022, 2 pages.
Shaw et al., (1988). "Mouse/human chimeric antibodies to a tumor-associated antigen: biologic activity of the four human IgG subclasses," Journal of the National Cancer Institute, 80(19):1553-1559.
Shen et al., (1993). "Neurofibromatosis type 1 (NF1): the search for mutations by PCR-heteroduplex analysis on Hydrolink gels," Human Molecular Genetics, 2(11):1861-1864. Abstract Only.
Shen et al., (1996). "Molecular genetics of neurofibromatosis type 1 (NF1)," Journal of Medical Genetics, 33(1):2-17.
Shen et al., (2015). "ARID1A Deficiency Impairs the DNA Damage Checkpoint and Sensitizes Cells to PARP Inhibitors," Cancer Discovery, 5(7):752-767, 27 pages.
Shinohara et al., (1994). "Structure and chromosomal localization of the human PD-1 gene (PDCD1)," Genomics, 23(3):704-706.
Siolas et al., (2005). "Synthetic shRNAs as potent RNAi triggers," Nature Biotechnology, 23(2):227-231.
Sjöblom et al., (2006). "The consensus coding sequences of human breast and colorectal cancers," Science, 314(5797):268-274.
Smith et al., (2006). "Common fragile sites, extremely large genes, neural development and cancer," Cancer Letters, 232(1):48-57.
Snyder et al., "Genetic Basis for Clinical Response to CTLA-4 Blockade in Melanoma," N Engl J Med (2014) vol. 371, No. 23, pp. 2189-2199.
Specht et al., (2001). "Quantitative gene expression analysis in microdissected archival formalin-fixed and paraffin-embedded tumor tissue," The American Journal of Pathology, 158(2):419-429.
Spranger et al., (2015). "Melanoma-intrinsic β-catenin signaling prevents anti-tumour immunity," Nature, 523(7559):231-235.
Stephens et al., (2016). "Analytic validation of a clinical circulating tumor DNA assay for patients with solid tumors," Ann Oncol., 27(Suppl. 6):vi401-vi406. Abstract Only.
Strickland et al., (2016). "Association and prognostic significance of BRCA1/2-mutation status with neoantigen load, number of tumor-infiltrating lymphocytes and expression of PD-1 /PD-L 1 in high grade serous ovarian cancer," Oncotarget, 7(12):13587-13598.
Sun et al., (1987). "Chimeric antibody with human constant regions and mouse variable regions directed against carcinoma-associated antigen 17-1A," PNAS, 84(1):214-218.
Suzuki et al., (1991). "Brain tumors predominantly express the neurofibromatosis type 1 gene transcripts containing the 63 base insert in the region coding for GTPase activating protein-related domain," Biochemical and Biophysical Research Communications, 181(3):955-961.
Suzuki et al., (1992). "Molecular cloning of a cDNA coding for neurofibromatosis type 1 protein isoform lacking the domain related to ras GTPase-activating protein," Biochemical and Biophysical Research Communications, 187(2):984-990.
Tamborero et al., (2013). "OncodriveCLUST: exploiting the positional clustering of somatic mutations to identify cancer genes," Bioinformatics, 29(18):2238-44.

(56) References Cited

OTHER PUBLICATIONS

Tassabehji et al., (1993). "Tandem duplication within a neurofibromatosis type 1 (NF1) gene exon in a family with features of Watson syndrome and Noonan syndrome," American Journal of Human Genetics, 53(1):90-95.
Thomas et al., (2012). "Exploring the somatic NF1 mutational spectrum associated with NF1 cutaneous neurofibromas," European Journal of Human Genetics, 20(4):411-419.
Topalian et al., (2012). "Safety, activity, and immune correlates of anti-PD-1 antibody in cancer," The New England Journal of Medicine, 366(26):2443-2454.
Toulme, (2001). "New candidates for true antisense," Nature Biotechnology, 19(1):17-18.
Trapnell et al., (2009). "How to map billions of short reads onto genomes," Nature Biotechnology, 27(5):455-457.
Tuaillon et al., (1993). "Human immunoglobulin heavy-chain minilocus recombination in transgenic mice: gene-segment use in mu and gamma transcripts," PNAS, 90(8):3720-3724.
Tumeh et al., (2014). "PD-1 blockade induces responses by inhibiting adaptive immune resistance," Nature, 515(7528):568-571.
Upadhyaya et al., (1995). "Characterisation of germline mutations in the neurofibromatosis type 1 (NF1) gene," Journal of Medical Genetics, 32(9):706-710.
Upadhyaya et al., (1997). "Mutational and functional analysis of the neurofibromatosis type 1 (NF1) gene," Human Genetics, 99(1):88-92.
Upadhyaya et al., (1997). "Six novel mutations in the neurofibromatosis type 1 (NF1) gene," Human Mutation, 10(3):248-250.
Upadhyaya et al., (2007). "An absence of cutaneous neurofibromas associated with a 3-bp inframe deletion in exon 17 of the NF1 gene (c.2970-2972 delAAT): evidence of a clinically significant NF1 genotype-phenotype correlation," American Journal of Human Genetics, 80(1):140-151.
Vaish et al., (2005). "Microsatellite instability as prognostic marker in bladder tumors: a clinical significance," BMC Urol., 5:2.
Van Allen et al., (2015). "Genomic correlates of response to CTLA-4 blockade in metastatic melanoma," Science, 350(6257):207-211.
Van Buuren et al., (2014). "High sensitivity of cancer exome-based COB T cell neo-antigen identification," OncoImmunology, 3:e28836.
Vansteenkiste et al., (2017). "Prospects and progress of atezolizumab in non-small cell lung cancer," Expert Opin Biol Ther. 17(6):781-9.
Verhoeyan et al., (1988). "Reshaping human antibodies: grafting an antilysozyme activity," Science, 239(4847):1534-1536.
Wallace et al., (1990). "Type 1 neurofibromatosis gene: identification of a large transcript disrupted in three NF1 patients," Science, 249(4965):181-186.
Wang et al., (2003). "Neurofibromatosis type 1 gene as a mutational target in a mismatch repair-deficient cell type," Human Genetics, 112(2):117-123.
Warren et al., (2007). "Assembling millions of short DNA sequences using SSAKE," Bioinformatics, 23(4):500-501.
Weber et al., (2015). "Nivolumab versus chemotherapy in patients with advanced melanoma who progressed after anti-CTLA-4 treatment (CheckMate 037): a randomised, controlled, open-label, phase 3 trial," The Lancet Oncology, 16(4):375-384.
Wheeless et al., (1994). "Bladder irrigation specimens assayed by fluorescence in situ hybridization to interphase nuclei," Cytometry, 17(4):319-326.
Wiesner et al., (2015). "NF1 Mutations Are Common in Desmoplastic Melanoma," The American Journal of Surgical Pathology, 39(10):1357-1362.
Wikipedia, (2021). "Exome," Available online at <https://en.wikipedia.org/w/index.php?title=Exome&oldid=1010823778>, 6 pages.
Wolchok, (2015). "PD-1 Blockers," Cell, 162(5):937.
Wood et al., (1985). "The synthesis and in vivo assembly of functional antibodies in yeast," Nature, 314(6010):446-449.
Woolf et al., (1992). "Specificity of antisense oligonucleotides in vivo," PNAS, 89(16):7305-7309.
Wu et al., (1989). "The ligation amplification reaction (LAR)—amplification of specific DNA sequences using sequential rounds of template-dependent ligation," Genomics, 4(4):560-569.
Wu et al., (1996). "Neurofibromatosis type I gene mutation in a patient with features of LEOPARD syndrome," Human Mutation, 8(1):51-56.
Xu et al., (1990). "The neurofibromatosis type 1 gene encodes a protein related to GAP," Cell, 62(3):599-608.
Yamamoto et al., (2015). "Microsatellite instability: an update," Arch Toxicol., 89(6):899-921.
Yang et al., (2002). "Short RNA duplexes produced by hydrolysis with *Escherichia coli* RNase III mediate effective RNA interference in mammalian cells," PNAS, 99(15):9942-9947.
Yap et al., (2014). "Whole-Exome Sequencing of Muscle-Invasive Bladder Cancer Identifies Recurrent Mutations of UNC5C and Prognostic Importance of DNA Repair Gene Mutations on Survival," Clin Cancer Res., 20(24):6605-17.
Zatkova et al., (2004). "Disruption of exonic splicing enhancer elements is the principal cause of exon skipping associated with seven nonsense or missense alleles of NF1," Human Mutation, 24(6):491-501.
Zerbino et al., (2008). "Velvet: algorithms for de novo short read assembly using de Bruijn graphs," Genome Research, 18(5):821-829.
Zon, (1988). "Oligonucleotide analogues as potential chemotherapeutic agents," Pharmaceutical Research, 5(9):539-549.
Zuckermann et al., (1994). "Discovery of nanomolar ligands for 7-transmembrane G-protein-coupled receptors from a diverse N-(substituted)glycine peptoid library," Journal of Medicinal Chemistry, 37(17):2678-2685.
Gabril et al., (2014). "Molecular Testing in Urothelial Tumors," Molecular Testing in Cancer, pp. 301-317.
Protest and Filing of Prior Art References Prior to Grant for Canadian Patent Application No. 3,038,712, dated Jul. 22, 2021 (19 pages).
Purandare et al., (1994). "Characterisation of inherited and sporadic mutations in neurofibromatosis type-1," Human Molecular Genetics, 3(7):1109-1115.
Upadhyaya et al., (1992). "Analysis of mutations at the neurofibromatosis 1 (NF1) locus," Human Molecular Genetics, 1(9):735-740.
Upadhyaya et al., (1994). "Molecular basis of neurofibromatosis type 1 (NF1): mutation analysis and polymorphisms in the NF1 gene," Human Mutation, 4(2):83-101.
Suzuki et al., (1995). "Evidence for the presence of two amino-terminal isoforms of neurofibromin, a gene product responsible for neurofibromatosis type 1," The Tohoku Journal of Experimental Medicine, 175(4): 225-233. Abstract Only.
Abernathy et al., (1994). "Two NF1 mutations: Frameshift in the GAP-related domain, and loss of two codons toward the 3' end of the gene," Human Mutation, 3(4):347-352.
Baralle et al., (2003). "Different mutations in the NF1 gene are associated with Neurofibromatosis-Noonan syndrome (NFNS)," American Journal of Medical Genetics, 119A(1):1-8.
Krol et al., (1988). "Modulation of eukaryotic gene expression by complementary RNA or DNA sequences," BioTechniques, 6(10):958-976.
Chen et al., (2020). "Effect of Combined Immune Checkpoint Inhibition vs Best Supportive Care Alone in Patients with Advanced Colorectal Cancer: The Canadian Cancer Trials Group CO.26 Study," JAMA Oncol., 6(6):831-838.
Schrock et al., (2016). "Characterization of 298 Patients with Lung Cancer Harboring MET Exon 14 Skipping Alterations," J Thorac Oncol., 11(9):1493-502.
Smith et al., (2016). "SomVarIUS: somatic variant identification from unpaired tissue samples," Bioinformatics, 32(6):808-13.
Friedman et al., (2022). "Atezolizumab Treatment of Tumors with High Tumor Mutational Burden from MyPathway, a Multicenter, Open-Label, Phase IIa Multiple Basket Study," Cancer Discov, 12(3):OF1-OF16, (16 pages).
Aggarwal et al., (2020). "Baseline Plasma Tumor Mutation Burden Predicts Response to Pembrolizumab based Therapy in Patients

(56) References Cited

OTHER PUBLICATIONS with Metastatic Non-Small Cell Lung Cancer," Clinical Cancer Research. 26(10):2354-2361 (9 pages).

Chae et al., (2019). "Clinical Implications of Circulating Tumor DNA Tumor Mutational Burden (ctDNA TMB) in Non-Small Cell Lung Cancer," The Oncologist. 24(6):820-28.

Wang et al., (2019). "Assessment of Blood Tumor Mutational Burden as a Potential Biomarker for Immunotherapy in Patients With Non-Small Cell Lung Cancer With Use of a Next-Generation Sequencing Cancer Gene Panel," Jama Oncology. 5(5):696-702.

Davis et al., (2017). "Comparison of tumor mutational burden (TMB) across tumor tissue and circulating tumor DNA (ctDNA)," Journal of Clinical Oncology, 35(15_suppl):e23028, 2 pages.

Sato et al., (2016). "Individualized Mutation Detection in Circulating Tumor DNA for Monitoring Colorectal Tumor Burden Using a Cancer-Associated Gene Sequencing Panel," PLoS One, 11(1):e0146275, 15 pages.

International Preliminary Report on Patentability for International Application No. PCT/US2017/019733, dated Aug. 11, 2017, 13 pages.

Asmar et al., Clinical utility of nivolumab in the treatment of advanced melanoma.†

Campesato et al., Comprehensive cancer-gene panels can be used to estimate mutational load and predict clinical benefit to PD-1 blockade in clinical practice.†

\* cited by examiner
† cited by third party

SEQUENCE LISTING

<160> NUMBER OF SEQ ID NOS: 1

<210> SEQ ID NO 1
<211> LENGTH: 14
<212> TYPE: PRT

```
<213> ORGANISM: Homo sapiens

<400> SEQUENCE: 1

Gly His Glu Gln Gln Lys Leu Pro Ala Ala Thr Leu Ala Leu
1               5                   10
```

METHODS OF TREATING CANCER

CROSS REFERENCE TO RELATED APPLICATIONS

This application is a U.S. National Phase Application under 35 U.S.C. § 371 of International Application No. PCT/US2017/019733, filed Feb. 27, 2017, which claims the benefit of U.S. Provisional Application No. 62/301,510, filed Feb. 29, 2016. The contents of each of the aforementioned applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 24, 2017, is named F2036-7062WO_SL.txt and is 4,096 bytes in size.

FIELD OF THE INVENTION

The invention relates to methods and compositions for treating cancer such as melanoma.

BACKGROUND OF THE INVENTION

Agents targeting the programmed death-1/ligand (PD-1/PD-L1) axis release suppressed anti-tumor T cell responses, resulting in remarkable clinical activity in numerous cancers (Wolchok. *Cell* 162:937, 2015). Nivolumab and pembrolizumab induce clinical responses in 25-45% of patients with advanced melanoma and are now widely used following regulatory approval (Topalian et al. *N Engl J Med* 366:2443-54, 2012; Hamid et al. *N Engl J Med* 369:134-44, 2013; Herbst et al. *Nature* 515:563-7, 2014; Robert et al. *N Engl J Med,* 372:2521-32, 2015; Robert et al. *N Engl J Med,* 372:320-30, 2014; Larkin et al. *N Engl J Med,* 373:1270-1, 2015). Despite this activity, clinically-accessible and validated markers to predict response and guide treatment decision-making have remained elusive. Recently, clonal expansion of infiltrating T cells and PD-L1 expression by tumor or immune cells were implicated as potential markers of treatment response (Topalian et al. *N Engl J Med* 366: 2443-54, 2012; Herbst et al. *Nature* 515:563-7, 2014; Tumeh et al. *Nature* 515:568-71, 2014; Weber et al. *Lancet Oncol,* 16:375-84, 2015).

Despite these findings, the impact of mutational load and specific oncogenic mutations in melanoma in response to agents that inhibit PD-1 or PD-L1 has not been systematically explored. Furthermore, translating genomic studies to routine clinical practice remains problematic as whole exome sequencing (WES) is not widely available and is expensive, time intensive, and technically challenging.

Therefore, the need exists for novel therapeutic and diagnostic approaches, including immunotherapies and genomic tesings, for treating and diagnosing cancer such as melanomas.

SUMMARY OF THE INVENTION

The invention is based, at least in part, on the discovery that mutational load correlates with therapeutic benefit from a therapy that includes an inhibitor of PD-1 or PD-L1 in melanoma. In one embodiment, profiling a small fraction of the genome or exome, e.g., using a hybrid capture-based, next-generation sequencing (NGS) platform, from a patient sample serves as an effective surrogate for the analysis of total mutational load. In another embodiment, an alteration detected in a single gene (e.g., an NF1 or LRP1B gene) serves as an alternative or further surrogate for total mutational burden to predict a response to the therapy. Using methods that include a targeted NGS platform for detecting mutational burden has several advantages, including, but not limited to, faster, e.g., more clinically manageable turn-around times (~2 weeks), standardized informatics pipelines, and more manageable costs, compared to, e.g., whole genome or whole exome sequencing. The methods disclosed herein have other advantages over markers such as PD-L1 expression, since they produce an objective measure (e.g., mutation load) rather than a subjective measure (e.g., pathology scoring). The methods disclosed herein also allow for simultaneous detection of actionable alterations for targeted therapies, as well as mutational burden for immune therapies. These methods can provide clinically actionable predictors of a response to anti-PD-1 and/or anti-PD-L1 therapies in patients with advanced melanoma.

Accordingly, the invention provides, at least in part, methods for treating a subject having, or at risk of having, a cancer (e.g., a melanoma), by administering to the subject an effective amount of an agent (e.g., a therapeutic agent) that targets and/or inhibits the PD-1 pathway. In certain embodiments, the therapeutic agent is an inhibitor of PD-1 or PD-L1. In certain embodiments, the therapeutic agent, e.g., the inhibitor of PD-1 or PD-L1, is administered responsive to a value of responder status to the therapeutic agent. In certain embodiments, the value of responder status includes a measure of the mutation load in a sample (e.g., a tumor sample) from the subject. In certain embodiments, the measure of the mutation load includes a determination of one or more of: the level of a somatic alteration in a predetermined set of genes disclosed herein, the presence of a somatic alteration in an NF1 gene, the number of a somatic alteration in an LRP1B gene, or the number of a C to T transition in a predetermined set of genes disclosed herein, or any combination thereof.

Methods of Treatment

In one aspect, the invention features a method of treating a subject having a cancer, e.g., a melanoma. The method includes:

(a) acquiring a value of responder status to a therapy, e.g., a therapy comprising an inhibitor of PD-1 or PD-L1, for the subject, wherein said value of responder status comprises a measure of the mutation load in a sample, e.g., a melanoma sample or a sample derived from a melanoma, from the subject; and (b) responsive to an increased value of responder status, e.g., compared to a reference value of responder status, administering to the subject the therapy, thereby treating the subject.

In certain embodiments, the reference value of responder status is a value of responder status for a non-responder to the therapy.

In certain embodiments, the measure of the mutation load comprises a determination of one, two, three or all of the following in the sample from the subject:

(i) the level of a somatic alteration (e.g., one or more somatic alterations) in a predetermined set of genes set forth in Table 1;

(ii) the presence or absence of a somatic alteration (e.g., one or more somatic alterations) in an NF1 gene;

(iii) the number of a somatic alteration (e.g., one or more somatic alterations) in an LRP1B gene; or (iv) the number of a C to T transition (e.g., one or more C to T transitions) in a predetermined set of genes set forth in Table 1.

In certain embodiments, the therapy is administered to the subject, responsive to one, two, three or all of the following in the sample from the subject:

(i) an increased level of a somatic alteration (e.g., one or more somatic alterations) in a predetermined set of genes set forth in Table 1, e.g., compared to a reference level of a somatic alteration (e.g., one or more somatic alterations) in the predetermined set of genes set forth in Table 1;

(ii) the presence of a somatic alteration (e.g., one or more somatic alterations) in the NF1 gene;

(iii) an increased number of a somatic alteration (e.g., one or more somatic alterations) in the LRP1B gene, e.g., compared to a reference number of a somatic alteration (e.g., one or more somatic alterations) in the LRP1B gene; or (iv) an increased number of a C to T transition (e.g., one or more C to T transitions) in a predetermined set of genes set forth in Table 1, e.g., compared to a reference number of a C to T transition (e.g., one or more C to T transitions) in the predetermined set of genes set forth in Table 1.

In another aspect, the invention features a method of treating a subject having a cancer, e.g., a melanoma. The method includes: administering a therapy, e.g., a therapy comprising an inhibitor of PD-1 or PD-L1, to the subject, wherein the subject has, or has been identified as having, an increased value of responder status, e.g., compared to a reference value of responder status, and wherein said value of responder status comprises a measure of the mutation load in a sample, e.g., a melanoma sample or a sample derived from a melanoma, from the subject, thereby treating the subject.

In certain embodiments, the measure of the mutation load comprises a determination of one, two, three or all of the following in the sample from the subject:

(i) the level of a somatic alteration (e.g., one or more somatic alterations) in a predetermined set of genes set forth in Table 1;

(ii) the presence or absence of a somatic alteration (e.g., one or more somatic alterations) in an NF1 gene;

(iii) the number of a somatic alteration (e.g., one or more somatic alterations) in an LRP1B gene; or (iv) the number of a C to T transition (one or more C to T transitions) in a predetermined set of genes set forth in Table 1.

In certain embodiments, the therapy is administered to the subject, responsive to one, two, three or all of the following in the sample from the subject:

(i) an increased level of a somatic alteration (e.g., one or more somatic alterations) in a predetermined set of genes set forth in Table 1, e.g., compared to a reference level of a somatic alteration (e.g., one or more somatic alterations) in the predetermined set of genes set forth in Table 1;

(ii) the presence of a somatic alteration (e.g., one or more somatic alterations) in the NF1 gene;

(iii) an increased number of a somatic alteration (e.g., one or more somatic alterations) in the LRP1B gene, e.g., compared to a reference number of a somatic alteration (e.g., one or more somatic alterations) in the LRP1B gene; or (iv) an increased number of a C to T transition (e.g., one or more C to T transitions) in a predetermined set of genes set forth in Table 1, e.g., compared to a reference number of a C to T transition (e.g., one or more C to T transitions) in the predetermined set of genes set forth in Table 1.

In yet another aspect, the invention features a method of treating a subject having a cancer, e.g., a melanoma. The method includes:

(a) determining one or more of the following in a sample, e.g., a melanoma sample or a sample derived from a melanoma, from the subject:

(i) the level of a somatic alteration (e.g., one or more somatic alterations) in a predetermined set of genes, e.g., set forth in Table 1;

(ii) the presence or absence of a somatic alteration (e.g., one or more somatic alterations) in an NF1 gene;

(iii) the number of a somatic alteration (e.g., one or more somatic alterations) in an LRP1B gene; or (iv) the number of a C to T transition (one or more C to T transitions) in a predetermined set of genes set forth in Table 1; and (b) responsive to one or more of the following:

(i) an increased level of a somatic alteration (e.g., one or more somatic alterations) in a predetermined set of genes set forth in Table 1, e.g., compared to a reference level of a somatic alteration (e.g., one or more somatic alterations) in the predetermined set of genes set forth in Table 1;

(ii) the presence of a somatic alteration (e.g., one or more somatic alterations) in the NF1 gene;

(iii) an increased number of a somatic alteration (e.g., one or more somatic alterations) in the LRP1B gene, e.g., compared to a reference number of a somatic alteration (e.g., one or more somatic alterations) in the LRP1B gene; or (iv) an increased number of a C to T transition (e.g., one or more C to T transitions) in a predetermined set of genes set forth in Table 1, e.g., compared to a reference number of a C to T transition (e.g., one or more C to T transitions) in the predetermined set of genes set forth in Table 1, administering a therapy, e.g., a therapy comprising an inhibitor of PD-1 or PD-L1, to the subject.

Methods of Selecting a Therapy

In an aspect, the invention features a method of selecting a therapy, e.g., a therapy comprising an inhibitor of PD-1 or PD-L1, for a subject having a cancer, e.g., a melanoma. The method includes: acquiring a value of responder status to the therapy for the subject, wherein said value of responder status comprises a measure of the mutation load in a sample, e.g., a melanoma sample or a sample derived from a melanoma, from the subject, and wherein an increased value of responder status, e.g., compared to a reference value of responder status, indicates that said subject is, or is likely to be, a responder to the therapy, or said subject will, or will likely, respond to the therapy, thereby selecting the therapy.

In certain embodiments, the measure of the mutation load comprises a determination of one, two, three or all of the following in the sample from the subject:

(i) the level of a somatic alteration (e.g., one or more somatic alterations) in a predetermined set of genes set forth in Table 1;

(ii) the presence or absence of a somatic alteration (e.g., one or more somatic alterations) in an NF1 gene;

(iii) the number of a somatic alteration (e.g., one or more somatic alterations) in an LRP1B gene; or (iv) the number of a C to T transition (one or more C to T transitions) in a predetermined set of genes set forth in Table 1.

In certain embodiments, the therapy is administered to the subject, responsive to one, two, three or all of the following in the sample from the subject:

(i) an increased level of a somatic alteration (e.g., one or more somatic alterations) in a predetermined set of genes set forth in Table 1, e.g., compared to a reference level of a somatic alteration (e.g., one or more somatic alterations) in the predetermined set of genes set forth in Table 1;

(ii) the presence of a somatic alteration (e.g., one or more somatic alterations) in the NF1 gene;

(iii) an increased number of a somatic alteration (e.g., one or more somatic alterations) in the LRP1B gene, e.g., compared to a reference number of a somatic alteration (e.g., one or more somatic alterations) in the LRP1B gene; or (iv) an increased number of a C to T transition (e.g., one or more C to T transitions) in a predetermined set of genes set forth in Table 1, e.g., compared to a reference number of a C to T transition (e.g., one or more C to T transitions) in the predetermined set of genes set forth in Table 1.

Methods of Evaluating a Subject or a Cancer

In still another aspect, the invention features a method of evaluating a subject having a cancer, e.g., a melanoma. The method includes:

(a) acquiring a value of responder status to a therapy, e.g., a therapy comprising an inhibitor of PD-1 or PD-L1, for the subject, wherein said value of responder status comprises a measure of the mutation load in a sample, e.g., a melanoma sample or a sample derived from a melanoma, from the subject, and (b) identifying the subject as a responder (e.g., a complete responder or partial responder) or non-responder to the therapy, wherein a value of responder status equal to or greater than a reference value of responder status indicates that said subject is, or is likely to be, a responder, or said subject will respond, or will likely respond, to the therapy; or wherein a value of responder status less than a reference value of responder status indicates that said subject is, or is likely to be, a non-responder, or said subject will not respond, or will likely not respond, to the therapy.

In certain embodiments, the measure of the mutation load comprises a determination of one, two, three or all of the following in the sample from the subject:

(i) the level of a somatic alteration (e.g., one or more somatic alterations) in a predetermined set of genes set forth in Table 1;

(ii) the presence or absence of a somatic alteration (e.g., one or more somatic alterations) in an NF1 gene;

(iii) the number of a somatic alteration (e.g., one or more somatic alterations) in an LRP1B gene; or (iv) the number of a C to T transition (one or more C to T transitions) in a predetermined set of genes set forth in Table 1.

In certain embodiments, the therapy, e.g., the therapy comprising the inhibitor of PD-1 or PD-L1, is administered to the subject, responsive to one, two, three or all of the following in the sample from the subject:

(i) an increased level of a somatic alteration (e.g., one or more somatic alterations) in a predetermined set of genes set forth in Table 1, e.g., compared to a reference level of a somatic alteration (e.g., one or more somatic alterations) in the predetermined set of genes set forth in Table 1;

(ii) the presence of a somatic alteration (e.g., one or more somatic alterations) in the NF1 gene;

(iii) an increased number of a somatic alteration (e.g., one or more somatic alterations) in the LRP1B gene, e.g., compared to a reference number of a somatic alteration (e.g., one or more somatic alterations) in the LRP1B gene; or (iv) an increased number of a C to T transition (e.g., one or more C to T transitions) in a predetermined set of genes set forth in Table 1, e.g., compared to a reference number of a C to T transition (e.g., one or more C to T transitions) in the predetermined set of genes set forth in Table 1.

In certain embodiments, the method further comprises sequencing a T cell receptor (TCR) gene (e.g., one or more TCR genes). In certain embodiments, the method further comprises determining the clonality of a TCR gene.

In a related aspect, a method of evaluating a patient or patient population is provided. The method includes: identifying, selecting, or obtaining information or knowledge that the patient or patient population has participated in a clinical trial, acquiring a value of responder status to a therapy, e.g., a therapy comprising an inhibitor of PD-1 or PD-L1, for the patient or patient population, and identifying the patient or patient population as a responder (e.g., a complete responder or partial responder) or non-responder to the therapy, or whether the patient or patient population will respond, or will likely respond, to the therapy, as described herein.

In another aspect, the invention features a method of evaluating a cancer, e.g., a melanoma, in a subject. The method includes:

(a) acquiring a value of responder status to a therapy, e.g., a therapy comprising an inhibitor of PD-1 or PD-L1, for the subject, wherein said value of responder status comprises a measure of the mutation load in a sample, e.g., a melanoma sample or a sample derived from a melanoma, from the subject, and (b) determining the responsiveness of the cancer to the therapy, wherein a value of responder status equal to or greater than a reference value of responder status indicates that said cancer will respond, or will likely respond, to the therapy; or wherein a value of responder status less than a reference value of responder status indicates that said cancer will not respond, or will likely not respond, to the therapy.

In certain embodiments, the measure of the mutation load comprises a determination of one, two, three or all of the following in the sample from the subject:

(i) the level of a somatic alteration (e.g., one or more somatic alterations) in a predetermined set of genes set forth in Table 1;

(ii) the presence or absence of a somatic alteration (e.g., one or more somatic alterations) in an NF1 gene;

(iii) the number of a somatic alteration (e.g., one or more somatic alterations) in an LRP1B gene; or (iv) the number of a C to T transition (one or more C to T transitions) in a predetermined set of genes set forth in Table 1.

In certain embodiments, the therapy is administered to the subject, responsive to one, two, three or all of the following in the sample from the subject:

(i) an increased level of a somatic alteration (e.g., one or more somatic alterations) in a predetermined set of genes set forth in Table 1, e.g., compared to a reference level of a somatic alteration (e.g., one or more somatic alterations) in the predetermined set of genes set forth in Table 1;

(ii) the presence of a somatic alteration (e.g., one or more somatic alterations) in the NF1 gene;

(iii) an increased number of a somatic alteration (e.g., one or more somatic alterations) in the LRP1B gene, e.g., compared to a reference number of a somatic alteration (e.g., one or more somatic alterations) in the LRP1B gene; or (iv) an increased number of a C to T transition (e.g., one or more C to T transitions) in a predetermined set of genes set forth in Table 1, e.g., compared to a reference number of a C to T transition (e.g., one or more C to T transitions) in the predetermined set of genes set forth in Table 1.

In certain embodiments, the method further comprises sequencing a T cell receptor (TCR) gene (e.g., one or more TCR genes). In certain embodiments, the method further comprises determining the clonality of a TCR gene.

Additional aspects or embodiments of the invention include one or more of the following.

Responder Status and Mutation Load

The invention described herein can include, e.g., acquiring a value of responder status to a therapy, e.g., a therapy comprising an inhibitor of PD-1 or PD-L1, for a subject having a cancer, e.g., a melanoma.

In certain embodiments, the therapy is administered to, or selected for, the subject, responsive to an increased value of responder status, e.g., compared to a reference value of responder status. In certain embodiments, the reference value of responder status is a value of responder status for a non-responder to the therapy.

In certain embodiments, the value of responder status comprises a measure of the mutation load in a sample, e.g., a melanoma sample or a sample derived from a melanoma, from the subject.

In certain embodiments, the therapy is administered to, or selected for, the subject, responsive to an increased level of mutation load in the sample from the subject, compared to a reference level of mutation load. In certain embodiments, the reference level of mutation load is the level of mutation load in a sample from a non-responder to the therapy.

In certain embodiments, the subject is identified as a responder to the therapy, when the melanoma sample from the subject has one, two, three or all of the following:

(i) an increased level of a somatic alteration in a predetermined set of genes set forth in Table 1, compared to a reference level of a somatic alteration in the predetermined set of genes set forth in Table 1;

(ii) the presence of a somatic alteration in the NF1 gene;

(iii) an increased number of a somatic alteration in the LRP1B gene, compared to a reference number of a somatic alteration in the LRP1B gene; or (iv) an increased number of a C to T transition in a predetermined set of genes set forth in Table 1, compared to a reference number of a C to T transition in the predetermined set of genes set forth in Table 1.

In certain embodiments, the subject is identified as a non-responder to the therapy, when the sample from the subject has one, two, three or all of the following:

(i) a decreased or unchanged level of a somatic alteration in a predetermined set of genes set forth in Table 1, compared to a reference level of a somatic alteration in the predetermined set of genes set forth in Table 1;

(ii) the absence of a somatic alteration in the NF1 gene;

(iii) a similar, same or decreased number of a somatic alteration in the LRP1B gene, compared to a reference number of a somatic alteration in the LRP1B gene; or (iv) a similar, same or decreased number of a C to T transition in a predetermined set of genes set forth in Table 1, compared to a reference number of a C to T transition in the predetermined set of genes set forth in Table 1.

In certain embodiments, the predetermined set of genes comprise at least about 50 or more, about 100 or more, about 150 or more, about 200 or more, about 250 or more, about 300 or more, or all of the genes set forth in Table 1.

In certain embodiments, the reference level of a somatic alteration in the predetermined set of genes set forth in Table 1 is the level of a somatic alteration in the predetermined set of genes set forth in Table 1 in a sample from a non-responder to the therapy.

In certain embodiments, the reference number of a somatic alteration in the LRP1B gene is the number of a somatic alteration in the LRP1B gene in a sample from a non-responder to the therapy.

In certain embodiments, the reference number of a C to T transition in a predetermined set of genes set forth in Table 1 is the number of a C to T transition in a sample from a non-responder to the therapy.

In certain embodiments, the level of a somatic alteration in the predetermined set of genes set forth in Table 1 is determined by a method comprising sequencing the predetermined set of genes set forth in Table 1, e.g., sequencing the coding regions of the predetermined set of genes set forth in Table 1. In certain embodiments, the presence or absence of a somatic alteration in the NF1 gene is determined by a method comprising sequencing the NF1 gene, e.g., the coding region of the NF1 gene. In certain embodiments, the number of a somatic alteration in the LRP1B gene is determined by a method comprising sequencing the LRP1B gene, e.g., the coding region of the LRP1B gene. In certain embodiments, the number of a C to T transition in the predetermined set of genes set forth in Table 1 is determined by a method comprising sequencing a predetermined set of genes set forth in Table 1.

In certain embodiments, the method further comprises, responsive to measure of the mutation load, performing one, two, three or all of the following:

(a) administering an altered dose of the therapy to the subject;

(b) altering a schedule or time course of the therapy for the subject;

(c) administering, e.g., to a non-responder or a partial responder, an additional agent in combination with the therapy; or (d) prognosticating a time course in the progression of the cancer in the subject.

In certain embodiments, the method further includes acquiring, e.g., directly or indirectly, a sample (e.g., a melanoma sample or a sample derived from a melanoma) from the subject and evaluating the sample for the mutation load or an alteration, as described herein.

Somatic Alterations in a Predetermined Set of Genes

A therapy described herein (e.g., a therapy comprising an inhibitor of PD-1 or PD-L1) can be administered to, or selected for, a subject having a cancer (e.g., a melanoma), e.g., responsive to an increased level of a somatic alteration (e.g., one or more somatic alterations) in a predetermined set of genes set forth in Table 1.

In certain embodiments, the determination of the level of a somatic alteration in the predetermined set of genes set forth in Table 1 comprises a determination of the level of a somatic alteration in about 25 or more, e.g., about 50 or more, about 100 or more, about 150 or more, about 200 or more, about 250 or more, about 300 or more, or all genes set forth in Table 1.

In certain embodiments, the determination of the level of a somatic alteration in the predetermined set of genes set forth in Table 1 comprises a determination of the number of a somatic alteration per a preselected unit, e.g., per megabase in the coding regions of the predetermined set of genes, e.g., in the coding regions of the predetermined set of genes sequenced.

In certain embodiments, the therapy is administered to, or selected for, the subject, responsive an increased level of a somatic alteration in the predetermined set of genes set forth in Table 1, e.g., at least about 2-fold, at least about 3-fold, at least about 5-fold, at least about 10-fold, at least about 15-fold, at least about 20-fold, at least about 30-fold, at least about 40-fold, or at least about 50-fold increase, compared to the reference level of a somatic alteration in the predetermined set of genes set forth in Table 1.

In certain embodiments, the therapy is administered to, or selected for, the subject, responsive to a determination that the number of somatic alterations in the predetermined set of genes set forth in Table 1 is about 3.3 or more, e.g., about 5 or more, about 10 or more, about 15 or more, about 20 or more, about 25 or more, about 30 or more, about 35 or more, about 40 or more, about 45 or more, or about 50 or more, somatic alterations per megabase in the coding regions of the predetermined set of genes.

In certain embodiments, the therapy is administered to, or selected for, the subject, responsive to a determination that the number of somatic alterations in the predetermined set of genes set forth in Table 1 is about 23.1 more, e.g., about 25 or more, about 30 or more, about 35 or more, about 40 or more, about 45 or more, or about 50 or more, somatic alterations per megabase in the coding regions of the predetermined set of genes.

In certain embodiments, the therapy is administered to, or selected for, the subject, responsive to a determination that the number of somatic alterations in the predetermined set of genes set forth in Table 1 is between about 3.3 and about 23.1, e.g., between about 5 and about 23, between about 10 and about 23, or between about 15 and about 23, somatic alterations per megabase in the coding regions of the predetermined set of genes.

In certain embodiments, an increased level of a somatic alteration in the predetermined set of genes set forth in Table 1, e.g., at least about 2-fold, at least about 3-fold, at least about 5-fold, at least about 10-fold, at least about 15-fold, at least about 20-fold, at least about 30-fold, at least about 40-fold, or at least about 50-fold increase, compared to the reference level of a somatic alteration in the predetermined set of genes set forth in Table 1, indicates that the subject is, or is likely to be, a responder, or will respond, or will likely respond, to the therapy.

In certain embodiments, a similar, same or decreased level of somatic alterations in the predetermined set of genes set forth in Table 1, compared to the reference level of somatic alterations in the predetermined set of genes set forth in Table 1, indicates that the subject is, or is likely to be a non-responder, or will not respond, or will likely not respond, to the therapy.

In certain embodiments, a determination that the number of somatic alterations in the predetermined set of genes set forth in Table 1 is about 3.3 or more, e.g., about 5 or more, about 10 or more, about 15 or more, about 20 or more, about 25 or more, about 30 or more, about 35 or more, about 40 or more, about 45 or more, or about 50 or more, somatic alterations per megabase in the coding regions of the predetermined set of genes set forth in Table 1, indicates that the subject is, or is likely to be, a responder, e.g., a complete responder or partial responder, or will respond, or will likely respond, to the therapy.

In certain embodiments, a determination that the number of a somatic alteration in the predetermined set of genes set forth in Table 1 is less than about 3.3 somatic alterations per megabase in the coding regions of the predetermined set of genes set forth in Table 1 indicates that the subject is, or is likely to be, a non-responder, or will not respond, or will likely not respond, to the therapy.

In certain embodiments, a determination that the number of somatic alterations in the predetermined set of genes set forth in Table 1 is about 23.1 more, e.g., about 25 or more, about 30 or more, about 35 or more, about 40 or more, about 45 or more, or about 50 or more, somatic alterations per megabase in the coding regions of the predetermined set of genes set forth in Table 1, indicates that the subject is, or is likely to be, a responder, e.g., a complete responder, or will respond, or will likely respond, to the therapy.

In certain embodiments, a determination that the number of a somatic alteration in the predetermined set of genes set forth in Table 1 is less than about 23.1 somatic alterations per megabase in the coding regions of the predetermined set of genes set forth in Table 1 indicates that the subject is, or is likely to be, a partial responder or non-responder (or will partially respond or will not respond, or will likely partially respond, or will likely not respond) to the therapy.

In certain embodiments, a determination that the number of somatic alterations in the predetermined set of genes set forth in Table 1 is between about 3.3 and about 23.1, e.g., between about 5 and about 23, between about 10 and about 23, or between about 15 and about 23, somatic alterations per megabase in the coding regions of the predetermined set of genes set forth in Table 1, indicates that the subject is, or is likely to be, a partial responder (or will partially respond, or will likely partially respond) to the therapy.

Alterations in an NF1 Gene

A therapy described herein (e.g., a therapy comprising an inhibitor of PD-1 or PD-L1) can be administered to, or selected for, a subject having a cancer (e.g., a melanoma), e.g., responsive to a determination of the number of a somatic alteration in an NF1 gene (e.g., the coding region of an NF1 gene).

In certain embodiments, the therapy is administered to, or selected for, the subject, responsive to a determination that a somatic alteration is present in the NF1 gene (e.g., the coding region of the NF1 gene).

In certain embodiments, the presence of a somatic alteration in the coding region of the NF1 gene indicates that the subject is, or is likely to be, a responder to the therapy.

In certain embodiments, the therapy is administered to, or selected for, the subject, responsive to a determination that: (a) a somatic alteration is present in the coding region of the NF1 gene; and (b) the level of somatic alteration in the predetermined set of genes set forth in Table 1 is about 23.1 or more, e.g., about 25 or more, about 30 or more, about 35 or more, about 38.5 or more, about 40 or more, about 45 or more, or about 50 or more somatic alterations per megabase in the coding regions of the predetermined set of genes set forth in Table 1.

In certain embodiments, the therapy is administered to, or selected for, the subject, responsive to a determination of: (a) a presence of a somatic alteration in the coding region of the NF1 gene; and (b) an increased, e.g., increased at least about 2-fold, at least about 3-fold, at least about 5-fold, or at least about 10-fold, level of somatic alteration in the predetermined set of genes set forth in Table 1, compared to a level of somatic alteration in the predetermined set of genes set forth in Table 1 in a sample (e.g., a melanoma sample or a sample derived from melanoma) that comprises a somatic alteration in an BRAF gene, a somatic alteration in an NRAS gene, or is triple WT (wild type) for BRAF, NRAS and NF1 genes.

Alterations in an LRP1B Gene

A therapy described herein (e.g., a therapy comprising an inhibitor of PD-1 or PD-L1) can be administered to, or selected for, a subject having a cancer (e.g., a melanoma), e.g., responsive to a determination of a presence of a somatic alteration in an LRP1B gene (e.g., in the coding region of the LRP1B gene).

In certain embodiments, the therapy is administered to, or selected for, the subject, responsive to a determination of a presence of about 1 or more, about 2 or more, about 3 or more, about 4 or more, or about 5 or more, somatic alterations in the LRP1B gene (e.g., the coding region of the LRP1B gene).

In certain embodiments, the presence of about 1 or more, about 2 or more, about 3 or more, about 4 or more, or about 5 or more, somatic alterations in the coding region of the LRP1B gene indicates that the subject is, or is likely, a responder, or will respond or will likely respond, to the therapy.

In certain embodiments, the therapy is administered to, or selected for, the subject, responsive to a determination of an increased number of somatic alterations in the coding region of the LRP1B gene, e.g., increased by at least about 2-fold, at least about 2.5-fold, at least about 2.8-fold, at least about 3-fold, at least about 3.5-fold, at least about 4-fold, or at least about 5-fold, compared to a reference number of a somatic alteration in the coding region of the LRP1B gene.

In certain embodiments, the reference number of a somatic alteration in the coding region of the LRP1B gene is the number of a somatic alteration in the coding region of the LRP1B gene in a sample (e.g., a melanoma sample or a sample derived from a melanoma) from a non-responder to the therapy.

In certain embodiments, the reference number of alterations in the coding region of the LRP1B gene is 0 or 1 somatic alteration.

C to T Transitions

A therapy described herein (e.g., a therapy comprising an inhibitor of PD-1 or PD-L1) can be administered to, or selected for, a subject having a cancer (e.g., a melanoma), e.g., responsive to a determination of the number of a C to T transition in a predetermined set of genes, e.g., a predetermined set of genes set forth in Table 1.

In certain embodiments, the therapy is administered to, or selected for, the subject, responsive to a determination of a presence of about 20 or more, about 30 or more, about 40 or more, or about 50 or more C to T transitions in a predetermined set of genes set forth in Table 1.

In certain embodiments, a determination of a presence of about 20 or more, about 24 or more, about 30 or more, about 40 or more, or about 50 or more C to T transitions in a predetermined set of genes set forth in Table 1, indicates that the subject is, or is likely to be, a responder to the therapy.

In certain embodiments, the therapy is administered to, or selected for, the subject, responsive to a determination of an increased number of C to T transitions in a predetermined set of genes set forth in Table 1, e.g., increased by at least about 8-fold, at least about 10-fold, at least about 12-fold, at least about 15-fold, or at least about 20-fold, compared to the reference number of C to T transitions in the predetermined set of genes set forth in Table 1.

In certain embodiments, the reference number of a C to T transition is the number of C to T transitions in a sample (e.g., a melanoma sample or a sample derived from a melanoma) from a non-responder to the therapy.

In certain embodiments, the reference number of a C to T transition is about 2 C to T transitions in a predetermined set of genes set forth in Table 1.

Type of Alterations

Various types of alterations, e.g., somatic alterations, can be used to measure the mutation load in a sample, as described herein.

In certain embodiments, the alterations, include one or more of the following: a silent mutation (e.g., a synonymous alteration), a somatic alteration that has not been identified as being associated with a cancer phenotype, a passenger mutation (e.g., an alteration that has no detectable effect on the fitness of a clone), a variant of unknown significance (VUS) (e.g., an alteration, the pathogenicity of which can neither be confirmed nor ruled out), a point mutation, a coding short variant (e.g., a base substitution or an indel), a non-synonymous single nucleotide variant (SNV), or a splice variant.

Alternatively, or in combination, in some embodiments, the alterations do not include one or more of the following: a rearrangement (e.g., a translocation), a functional alteration, or a germline mutation.

In certain embodiments, the somatic alteration is a silent mutation, e.g., a synonymous alteration. In certain embodiments, the somatic alteration has not been identified as being associated with a cancer phenotype. In certain embodiments, the somatic alteration is a passenger mutation, e.g., an alteration that has no detectable effect on the fitness of a clone. In certain embodiments, the somatic alteration is a variant of unknown significance (VUS), e.g., an alteration, the pathogenicity of which can neither be confirmed nor ruled out. In certain embodiments, the somatic alteration is a point mutation. In certain embodiments, the somatic alteration is other than a rearrangement, e.g., other than a translocation. In certain embodiments, the somatic alteration is a coding short variant, e.g., a base substitution or an indel. In certain embodiments, the somatic alteration is a non-synonymous single nucleotide variant (SNV). In certain embodiments, the somatic alteration is a splice variant. In certain embodiments, the somatic alteration is not a functional alteration.

In certain embodiments, the alteration is not a germline mutation. In other embodiments, the somatic alteration is not identical or similar to (e.g., is distinguishable from) a germline mutation. In certain embodiments, an increased level of a somatic alteration is an increased level of one or more classes or types of a somatic alteration (e.g., a rearrangement, a point mutation, an indel, or any combination thereof). In certain embodiments, an increased level of a somatic alteration is an increased level of one class or type of a somatic alteration (e.g., a rearrangement only, a point mutation only, or an indel only). In certain embodiments, an increased level of a somatic alteration is an increased level of a somatic alteration at a preselected position (e.g., an alteration described herein, e.g., a V600 alteration in BRAF). In certain embodiments, an increased level of a somatic alteration is an increased level of a preselected somatic alteration (e.g., an alteration described herein, e.g., a V600 alteration in BRAF (e.g., a V600K alteration in BRAF)).

Therapeutic Agents and Modalities

A subject having a cancer, as described herein, can be treated with a therapy, e.g., an immunotherapy, e.g., a therapy comprising an inhibitor of PD-1 or PD-L1.

In certain embodiments, the inhibitor of PD-1 is an anti-PD-1 antibody. In certain embodiments, the inhibitor of PD-1 is chosen from nivolumab (ONO-4538, BMS-936558, or MDX1106), pembrolizumab (MK-3475 or lambrolizumab), pidilizumab (CT-011), MEDI00680 (AMP-514), PDR001, REGN2810, BGB-108, BGB-A317, SHR-1210 (HR-301210, SHR1210, or SHR-1210), PF-06801591, or AMP-224.

In certain embodiments, the inhibitor of PD-L1 is an anti-PD-L1 antibody. In certain embodiments, the inhibitor of PD-L1 is chosen from atezolizumab (MPDL3280A, RG7446, or RO5541267), YW243.55.S70, MDX-1105, durvalumab (MEDI4736), or avelumab (MSB0010718C).

In certain embodiments, the inhibitor of PD-1 or PD-L1 is a PD-1 receptor, e.g., a PD-1 receptor Fc fusion, or a PD-L1 receptor, e.g., a PD-L1 receptor Fc fusion.

In certain embodiments, the subject is receiving, or has received, a different therapy comprising a therapeutic agent or modality other than an inhibitor of PD-1 or PD-L1.

In certain embodiments, the different therapy is discontinued, responsive to the determination of one, two, three or all of the following:

(i) an increased level of a somatic alteration in a predetermined set of genes set forth in Table 1, compared to a reference level of a somatic alteration in the predetermined set of genes set forth in Table 1;

(ii) the presence of a somatic alteration in an NF1 gene;

(iii) an increased number of a somatic alteration in an LRP1B gene, compared to a reference level of a somatic alteration in an LRP1B gene; or (iv) an increased number of a C to T transition in a predetermined set of genes set forth in Table 1, compared to a reference level of a C to T transition in the predetermined set of genes set forth in Table 1.

In certain embodiments, the therapy is administered after cessation of the different therapy. In other embodiments, the therapy is administered in combination with the different therapy.

In certain embodiments, the different therapy is chosen from a chemotherapy, a radiation therapy, an immunotherapy, an immunoradiotherapy, an oncolytic virotherapy, a surgical procedure, or any combination thereof.

In certain embodiments, the different therapy comprises one or more of: dacarbazine, temozolomide, interleukin-2 (IL-2), an interferon, ipilimumab, a BRAF inhibitor, a MEK inhibitor, talimogene laherparepvec, an adoptive cell transfer, or any combination thereof.

In certain embodiments, the interferon is a recombinant interferon alfa-2b or a peginterferon alfa-2b. In certain embodiments, the BRAF inhibitor is vemurafenib or dabrafenib. In certain embodiments, the MEK inhibitor is cobimetinib or trametinib. In certain embodiments, the adoptive cell transfer comprises modified T cells or modified dendritic cells.

In certain embodiments, the subject is receiving, or has received, an immunotherapy, e.g., a therapy comprising an inhibitor of PD-1 or PD-L1. In certain embodiments, the subject is not receiving, or has not received, an immunotherapy, e.g., a therapy comprising an inhibitor of PD-1 or PD-L1.

Melanoma

The invention described herein can be used to treat a cancer, e.g., a melanoma, or to evaluate a subject having a cancer, e.g., melanoma.

The melanoma can be any stage or risk group of melanoma defined according to any suitable melanoma classification system known to those of skill in the art.

In some embodiments, the melanoma is any one of a stage 0, stage IA, stage IB, stage IIA, stage IIB, stage IIC, stage III, or stage IV melanoma, e.g., any one of a stage 0, stage IA, stage IB, stage IIA, stage IIB, stage IIC, stage III, or stage IV melanoma, as defined by the American Joint Committee on Cancer (AJCC) melanoma staging and classification system. In one embodiment, the melonoma is staged or classified according to Tables 2A and 2B as provided herein.

In some embodiments, the melanoma is any one of a melanoma in situ (e.g., a stage 0 melanoma), a localized melanoma (e.g., a stage I or II melanoma), a regional metastastic melanoma (e.g., a stage III melanoma), or a distant metastatic melanoma (e.g., a stage IV melanoma), e.g., as described by Balch et al. *J Clin Oncol.* 2009; 27(36): 6199-6206). In some embodiments, the melanoma is an advanced melanoma, e.g., a stage III or IV melanoma.

In other embodiments, the melanoma is any one of a level 1, level 2, level 3, level 4, or level 5 melanoma, e.g., any one of a level 1 (e.g., melanoma confined to the epidermis (melanoma in situ)), level 2 (e.g., invasion into the papillary dermis), level 3 (e.g., invasion to the junction of the papillary and reticular dermis), level 4 (e.g., invasion into the reticular dermis), or level 5 (e.g., invasion into the subcutaneous fat) melanoma, according to Clark's level (Weedon, *Skin pathology.* 2nd Edition. 2002. Sydney: Churchill-Livingstone).

In some embodiments, the melanoma is any one of a stage I, stage II, stage III, stage IV, or stage IV melanoma, e.g., any one of a stage I (e.g., depth less or equal to 0.75 mm), stage II (e.g., depth 0.76 mm-1.50 mm), stage III (e.g., depth 1.51 mm-2.25 mm), stage IV (e.g., depth 2.26 mm-3.0 mm), or stage V (e.g., depth greater than 3.0 mm) melanoma, according to Breslow's depth (Breslow (1970) Annals of Surgery 172 (5): 902-908).

In certain embodiments, the melanoma is an advanced melanoma. In some embodiments, the advanced melanoma is a stage III or a stage IV melanoma, e.g., according to the AJCC staging and classification system. In one embodiment, the advanced melanoma is a stage III or stage IV melanoma according to the staging and classification described in Tables 2A and 2B. In one embodiment, the advanced melanoma is a stage III melanoma, e.g., a stage III melanoma as described herein. In another embodiment, the advanced melanoma is a stage IV melanoma, e.g., a stage IV melanoma as described herein.

In certain embodiments, the melanoma is a metastatic melanoma. In some embodiments, the metastatic melanoma is a stage III or a stage IV melanoma, e.g., according to the AJCC staging and classification system. In one embodiment, the metastatic melanoma is a stage III or stage IV melanoma according to the staging and classification described in Tables 2A and 2B. In one embodiment, the metastatic melanoma is a stage III melanoma, e.g., a stage III melanoma as described herein. In another embodiment, the metastatic melanoma is a stage IV melanoma, e.g., a stage IV melanoma as described herein.

In other embodiments, the melanoma, e.g., the advanced melanoma, comprises, or is identified or determined as having, an alteration in one or more of the genes described herein, e.g., one or more of the genes set forth in Table 1, e.g., an alteration as described herein. In certain embodiments, the melanoma comprises, or is identified as having, an alteration in one or more of the genes chosen from NF1, LRP1B, BRAF, NRAS, TP53, MYC, APC/CTNNB1, IGF1R/HGF, PTEN, CDKN2A, CDK4, CDK6, and/or RB1.

In certain embodiments, the melanoma comprises, or is identified as having, an alteration in an NF1 gene. In certain embodiments, the melanoma comprises, or is identified as having, an alteration in an LRP1B gene. In certain embodiments, the melanoma comprises, or is identified as having, an alteration in a BRAF gene. In certain embodiments, the melanoma comprises, or is identified as having, an alteration in an NRAS gene. In certain embodiments, the melanoma comprises, or is identified as having, an alteration in an NF1 gene and an alteration in an LRP1B gene. In certain embodiments, the melanoma comprises, or is identified as having, an alteration in an NF1 gene, but does not comprise, or is not identified as having, an alteration in a BRAF gene, an alteration in an NRAS gene, or both. In certain embodiments, the melanoma comprises, or is identified as having, an alteration in an LRP1B gene, but does not comprise, or is not identified as having, an alteration in a BRAF gene, an alteration in an NRAS gene, or both. In certain embodiments, the melanoma is identified as a triple wild-type (WT) melanoma, e.g., the melanoma does not comprise, or is not identified as having, any of an alteration in an NF1 gene, an alteration in a BRAF gene, and an alteration in an NRAS gene.

In certain embodiments, the alteration in the NF1 gene results in decreased activity of an NF1 gene product (e.g., an NF1 protein), compared to a wild-type activity of NF1. For example, the alteration can result in an alteration (e.g., a decrease) in a GTPase activator activity, a phosphatidylcholine binding activity, and/or a phosphatidylethanolamine binding activity of an NF1 protein. In one embodiment, the NF1 alteration is, or comprises, a mutation (e.g., a somatic mutation), e.g., a substitution (e.g., a base substitution), an insertion, or a deletion.

In certain embodiments, the alteration in the BRAF gene results in increased activity of a BRAF gene product (e.g., a BRAF protein), compared to a wild-type activity of BRAF. For example, the alteration can result in an alteration (e.g., an increase) in a kinase activity of a BRAF protein. In one embodiment, the BRAF alteration is, or comprises, a mutation (e.g., a somatic mutation), e.g., a substitution (e.g., a base substitution), an insertion, or a deletion. In certain embodiments, the alteration is a base substitution.

In certain embodiments, the alteration in BRAF is located at codon V600. In certain embodiments, the alteration in BRAF is a V600E alteration. In certain embodiments, the alteration in BRAF is a V600K alteration. In certain embodiments, the alteration in BRAF is a V600R alteration. In certain embodiments, the alteration in BRAF is a V600D alteration.

In certain embodiments, the alteration in BRAF is an alteration other than a V600 alteration. In certain embodiments, the alteration in BRAF is a K601 alteration. In certain embodiments, the alteration in BRAF is a K601E alteration. In certain embodiments, the alteration in BRAF is a G469 alteration. In certain embodiments, the alteration in BRAF is a G469E alteration. In certain embodiments, the alteration in BRAF is a D594 alteration. In certain embodiments, the alteration in BRAF is a D594G alteration. In certain embodiments, the alteration in BRAF is an L597 alteration. In certain embodiments, the alteration in BRAF is an L597S alteration. In certain embodiments, the alteration in BRAF is an S467 alteration. In certain embodiments, the alteration in BRAF is an S467L alteration.

Subjects

In certain embodiments, the subject has a melanoma, e.g., an advanced melanoma, as described herein, wherein said melanoma comprises an alteration in e.g., one or more of the genes set forth in Table 1, e.g., an alteration as described herein. In certain embodiments, the melanoma comprises, or is identified as having, an alteration in one or more of the genes chosen from NF1, LRP1B, BRAF, NRAS, TP53, MYC, APC/CTNNB1, IGF1R/HGF, PTEN, CDKN2A, CDK4, CDK6, and/or RB1. In other embodiments, the subject is identified, or has been previously identified, as having a melanoma, e.g., an advanced melanoma, comprising a C to T transition.

The melanoma can be at any stage of disease, e.g., any stage described herein, including but not limited to, advanced, recurrent, relapsed, or refractory. Cancer staging systems for melanomas include, e.g., the American Joint Committee on Cancer (AJCC) melanoma staging and classification system. For example, the melanoma can be any one of a stage 0, stage IA, stage IB, stage IIA, stage IIB, stage IIC, stage III, or stage IV melanoma, e.g., any one of a stage 0, stage IA, stage IB, stage IIA, stage IIB, stage IIC, stage III, or stage IV melanoma, e.g., according to Tables 2A and 2B as provided herein.

In one embodiment, the subject is a human, e.g., a human patient having a melanoma, e.g., an advanced melanoma, as described herein.

In one embodiment, the subject is undergoing or has undergone treatment with a different (e.g., non-PD-1 and/or non-PD-L1) therapeutic agent or therapeutic modality. In one embodiment, the different therapeutic agent or therapeutic modality is a chemotherapy, a radiation therapy, an immunotherapy, an immunoradiotherapy, an oncolytic virotherapy, a surgical procedure, or any combination thereof. In one embodiment, the different therapeutic agent or therapeutic modality comprises one or more of: dacarbazine, temozolomide, interleukin-2 (IL-2), interferon (e.g., recombinant interferon alfa-2b or peginterferon alfa-2b), ipilimumab, a BRAF inhibitor (e.g., vemurafenib or dabrafenib), a MEK inhibitor (e.g., cobimetinib or trametinib), talimogene laherparepvec, and/or adoptive cell transfer (e.g., modified T cells or dendritic cells).

In one embodiment, responsive to the determination of the mutation load and/or the presence of an alteration described herein, the different (e.g., non-PD-1 and/or non-PD-L1 checkpoint) therapeutic agent or therapeutic modality is discontinued. In yet other embodiments, the subject has been identified as being likely or unlikely to respond to the different therapeutic agent or therapeutic modality.

In certain embodiments, the subject is a melanoma patient who has participated in a clinical trial for an inhibitor of PD-1 or PD-L1. In certain embodiments, the subject is a melanoma patient who has participated in a clinical trial for a different (e.g., non-PD-1 and/or non-PD-L1) therapeutic agent or therapeutic modality.

In one embodiment, the subject is 60 years of age, or older. In another embodiment, the subject is between 45 and 60 years of age. In yet another embodiment, the subject is 45 years of age, or younger. In still another embodiment, the subject is 30 years of age, or younger. In one embodiment, the subject is 45 years of age, or older, and is a male. In another embodiment, the subject is 45 years of age, or younger, and is a female. In one embodiment, the subject is a Caucasian. In one embodiment, the subject has a family history of melanoma.

Systems

In an aspect, the invention features a system for evaluating a subject having a cancer, e.g., a melanoma. The system includes:

at least one processor operatively connected to a memory, the at least one processor when executing is configured to:

(a) acquire a value of responder status to a therapy (e.g., a therapy comprising an inhibitor of PD-1 or PD-L1) for the subject, wherein said value of responder status comprises a measure of the mutation load in a sample (e.g., a melanoma sample or a sample from a melanoma) from the subject, and (b) identify the subject as a responder (e.g., a complete responder or partial responder) or non-responder to the therapy, wherein a value of responder status equal to or greater than a reference value of responder status indicates that said subject is, or is likely to be, a responder, or said subject will respond, or will likely respond, to the therapy; or wherein a value of responder status less than a reference value of responder status indicates that said subject is, or is likely to be, a non-responder, or said subject will not respond, or will likely not respond, to the therapy.

In certain embodiments, the measure of the mutation load comprises a determination of one, two, three or all of the following in the sample from the subject:

(i) the level of a somatic alteration (e.g., one or more somatic alterations) in a predetermined set of genes set forth in Table 1;

(ii) the presence of a somatic alteration (e.g., one or more somatic alterations) in an NF1 gene;

(iii) the number of a somatic alteration (e.g., one or more somatic alterations) in an LRP1B gene; or (iv) the number of a C to T transition (e.g., one or more C to T transitions) in a predetermined set of genes set forth in Table 1.

In certain embodiments, the therapy is administered to, or selected for, the subject, responsive to one, two, three or all of the following in the melanoma sample from the subject:

(i) an increased level of a somatic alteration (e.g., one or more somatic alterations) in a predetermined set of genes set forth in Table 1, compared to a reference level of a somatic alteration (e.g., one or more somatic alterations) in the predetermined set of genes set forth in Table 1;

(ii) the presence of a somatic alteration (e.g., one or more somatic alterations) in the NF1 gene;

(iii) an increased number of a somatic alteration (e.g., one or more somatic alterations) in the LRP1B gene, compared to a reference level of a somatic alteration (e.g., one or more somatic alterations) in the LRP1B gene; or (iv) an increased number of a C to T transition (e.g., one or more C to T transitions) in a predetermined set of genes set forth in Table 1, compared to a reference level of a C to T transition (e.g., one or more C to T transitions) in the predetermined set of genes set forth in Table 1.

Kits, Preparations of Nucleic Acids, and Reaction Mixtures

In an aspect, the invention features a kit. The kit includes:

(a) one or more detection reagents, capable of detecting one or more of:
 (i) a somatic alteration (e.g., one or more somatic alterations) in a predetermined set of genes set forth in Table 1,
 (ii) a somatic alteration (e.g., one or more somatic alterations) in an NF1 gene,
 (iii) a somatic alteration (e.g., one or more somatic alterations) in an LRP1B gene,
 (iv) a C to T transition (e.g., one or more C to T transitions); and (b) instructions for use in determining the mutation load in a melanoma sample and/or in treating a melanoma in a subject, and In certain embodiments, the kit further comprises (c) an inhibitor of PD-1 or PD-L1, or a composition thereof.

In another aspect, the invention features a purified or isolated preparation of a nucleic acid derived from a sample, e.g., a melanoma sample or a sample derived from a melanoma. The preparation includes one or more of:

(i) a somatic alteration (e.g., one or more somatic alterations) in a predetermined set of genes set forth in Table 1, (ii) a somatic alteration (e.g., one or more somatic alterations) in an NF1 gene, (iii) a somatic alteration (e.g., one or more somatic alterations) in an LRP1B gene, (iv) a C to T transition (e.g., one or more C to T transitions).

In certain embodiments, the preparation is used to determine the mutation load of the melanoma sample, disposed in a sequencing device, or a sample holder for use in such a device.

In yet another aspect, the invention features a reaction mixture. The reaction mixture includes:

(a) one or more detection reagents, capable of detecting one or more of:
 (i) a somatic alteration (e.g., one or more somatic alterations) in a predetermined set of genes set forth in Table 1,
 (ii) a somatic alteration (e.g., one or more somatic alterations) in an NF1 gene,
 (iii) a somatic alteration (e.g., one or more somatic alterations) in an LRP1B gene, or
 (iv) a C to T transition (e.g., one or more C to T transitions); and (b) a nucleic acid derived from a sample (e.g., a melanoma sample or a sample derived from a melanoma) comprising one or more of:
 (i) a somatic alteration (e.g., one or more somatic alterations) in a predetermined set of genes set forth in Table 1,
 (ii) a somatic alteration (e.g., one or more somatic alterations) in an NF1 gene,
 (iii) a somatic alteration (e.g., one or more somatic alterations) in an LRP1B gene, or
 (iv) a C to T transition (e.g., one or more C to T transitions).

In certain embodiments, the reaction mixture is used to determine the mutation load of the sample, disposed in a sequencing device, or a sample holder for use in such a device.

In a related aspect, the invention features a method of making a reaction mixture. The method includes: combining one or more detection reagents, capable of detecting one or more of:

(i) a somatic alteration (e.g., one or more somatic alterations) in a predetermined set of genes set forth in Table 1, (ii) a somatic alteration (e.g., one or more somatic alterations) in an NF1 gene, (iii) a somatic alteration (e.g., one or more somatic alterations) in an LRP1B gene, or (iv) a C to T transition (e.g., one or more C to T transitions), with a nucleic acid derived from a melanoma sample comprising one or more of:

(i) a somatic alteration (e.g., one or more somatic alterations) in a predetermined set of genes set forth in Table 1, (ii) a somatic alteration (e.g., one or more somatic alterations) in an NF1 gene, (iii) a somatic alteration (e.g., one or more somatic alterations) in an LRP1B gene, or (iv) a C to T transition (e.g., one or more C to T transitions).

Unless otherwise defined, all technical and scientific terms used herein have the same meaning as commonly understood by one of ordinary skill in the art to which this invention belongs. Although methods and materials similar or equivalent to those described herein can be used in the practice or testing the invention, suitable methods and materials are described below. All publications, patent applications, patents, and other references mentioned herein are incorporated by reference in their entirety. In case of conflict, the present specification, including definitions, will control. In addition, the materials, methods, and the examples are illustrative only and not intended to be limiting.

The details of one or more embodiments featured in the invention are set forth in the accompanying drawings and the description below. Other features, objects, and advantages featured in the invention will be apparent from the description and drawings, and from the claims.

DETAILED DESCRIPTION

Figure 1A:
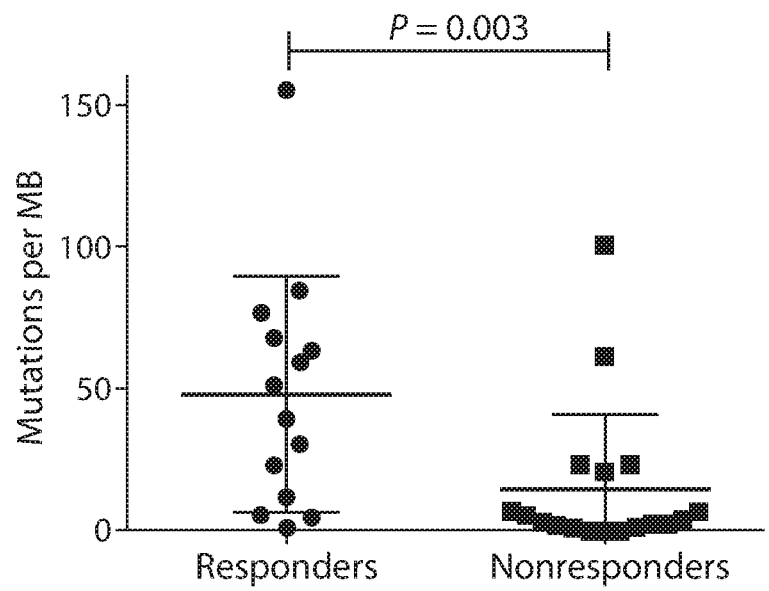
FIG. 1A depicts the mutational load in responders vs. non-responders in initial cohort.

The invention is based, at least in part, on the discovery that the number of mutations as detected in a several hundred gene genes, e.g., by a hybrid capture-based NGS platform, correlated with therapeutic benefit from a therapy that includes a PD-1 or a PD-L1. In certain embodiments, stratifying patients into groups, e.g., three groups, allowed for accurate prediction for most patients into "high" and "low" mutation load cohorts, thus providing a clinically-feasible marker of response to an anti-PD-1 and/or an anti-PD-L1 therapy in advanced melanoma and other cancers. In other embodiments, alterations in several genes (e.g. NF1, LRP1B) also correlated with total mutational burden and benefit from an anti-PD-1 or anti-PD-L1 therapy.

Without being bound by theory, the likelihood of generating immunogenic tumor neoantigens is believed to increase in a probabilistic fashion as mutations develop, increasing the likelihood of immune recognition (Gubin and Schreiber. *Science* 350:158-9, 2015). Assessing total mutational load, however, requires whole exome sequencing (WES). This approach necessitates specialized tissue processing, a matched normal specimen, and is largely performed as a research tool currently. Given the technical and informatics challenges of performing WES in clinical settings, surrogate methods of detecting mutational burden are needed. The methods including validated hybrid capture-based NGS platform described herein have several pragmatic advantages, including, for example, more clinically-feasible turnaround times (~2 weeks), standardized informatics pipelines, and more manageable costs. This approach has other advantages over markers such as PD-L1 expression, since it produces an objective (mutation load) rather than a subjective measure (immunohistochemical scoring) (Hansen and Siu. *JAMA Oncol* 2(1): 15-6, 2016). Further, this platform facilitates simultaneous detection of actionable alterations relevant for targeted therapies.

Identifying accurate predictive biomarkers for an anti-PD-1 or anti-PD-L1 therapy has several direct clinical applications. In melanoma, one could foresee that patients with high mutational load could receive, e.g., anti-PD-1 monotherapy, whereas those with intermediate/low mutational loads could be treated, e.g., with the more active (but more toxic) combination of nivolumab and ipilimumab (Larkin et al. *N Engl J Med*, 2015). Other cancers (e.g. NSCLC) may have a lower overall response rate to anti-PD-1 (Rizvi et al. *Lancet Oncol* 16:257-65, 2015; Garon et al. *N Engl J Med,* 2015). In these diseases, this approach could stratify patients between anti-PD-1 and other active agents such as cytotoxic chemotherapy. Further, identifying genomic and immune characteristics of "outliers" (e.g. high mutation load tumors that fail to respond) is a major need.

Accordingly, the invention provides, at least in part, methods of treating a subject having, or at risk of having, a cancer, e.g., a melanoma, by administering to the subject an effective amount of an agent (e.g., a therapeutic agent) that targets and/or inhibits the PD-1 pathway. In certain embodiments, the therapeutic agent is an inhibitor of PD-1 or PD-L1. In certain embodiments, the therapeutic agent, e.g., the inhibitor of PD-1 or PD-L1, is administered responsive to a value of responder status to the therapeutic agent. In certain embodiments, the value of responder status includes a measure of the mutation load in a cancer sample, e.g., a melanoma sample or a sample derived from a melanoma, from the subject. In certain embodiments, the measure of the mutation load includes a determination of the level of a somatic alteration in a predetermined set of genes disclosed herein, the presence of a somatic alteration in an NF1 gene, the number of a somatic alteration in an LRP1B gene, the number of a C to T transition in a predetermined set of genes disclosed herein, or any combination thereof. Methods and systems for evaluating a subject or for selecting a therapy, preparation of nucleic acids, kits, reaction mixtures, and methods of making a reaction mixture, are also disclosed.

Certain terms are defined below and throughout the specification.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise. The use of the term "and/or" in some places herein does not mean that uses of the term "or" are not interchangeable with the term "and/or" unless the context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or a fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sequence" as the term is used herein, refers to obtaining possession of a nucleotide sequence or amino acid sequence, by "directly acquiring" or "indirectly acquiring" the sequence. "Directly acquiring a sequence" means performing a process (e.g., performing a synthetic or analytical method) to obtain the sequence, such as performing a sequencing method (e.g., a Next Generation Sequencing (NGS) method). "Indirectly acquiring a sequence" refers to receiving information or knowledge of, or receiving, the sequence from another party or source (e.g., a third party laboratory that directly acquired the sequence). The sequence acquired need not be a full sequence, e.g., sequencing of at least one nucleotide, or obtaining information or knowledge that identifies a mutation disclosed herein as being present in a subject constitutes acquiring a sequence.

Directly acquiring a sequence includes performing a process that includes a physical change in a physical substance, e.g., a starting material, such as a tissue sample, e.g., a biopsy, or an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture; performing a chemical reaction that includes breaking; or forming a covalent or non-covalent bond. Directly acquiring a value includes performing a process that includes a physical change in a sample or another substance as described above.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

An "alteration" as used herein, of a gene or gene product (e.g., a gene or gene product set forth in Table 1, an NF1 gene or gene product, or an LRP1B gene or gene product) refers to the presence of a mutation or mutations within the gene or gene product, e.g., a mutation, which affects integrity, sequence, structure, amount or activity of the gene or gene product, as compared to the normal or wild-type gene. The alteration can be in amount, structure, and/or activity in a cancer tissue or cancer cell, as compared to its amount, structure, and/or activity, in a normal or healthy tissue or cell (e.g., a control), and is associated with a disease state, such as cancer. For example, a gene or gene product which is associated with cancer, or predictive of responsiveness to anti-cancer therapeutics, can have or result from an altered nucleotide sequence (e.g., a mutation), amino acid sequence, chromosomal translocation, intra-chromosomal inversion, copy number, expression level, protein level, protein activity, or epigenetic modification (e.g., methylation or acetylation status), or post-translational modification, in a cancer tissue or cancer cell, as compared to a normal, healthy tissue or cell. Exemplary mutations include, but are not limited to, point mutations (e.g., silent, missense, or nonsense), deletions, insertions, inversions, duplications, amplifications, translocations, inter- and intra-chromosomal rearrangements. Mutations can be present in the coding or non-coding region of the gene. In certain embodiments, the alterations are associated (or not associated) with a phenotype, e.g., a cancerous phenotype (e.g., one or more of cancer risk, cancer progression, cancer treatment, or resistance to cancer treatment). In certain embodiments, the term "alteration" and "mutation" are used interchangeably herein.

As used herein, "functional alteration" includes an alteration that, compared with a reference sequence, e.g., a wild-type or unmutated sequence, has an effect on cell division, growth or survival, e.g., promotes cell division, growth or survival. In certain embodiments, the functional alteration is identified as such by inclusion in a database of functional alterations, e.g., the COSMIC database (cancer.sanger.ac.uk/cosmic; Forbes et al. *Nucl. Acids Res.* 2015; 43 (D1): D805-D811). In certain embodiments, the functional alteration is an alteration with known functional status, e.g., occurring as a known somatic alteration in the COSMIC database. In other embodiments, the functional alteration is an alteration with a likely functional status, e.g., a truncation in a tumor suppressor gene. In certain embodiments, the functional alteration is a driver mutation, e.g., an alteration that gives a selective advantage to a clone in its microenvironment, e.g., by increasing cell survival or reproduction. In some embodiments, the functional alteration can cause a clonal expansion. In certain embodiments, the functional alteration is an alteration capable of causing one or more of the following: (a) self-sufficiency in a growth signal; (b) decreased, e.g., insensitivity, to an anti-growth signal; (c) decreased apoptosis; (d) increased replicative potential; (e) sustained angiogenesis; or (f) tissue invasion or metastasis. In other embodiments, the functional alteration is not a passenger mutation, e.g., is an alteration that has detectable effect on the fitness of a clone of cells. In other embodiments, the functional alteration is not a variant of unknown significance (VUS), e.g., the pathogenicity of the variant can neither be confirmed nor ruled out.

"Binding entity" means any molecule to which molecular tags can be directly or indirectly attached that is capable of specifically binding to an analyte. The binding entity can be an affinity tag on a nucleic acid sequence. In certain embodiments, the binding entity allows for separation of the nucleic acid from a mixture, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features.

The term "neoplasm" or "neoplastic" cell refers to an abnormal proliferative stage, e.g., a hyperproliferative stage, in a cell or tissue that can include a benign, pre-malignant, malignant (cancer) or metastatic stage.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "inhibition" or "inhibitor" includes a reduction in a certain parameter, e.g., an activity, of a given molecule, e.g., an immune checkpoint inhibitor. For example, inhibition of an activity, e.g., an activity of, e.g., PD-1 or PD-L1, of at least 5%, 10%, 20%, 30%, 40%, 50%, 60%, or more is included by this term. Thus, inhibition need not be 100%. An inhibitor can inhibit a target directly (e.g., by binding to the target) or indirectly (e.g., by interfering an activity associated with the target). An inhibitor may also inhibit two or more different targets (e.g., simultaneously or sequentially), e.g., having multispecifity (e.g., bispecifity). An inhibitor of PD-1 or PD-L1, as described herein, can inhibit PD-1, PD-L1, or both.

The term "Programmed Death 1" or "PD-1" include isoforms, mammalian, e.g., human PD-1, species homologs of human PD-1, and analogs comprising at least one common epitope with PD-1. The amino acid sequence of PD-1, e.g., human PD-1, is known in the art, e.g., Shinohara T et al. (1994) *Genomics* 23(3):704-6; Finger L R, et al. *Gene* (1997) 197(1-2):177-87.

The term or "PD-Ligand 1" or "PD-L1" include isoforms, mammalian, e.g., human PD-1, species homologs of human PD-L1, and analogs comprising at least one common epitope with PD-L1. The amino acid sequence of PD-L1, e.g., human PD-L1, is known in the art.

As used herein, the term "indel" refers to an insertion, a deletion, or both, of one or more nucleotides in a nucleic acid of a cell. In certain embodiments, an indel includes both an insertion and a deletion of one or more nucleotides, where both the insertion and the deletion are nearby on the nucleic acid. In certain embodiments, the indel results in a net change in the total number of nucleotides. In certain embodiments, the indel results in a net change of about 1 to about 50 nucleotides.

As used herein, "chemotherapeutic agent" means a chemical substance, such as a cytotoxic or cytostatic agent that is used to treat a condition, particularly cancer.

As used herein, "cancer therapy" and "cancer treatment" are synonymous terms.

As used herein, "chemotherapy" and "chemotherapeutic" and "chemotherapeutic agent" are synonymous terms.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 75%, at least 80%, at least 85%, at least 90%, 91%, 92%, 93%, 94%, 95%, 96%, 97%, 98%, 99%, or more.

"Likely to" or "increased likelihood," as used herein, refers to an increased probability that an item, object, thing or person will occur. Thus, in one example, a subject that is likely to respond to treatment with an inhibitor of PD-1 or PD-L1, alone or in combination, has an increased probability of responding to treatment with the inhibitor alone or in combination, relative to a reference subject or group of subjects.

"Unlikely to" refers to a decreased probability that an event, item, object, thing or person will occur with respect to a reference. Thus, a subject that is unlikely to respond to treatment with an inhibitor of PD-1 or PD-L1, alone or in combination, has a decreased probability of responding to treatment with a kinase inhibitor, alone or in combination, relative to a reference subject or group of subjects.

"Sequencing" a nucleic acid molecule requires determining the identity of at least 1 nucleotide in the molecule. In embodiments, the identity of less than all of the nucleotides in a molecule is determined. In other embodiments, the identity of a majority or all of the nucleotides in the molecule is determined.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a high throughput fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample.

"Sample," "tissue sample," "patient sample," "patient cell or tissue sample" or "specimen" each refers to a tissue, a cell, e.g., a circulating cell, obtained from a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

A "tumor nucleic acid sample" as used herein, refers to nucleic acid molecules from a tumor or cancer sample. Typically, it is DNA, e.g., genomic DNA, or cDNA derived from RNA, from a tumor or cancer sample. In certain embodiments, the tumor nucleic acid sample is purified or isolated (e.g., it is removed from its natural state).

A "control" or "reference" "nucleic acid sample" as used herein, refers to nucleic acid molecules from a control or reference sample. Typically, it is DNA, e.g., genomic DNA, or cDNA derived from RNA, not containing the alteration or variation in the gene or gene product, e.g., not containing a mutation. In certain embodiments, the reference or control nucleic acid sample is a wild type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tissue (NAT), or any other non-cancerous sample from the same or a different subject.

"Adjacent to the interrogation position," as used herein, means that a site sufficiently close such that a detection reagent complementary with the site can be used to distinguish between a mutation, e.g., an alteration described herein, and a reference sequence, e.g., a non-mutant or wild-type sequence, in a target nucleic acid. Directly adjacent, as used herein, is where 2 nucleotides have no intervening nucleotides between them.

"Associated mutation," as used herein, refers to a mutation within a preselected distance, in terms of nucleotide or primary amino acid sequence, from a definitional mutation, e.g., a mutant as described herein. In embodiments, the associated mutation is within n, wherein n is 2, 5, 10, 20, 30, 50, 100, or 200 nucleotides from the definitional mutation (n does not include the nucleotides defining the associated and definitional mutations). In embodiments, the associated mutation is a translocation mutation.

"Interrogation position," as used herein, comprises at least one nucleotide (or, in the case of polypeptides, an amino acid residue) which corresponds to a nucleotide (or amino acid residue) that is mutated in a mutation of interest, e.g., a mutation being identified, or in a nucleic acid (or protein) being analyzed, e.g., sequenced, or recovered.

A "reference sequence," as used herein, e.g., as a comparator for a mutant sequence, is a sequence which has a different nucleotide or amino acid at an interrogation position than does the mutant(s) being analyzed. In one embodiment, the reference sequence is wild-type for at least the interrogation position.

Headings, e.g., (a), (b), (i) etc, are presented merely for ease of reading the specification and claims. The use of headings in the specification or claims does not require the steps or elements be performed in alphabetical or numerical order or the order in which they are presented.

Various aspects featured in the invention are described in further detail below. Additional definitions are set out throughout the specification.

Therapeutic Methods and Agents

"Treat," "treatment," and other forms of this word refer to the administration of an agent, e.g., a therapeutic agent, alone or in combination with a second agent in an amount effective to impede growth of a cancer, to cause a cancer to shrink by weight or volume, to extend the expected survival time of the subject and or time to progression of the tumor or the like. In those subjects, treatment can include, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life. A cancer is "treated" if at least one symptom of the cancer is alleviated, terminated, slowed or prevented. A cancer is also "treated" if recurrence or metastasis of the cancer is reduced, slowed, delayed or prevented.

As used herein, unless otherwise specified, the terms "prevent," "preventing" and "prevention" contemplate an action that occurs before a subject begins to suffer from the re-growth of the cancer and/or which inhibits or reduces the severity of the cancer.

As used herein, and unless otherwise specified, a "therapeutically effective amount" of an agent is an amount sufficient to provide a therapeutic benefit in the treatment or management of the cancer, or to delay or minimize one or more symptoms associated with the cancer. A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the cancer, or enhances the therapeutic efficacy of another therapeutic agent.

As used herein, and unless otherwise specified, a "prophylactically effective amount" of an agent is an amount sufficient to prevent re-growth of the cancer, or one or more symptoms associated with the cancer, or prevent its recurrence. A prophylactically effective amount of an agent means an amount of the agent, alone or in combination with other therapeutic agents, which provides a prophylactic benefit in the prevention of the cancer. The term "prophylactically effective amount" can encompass an amount that improves overall prophylaxis or enhances the prophylactic efficacy of another prophylactic agent.

The term "patient" or "subject" includes a human (e.g., a male or female of any age group), e.g., a pediatric patient (e.g., infant, child, adolescent); or adult patient (e.g., young adult, middle-aged adult or senior adult). In certain embodiments, the subject is an adult subject (e.g., male or female adult subject) having, or at risk of having, a melanoma as described herein. In certain embodiments, the subject is a subject of or above 10, 15, 20, 25, 30, 35, 40, 45, 50, 55, 60, 65, 70, 75, 80, 85, 90 years of age, or more. In certain embodiments, a subject is a subject between 0-10 years of age, 10-20 years of age, 20-30 years of age, 30-40 years of age, 40-50 years of age, 50-60 years of age, 60-70 years of age, 70-80 years of age, or 80-90 years of age. In certain embodiments, the subject is a subject between 25 and 29 years of age. In other embodiments, the subject is a subject between 15 and 29 years of age. In some embodiments, the subject is female and is between 15 and 29 years of age. In certain embodiments, the subject is 65 years of age, or more.

When the term patient" or "subject" is used in conjunction with administration of a compound or drug, then the patient has been the object of treatment, observation, and/or administration of the compound or drug.

The agents, e.g., the therapeutic agents described herein, can be administered in combination with a second therapeutic agent or a different therapeutic modality, e.g., anti-cancer agents, and/or in combination with surgical and/or radiation procedures.

By "in combination with," it is not intended to imply that the therapy or the therapeutic agents must be administered at the same time and/or formulated for delivery together, although these methods of delivery are within the scope of the invention. The pharmaceutical compositions can be administered concurrently with, prior to, or subsequent to, one or more other additional therapies or therapeutic agents. In general, each agent will be administered at a dose and/or on a time schedule determined for that agent. It will further be appreciated that therapeutic agents utilized in a combination can be administered together in a single composition or administered separately in different compositions. The particular combination to employ in a regimen will take into account compatibility of the first therapeutically active agent with the additional therapeutically active agent(s) and/or the desired therapeutic effect to be achieved.

As used herein, the term "responder" includes a subject who has a decrease in the size of a tumor, or in the extent of cancer in the body, or shows the disappearance of one or more (e.g., most or all) signs of cancer in response to a treatment, e.g., as defined by RECIST 1.1 criteria.

As used herein, the term "partial responder" includes a subject who has a decrease in the size of a tumor, or in the extent of cancer in the body, in response to a treatment, e.g., as defined by RECIST 1.1 criteria.

As used herein, the term "complete responder" includes a subject who shows the disappearance of most or all signs of cancer in response to a treatment, e.g., as defined by RECIST 1.1 criteria. The cancer needs not to be cured in the complete responder.

As used herein, the term "non-responder" includes a subject who does not have a decrease in the size of a tumor, or in the extent of cancer in the body, e.g., as defined by RECIST 1.1 criteria.

In some embodiments, subjects can be classified as responders (e.g., complete responders or partial responders) or non-responders as defined by classical partial or complete responses (RECIST 1.1 criteria), or atypical immune related responses lasting at least 12 months. In some embodiments, subjects with mixed responses necessitating additional systemic therapy or causing clinical deterioration in <12 months (e.g., as determined by a clinician) are considered non-responders (e.g., before, at or after the additional systemic therapy or clinical deterioration). In certain embodiments, the therapy responses are classified based on clinical review of imaging and clinician notes. RECIST 1.1 criteria is described, e.g., in Eisenhauer et al. *Eur J Cancer.* 2009; 45(2):228-247.

In some embodiments, the responder (e.g., a complete responder or partial responder) has a mutation load in a sample (e.g., a tumor sample) of about 3.3 or more somatic alterations per a preselected unit, e.g., per megabase, in a predetermined set of genes, e.g., the coding regions of a predetermined set of genes. In some embodiments, the responder (e.g., a complete responder) has a mutation load in a sample (e.g., a tumor sample) of about 23.1 or more somatic alterations per a preselected unit, e.g., per megabase, in a predetermined set of genes, e.g., the coding regions of a predetermined set of genes. In some embodiments, the responder (e.g., a partial responder) has a mutation load in a sample (e.g., a tumor sample) of about 3.3 or more but fewer than 23.2 somatic alterations per a preselected unit, e.g., per megabase, in a predetermined set of genes, e.g., the coding regions of a predetermined set of genes. In some embodiments, the non-responder has a mutation load in a sample (e.g., a tumor sample) of fewer than about 3.3 somatic alterations per a preselected unit, e.g., per megabase, in a predetermined set of genes, e.g., the coding regions of a predetermined set of genes.

In some embodiments, the responder (e.g., a complete responder or partial responder) is a member of a patient group (e.g., in a clinical trial) that has at least about 29% (e.g., at least about 35%, at least about 40%, at least about 50%, at least about 60%, at least about 70%, at least about 80%, at least about 85%, at least about 90%, or at least about 95%) objective response rate (ORR). In some embodiments, the responder (e.g., a complete responder) is a member of a patient group that has at least about 85% (e.g., at least about 90% or at least about 95%) objective response rate (ORR). In some embodiments, the responder (e.g., a partial responder) is a member of a patient group that has between about 29% and about 85% (e.g., between about 30% and about 80%, between about 40% and about 70%, or between about 50% and about 60%) objective response rate (ORR). In some embodiments, the non-responder is a member of a patient group that has less than about 25% (e.g., less than about 20% or less than about 10%) objective response rate (ORR).

Exemplary Therapeutic Agents and Modalities

The agent, e.g., therapeutic agent, can be a small molecule, a protein, a polypeptide, a peptide, an antibody molecule, a nucleic acid (e.g., a siRNA, an antisense or a micro RNA), a small molecule, or an immune cell therapy. Exemplary agents and classes of agents are described herein.

In one embodiment, the agent, e.g., therapeutic agent, binds and/or inhibits PD-1 or PD-L1. In one embodiment, the agent is an antibody molecule. The terms "antibody" and "antibody molecule" as used interchangeably herein refer to immunoglobulin molecules and immunologically active portions of immunoglobulin molecules, i.e., molecules that contain an antigen binding site which specifically binds an antigen, such as a polypeptide featured in the invention. A molecule which specifically binds to a given polypeptide featured in the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition," as used herein, refers to a population of antibody molecules that contain only one species of an antigen binding site capable of immunoreacting with a particular epitope. Antibodies to PD-1 or PD-L1 are known in the art, as well as techniques for generating antibodies to a polypeptide target, e.g., PD-1 or PD-L1.

Exemplary PD-1 Inhibitors

In certain embodiments, the inhibitor of PD-1 is an anti-PD-1 antibody. In certain embodiments, the inhibitor of PD-1 is chosen from nivolumab (ONO-4538, BMS-936558, or MDX1106), pembrolizumab (MK-3475 or lambrolizumab), pidilizumab (CT-011), MEDI0680 (AMP-514), PDR001, REGN2810, BGB-108, BGB-A317, SHR-1210 (HR-301210, SHR1210, or SHR-1210), PF-06801591, or AMP-224.

In other embodiments, the PD-1 inhibitor is an anti-PD-1 antibody chosen from Nivolumab, Pembrolizumab or Pidilizumab.

In some embodiments, the anti-PD-1 antibody is Nivolumab (CAS Registry Number: 946414-94-4). Alternative names for Nivolumab include MDX-1106, MDX-1106-04, ONO-4538, or BMS-936558. Nivolumab is a fully human IgG4 monoclonal antibody which specifically blocks PD1. Nivolumab (clone 5C4) and other human monoclonal antibodies that specifically bind to PD1 are disclosed, e.g., in U.S. Pat. No. 8,008,449 and WO2006/121168. In one embodiment, the inhibitor of PD-1 is Nivolumab, and having a heavy and light chain amino acid sequences disclosed as SEQ ID NOS: 2 and 3, respectively, in U.S. Pat. No. 8,008,449 and WO2006/121168 (or an amino acid sequence substantially identical or similar thereto, e.g., a sequence at least 85%, 90%, 95% identical or higher to the amino acid sequence specified).

In some embodiments, the anti-PD-1 antibody is Pembrolizumab. Pembrolizumab (also referred to as Lambrolizumab, MK-3475, MK03475, SCH-900475 or KEYTRUDA®; Merck) is a humanized IgG4 monoclonal antibody that binds to PD-1. Pembrolizumab and other humanized anti-PD-1 antibodies are disclosed in Hamid, O. et al. (2013) *New England Journal of Medicine* 369 (2): 134-44, U.S. Pat. No. 8,354,509 and WO2009/114335. In one embodiment, the inhibitor of PD-1 is Pembrolizumab disclosed in, e.g., U.S. Pat. No. 8,354,509 and WO 2009/114335, and having a heavy and light chain amino acid sequences disclosed as SEQ ID NOS: 4 and 5, respectively, in U.S. Pat. No. 8,354,509 and WO 2009/114335 (or an amino acid sequence substantially identical or similar thereto, e.g., a sequence at least 85%, 90%, 95% identical or higher to the sequence specified).

In some embodiments, the anti-PD-1 antibody is Pidilizumab. Pidilizumab (CT-011; Cure Tech) is a humanized IgG1k monoclonal antibody that binds to PD-1. Pidilizumab and other humanized anti-PD-1 monoclonal antibodies are disclosed in WO2009/101611.

Other anti-PD-1 antibodies include AMP 514 (Amplimmune), among others, e.g., anti-PD1 antibodies disclosed in U.S. Pat. No. 8,609,089, US 2010028330, and/or US 20120114649.

Exemplary PD-L1 Inhibitors

In certain embodiments, the inhibitor of PD-L1 is an anti-PD-L1 antibody. In certain embodiments, the inhibitor of PD-L1 is chosen from atezolizumab (MPDL3280A, RG7446, or RO5541267), YW243.55.570, MDX-1105, durvalumab (MEDI4736), or avelumab (MSB0010718C).

In some embodiments, the PD-L1 inhibitor is an antibody molecule. In some embodiments, the anti-PD-L1 inhibitor is chosen from YW243.55.570, MPDL3280A, MEDI-4736, MSB-0010718C, or MDX-1105.

In some embodiments, the anti-PD-L1 antibody is MSB0010718C. MSB0010718C (also referred to as A09-246-2; Merck Serono) is a monoclonal antibody that binds to PD-L1. MSB0010718C and other humanized anti-PD-L1 antibodies are disclosed, e.g., in WO2013/079174, and having a heavy and light chain variable region amino acid sequences disclosed as SEQ ID NOS: 24 and 25, respectively, in WO2013/079174 (or a sequence substantially identical or similar thereto, e.g., an amino acid sequence at least 85%, 90%, 95% identical or higher to the amino acid sequence specified).

In one embodiment, the PD-L1 inhibitor is YW243.55.570. The YW243.55.570 antibody is an anti-PD-L1 described in WO 2010/077634 (heavy and light chain variable region amino acid sequences shown in SEQ ID NOS: 20 and 21, respectively, of WO 2010/077634), and having a sequence disclosed therein (or an amino acid sequence substantially identical or similar thereto, e.g., an amino acid sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

Additional Therapies

Treatments described herein can be provided to a patient having had an unsatisfactory response to a different therapy, e.g., a non-anti-PD-1 and/or non-anti-PD-L1 therapeutic agent or therapeutic modality. In one embodiment, the subject is undergoing or has undergone treatment with a different therapy, e.g., a non-anti-PD-1 and/or non-anti-PD-L1 therapeutic agent or therapeutic modality. The different therapy can be a small molecule, a protein, a polypeptide, a peptide, an antibody molecule, a nucleic acid (e.g., a siRNA, an antisense or a micro RNA), or a cell.

In one embodiment, the different therapy is chosen from a chemotherapy, a radiation therapy, an immunotherapy, an immunoradiotherapy, an oncolytic virotherapy, a surgical procedure, or any combination thereof. In one embodiment, the different therapy comprises one or more of: dacarbazine, temozolomide, interleukin-2 (IL-2), an interferon, an inhibitor of CTLA-4 (e.g., an anti-CTLA-4 antibody, e.g., ipilimumab), a BRAF inhibitor, a MEK inhibitor, talimogene laherparepvec, an adoptive cell transfer, or any combination thereof. In one embodiment, the different therapy comprises one or more of: dacarbazine, temozolomide, interleukin-2 (IL-2) (e.g., a recombinant interferon alfa-2b or a peginterferon alfa-2b), an interferon, ipilimumab, a BRAF inhibitor (e.g., vemurafenib or dabrafenib), a MEK inhibitor (e.g., cobimetinib or trametinib), talimogene laherparepvec, an adoptive cell transfer (e.g., modified T cells or modified dendritic cells), or any combination thereof.

An agent, e.g., therapeutic agent, described herein can be administered, alone or in combination, e.g., in combination with other chemotherapeutic agents or procedures, in an amount sufficient to reduce or inhibit the tumor cell growth, and/or treat or prevent the cancer(s), in the subject.

Nucleic Acid Inhibitors

In another embodiment, the agent is a nucleic acid inhibitor selected from an antisense molecule, a ribozyme, a double-stranded RNA molecule, a triple helix molecule, that hybridizes to a nucleic acid encoding the alteration, or a transcription regulatory region that blocks or reduces mRNA expression of the alteration.

In one embodiment, the nucleic acid antagonist is a siRNA that targets mRNA encoding a mutation. Other types of antagonistic nucleic acids can also be used, e.g., a dsRNA, a ribozyme, a triple-helix former, or an antisense nucleic acid. Accordingly, isolated nucleic acid molecules that are nucleic acid inhibitors, e.g., antisense, RNAi, to a mutation-encoding nucleic acid molecule are provided.

An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire nucleotide sequence encoding one or more mutations, or to only a portion thereof. In another embodiment, the antisense nucleic acid molecule is antisense to a "noncoding region" of the coding strand of a nucleotide sequence encoding one or more mutations (e.g., the 5' and 3' untranslated regions). Anti-sense agents can include, for example, from about 8 to about 80 nucleobases (i.e., from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding a mutation described herein.

The complementary region can extend for between about 8 to about 80 nucleobases. The compounds can include one or more modified nucleobases. Modified nucleobases are known in the art. Descriptions of modified nucleic acid agents are also available. See, e.g., U.S. Pat. Nos. 4,987,071; 5,116,742; and 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

The antisense nucleic acid molecules are typically administered to a subject (e.g., by direct injection at a tissue site), or generated in situ such that they hybridize with or bind to cellular mRNA and/or genomic DNA encoding a mutation to thereby inhibit expression of the protein, e.g., by inhibiting transcription and/or translation. Alternatively, antisense nucleic acid molecules can be modified to target selected cells and then be administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

SiRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) *Proc. Natl. Acad. Sci. USA* 97:6499-6503; Billy et al. (2001) *Proc. Natl. Sci. USA* 98:14428-14433; Elbashir et al. (2001) *Nature*. 411:494-8; Yang et al. (2002) *Proc. Natl. Acad. Sci. USA* 99:9942-9947; Siolas et al. (2005), *Nat. Biotechnol.* 23(2):227-31; U.S. Patent Publication Nos 20040086884; 20030166282; 20030143204; 20040038278; and 20030224432.

In still another embodiment, an antisense nucleic acid featured in the invention is a ribozyme. A ribozyme having specificity for a mutation-encoding nucleic acid can include one or more sequences complementary to the nucleotide sequence of a mutation cDNA disclosed herein, and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a mutation-encoding mRNA. See, e.g., Cech et al. U.S. Pat. No. 4,987,071; and Cech et al. U.S. Pat. No. 5,116,742. Alternatively, mutation mRNA can be used to select a catalytic RNA having a specific ribonuclease activity from a pool of RNA molecules. See, e.g., Bartel, D. and Szostak, J. W. (1993) *Science* 261:1411-1418.

Inhibition of a mutated gene can be accomplished by targeting nucleotide sequences complementary to the regulatory region of the mutation to form triple helical structures that prevent transcription of the mutated gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A mutated nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmd (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of mutated nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of mutated nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; WO88/09810) or the blood-brain barrier (see, e.g., WO 89/10134).

In addition, oligonucleotides can be modified with hybridization-triggered cleavage agents (see, e.g., Krol et al. (1988) *Bio-Techniques* 6:958-976) or intercalating agents (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

In some embodiments, a nucleic acid inhibitor described herein is provided for the inhibition of expression of a nucleic acid comprising the alteration in vitro.

Cancer

The invention described herein can be used to treat a cancer or to evaluate a subject having a cancer.

Exemplary cancers include, but are not limited to, melanomas, B cell cancer, e.g., multiple myeloma, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia Vera, Hodgkin lymphoma, non-Hodgkin lymphoma (NHL), soft-tissue sarcoma, fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and a metastatic lesion thereof.

Melanoma

The invention provides, at least in part, methods for treating a cancer, e.g., a melanoma, in a subject. In certain embodiments, the methods include treatment of a cancer, e.g., a melanoma, harboring an alteration described herein (e.g., an alteration in a gene disclosed in Table 1, e.g., an alteration in an NF1 gene or an LRP1B gene described herein). The methods include administering to the subject a therapeutic agent, e.g., an immunotherapeutic agent, e.g., an inhibitor of PD-1 or PD-L1.

In certain embodiments, the cancer is a melanoma. In certain embodiments, the cancer is an advanced melanoma. In certain embodiments, the cancer is a metastatic melanoma. In certain embodiments, the cancer, e.g., melanoma, is at a high risk of recurrence or replase. In certain embodiments, the cancer, e.g., melanoma, is at a high risk of metastasis. In some embodiments, the melanoma is any stage or risk group melanoma defined according to any suitable melanoma classification system known to those of skill in the art.

In certain embodiments, the melanoma is any one of a stage 0, stage IA, stage IB, stage IIA, stage IIB, stage IIC, stage III, or stage IV melanoma. In other embodiments, the melanoma is any one of a stage 0, stage IA, stage IB, stage IIA, stage IIB, stage IIC, stage III, or stage IV melanoma, as defined by the American Joint Committee on Cancer (AJCC) melanoma staging system. In some embodiments, the melanoma is any stage melanoma defined according to any suitable melanoma classification system known to those of skill in the art. In other embodiments, the melanoma is any one of a stage 0, stage IA, stage IB, stage IIA, stage IIB, stage IIC, stage III, or stage IV melanoma, set forth in Tables 2A-2B.

In certain embodiments, the melanoma is a stage III or stage IV melanoma. In certain embodiments, the melanoma is a stage III melanoma. In certain embodiments, the melanoma is a stage III melanoma according to any suitable melanoma classification system known to those of skill in the art. In certain embodiments, the cancer is a stage III melanoma set forth in Tables 2A-2B. In certain embodiments, the melanoma is a stage IV melanoma. In certain embodiments, the melanoma is a stage IV melanoma according to any suitable melanoma classification system known to those of skill in the art. In certain embodiments, the cancer is a stage IV melanoma set forth in Tables 2A-2B.

In certain embodiments, the melanoma is an advanced melanoma. In some embodiments, the advanced melanoma is a stage III or stage IV melanoma, e.g., as set forth in Tables 2A-2B. In certain embodiments, the melanoma is a meatastic melanoma. In some embodiments, the metastatic melanoma is a stage III or stage IV melanoma, e.g., as set forth in Tables 2A-2B.

TABLE 2A

TNM Staging Categories for Cutaneous Melanoma*

| Classification | Thickness (mm) | Ulceration Status/Mitoses |
|---|---|---|
| T | | |
| Tis | NA | NA |
| T1 | ≤1.00 | a: Without ulceration and mitosis <1/mm$^2$ |
| | | b: With ulceration or mitoses ≥1/mm$^2$ |
| T2 | 1.01-2.00 | a: Without ulceration |
| | | b: With ulceration |
| T3 | 2.01-4.00 | a: Without ulceration |
| | | b: With ulceration |
| T4 | >4.00 | a: Without ulceration |
| | | b: With ulceration |
| N | No. of Metastatic Nodes | Nodal Metastatic Burden |
| N0 | 0 | NA |
| N1 | 1 | a: Micrometastasis† |
| | | b: Macrometastasis‡ |
| N2 | 2-3 | a: Micrometastasis† |
| | | b: Macrometastasis‡ |
| | | c: In transit metastases/satellites without metastatic nodes |

TABLE 2A-continued

TNM Staging Categories for Cutaneous Melanoma*

| | | |
|---|---|---|
| N3 | 4+ metastatic nodes, or matted nodes, or in transit metastases/satellites with metastatic nodes | |

| M | Site | Serum LDH |
|---|---|---|
| M0 | No distant metastases | NA |
| M1a | Distant skin, subcutaneous, or nodal metastases | Normal |
| M1b | Lung metastases | Normal |
| M1c | All other visceral metastases | Normal |
| | Any distant metastasis | Elevated |

Abbreviations: NA, not applicable; LDH, lactate dehydrogenase.
*Balch et al. "Final Version of 2009 AJCC Melanoma Staging and Classification," *J Clin Oncol.* 2009; 27(36): 6199-6206.
†Micrometastases are diagnosed after sentinel lymph node biopsy.
‡Macrometastases are defined as clinically detectable nodal metastases confirmed pathologically.

TABLE 2B

Anatomic Stage Groupings for Cutaneous Melanoma*

| | Clinical Staging† | | | | Pathologic Staging‡ | | |
|---|---|---|---|---|---|---|---|
| | T | N | M | | T | N | M |
| 0 | Tis | N0 | M0 | 0 | Tis | N0 | M0 |
| IA | T1a | N0 | M0 | IA | T1a | N0 | M0 |
| IB | T1b | N0 | M0 | IB | T1b | N0 | M0 |
| | T2a | N0 | M0 | | T2a | N0 | M0 |
| IIA | T2b | N0 | M0 | IIA | T2b | N0 | M0 |
| | T3a | N0 | M0 | | T3a | N0 | M0 |
| IIB | T3b | N0 | M0 | IIB | T3b | N0 | M0 |
| | T4a | N0 | M0 | | T4a | N0 | M0 |
| IIC | T4b | N0 | M0 | IIC | T4b | N0 | M0 |
| III | Any T | N > N0 | M0 | IIIA | T1-4a | N1a | M0 |
| | | | | | T1-4a | N2a | M0 |
| | | | | IIIB | T1-4b | N1a | M0 |
| | | | | | T1-4b | N2a | M0 |
| | | | | | T1-4a | N1b | M0 |
| | | | | | T1-4a | N2b | M0 |
| | | | | | T1-4a | N2c | M0 |
| | | | | IIIC | T1-4b | N1b | M0 |
| | | | | | T1-4b | N2b | M0 |
| | | | | | T1-4b | N2c | M0 |
| | | | | | Any T | N3 | M0 |
| IV | Any T | Any N | M1 | IV | Any T | Any N | M1 |

*Balch et al. "Final Version of 2009 AJCC Melanoma Staging and Classification," *J Clin Oncol.* 2009; 27(36): 6199-6206.
†Clinical staging includes microstaging of the primary melanoma and clinical/radiologic evaluation for metastases. By convention, it should be used after complete excision of the primary melanoma with clinical assessment for regional and distant metastases.
‡Pathologic staging includes microstaging of the primary melanoma and pathologic information about the regional lymph nodes after partial (i.e., sentinel node biopsy) or complete lymphadenectomy. Pathologic stage 0 or stage IA patients are the exception; they do not require pathologic evaluation of their lymph nodes.

In certain embodiments, the melanoma is a cutaneous melanoma. In other embodiments, the melanoma is a non-cutaneous melanoma.

In certain embodiments, the cancer, e.g., the melanoma, e.g., the advanced or metastatic melanoma, comprises, or is identified or determined as having, an alteration, e.g., an alteration described herein, e.g., in a gene described herein. In certain embodiments, the cancer, e.g., the melanoma, e.g., the advanced or metastatic melanoma, comprises, or is identified or determined as having, an alteration in a gene described in Table 1. In other embodiments, the cancer, e.g., the melanoma, e.g., the advanced or metastatic melanoma, comprises, or is identified or determined as having, a plurality of alterations in a gene described in Table 1. In other embodiments, the cancer, e.g., the melanoma, e.g., the advanced or metastatic melanoma, comprises, or is identified or determined as having, a plurality of alterations in a plurality of genes described in Table 1.

In certain embodiments, the cancer, e.g., the melanoma, e.g., the advanced or metastatic melanoma, comprises, or is identified or determined as having, an alteration in an NF1 gene, e.g., an alteration in an NF1 gene as described herein.

In certain embodiments, the alteration in the NF1 gene results in decreased activity of an NF1 gene product (e.g., an NF1 protein), compared to a wildtype activity of NF1. For example, the alteration can result in an alteration (e.g., a decrease) in a GTPase activator activity, a phosphatidylcholine binding activity, and/or a phosphatidylethanolamine binding activity of NF1. In certain embodiments, the alteration results in an elevated activation of RAS.

In one embodiment, the alteration in the NF1 gene is, or comprises, a mutation (e.g., a somatic mutation), e.g., a substitution (e.g., a base substitution), an insertion, or a deletion. Exemplary NF1 alterations associated with melanoma are described, e.g., in Wiesner et al. *Am J Surg Pathol.* 2015; 39(10): 1357-62; Krauthammer et al. *Nat Genet.* 2015; 47(9): 996-1002. Additional alterations in the NF1 gene are described, e.g., in the COSMIC database (cancer.sanger.ac.uk/cosmic; Forbes et al. *Nucl. Acids Res.* 2015; 43 (D1): D805-D811).

In certain embodiments, the cancer, e.g., the melanoma, e.g., the advanced or metastatic melanoma, comprises, or is identified or determined as having, an alteration in an LRP1B gene, e.g., an alteration in an LRP1B gene as described herein.

In certain embodiments, the alteration in the LRP1B gene results in decreased activity of an LRP1B gene product (e.g., an LRP1B protein), compared to a wildtype activity of LRP1B. For example, the alteration can result in an alteration (e.g., a decrease) in a calcium ion binding and/or low-density lipoprotein receptor activity of LRP1B.

In one embodiment, the alteration in the LRP1B gene is, or comprises, a mutation (e.g., a somatic mutation), e.g., a substitution (e.g., a base substitution), an insertion, or a deletion. Exemplary LRP1B alterations associated with melanoma are described, e.g., in Nikolaev et al. *Nat Genet.* 2011; 44(2):133-9. Additional alterations in the LRP1B gene are described, e.g., in the COSMIC database (cancer.sanger.ac.uk/cosmic; Forbes et al. *Nucl. Acids Res.* 2015; 43 (D1): D805-D811).

In other embodiments, the cancer, e.g., the melanoma, e.g., the advanced or metastatic melanoma, comprises, or is identified or determined as having, an alteration in a BRAF gene, e.g., an alteration in a BRAF gene as described herein.

In certain embodiments, the alteration in the BRAF gene results in increased activity of a BRAF gene product (e.g., a BRAF protein), compared to a wild-type activity of BRAF. For example, the alteration can result in alteration in one or more of the following activities of BRAF: ATP binding calcium, ion binding, identical protein binding, MAP kinase kinase kinase activity, protein kinase activity, or protein serine/threonine kinase activity. In certain embodiments, the alteration results in an alteration (e.g., an increase) in a kinase activity of BRAF.

In one embodiment, the BRAF alteration is, or comprises, a mutation (e.g., a somatic mutation), e.g., a substitution (e.g., a base substitution), an insertion, or a deletion. In certain embodiments, the alteration is a base substitution.

In certain embodiments, the alteration in BRAF is located at codon V600. In certain embodiments, the alteration in BRAF is a V600E alteration. In certain embodiments, the alteration in BRAF is a V600K alteration. In certain embodiments, the alteration in BRAF is a V600R alteration. In certain embodiments, the alteration in BRAF is a V600D alteration.

In certain embodiments, the alteration in BRAF is an alteration other than a V600 alteration. In certain embodiments, the alteration in BRAF is a K601 alteration. In certain embodiments, the alteration in BRAF is a K601E alteration. In certain embodiments, the alteration in BRAF is a G469 alteration. In certain embodiments, the alteration in BRAF is a G469E alteration. In certain embodiments, the alteration in BRAF is a D594 alteration. In certain embodiments, the alteration in BRAF is a D594G alteration. In certain embodiments, the alteration in BRAF is an L597 alteration. In certain embodiments, the alteration in BRAF is an L597S alteration. In certain embodiments, the alteration in BRAF is an S467 alteration. In certain embodiments, the alteration in BRAF is an S467L alteration.

In other embodiments, the cancer, e.g., the melanoma, e.g., the advanced or metastatic melanoma, comprises, or is identified or determined as having, an alteration in an NRAS gene, e.g., an alteration in an NRAS gene as described herein.

In certain embodiments, the alteration in the NRAS gene results in increased activity of a NRAS gene product (e.g., an NRAS protein), compared to a wild-type activity of NRAS. For example, the alteration can result in an alteration (e.g., a decrease) in a GTPase activity of NRAS. In certain embodiments, the NRAS protein comprises an alteration that decreases intrinsic GTP hydrolysis, e.g., resulting in a constitutively active NRAS.

In one embodiment, the NRAS alteration is, or comprises, a mutation (e.g., a somatic mutation), e.g., a substitution (e.g., a base substitution), an insertion, or a deletion. In certain embodiments, the alteration is a base substitution.

In certain embodiments, the alteration in NRAS is located at codon Q61. In certain embodiments, the alteration in NRAS is a Q61H alteration. In certain embodiments, the alteration in NRAS is a Q61K alteration. In certain embodiments, the alteration in NRAS is a Q61L alteration. In certain embodiments, the alteration in NRAS is a Q61P alteration. In certain embodiments, the alteration in NRAS is a Q61Q alteration. In certain embodiments, the alteration in NRAS is a Q61R alteration.

In other embodiments, the alteration in NRAS is a G12 alteration. In certain embodiments, the alteration in NRAS is a G12A alteration. In certain embodiments, the alteration in NRAS is a G12C alteration. In certain embodiments, the alteration in NRAS is a G12D alteration. In certain embodiments, the alteration in NRAS is a G12R alteration. In certain embodiments, the alteration in NRAS is a G12S alteration. In certain embodiments, the alteration in NRAS is a G12V alteration. In certain embodiments, the alteration in NRAS is a G13 alteration. In certain embodiments, the alteration in NRAS is a G13C alteration. In certain embodiments, the alteration in NRAS is a G13D alteration. In certain embodiments, the alteration in NRAS is a G13R alteration. In certain embodiments, the alteration in NRAS is a G13V alteration. In certain embodiments, the alteration in NRAS is an S17 alteration. In certain embodiments, the alteration in NRAS is an S17N alteration.

Mutation Load

As used herein, the term "mutation load" or "mutational load" refers to the level, e.g., number, of an alteration (e.g., one or more alterations, e.g., one or more somatic alterations) per a preselected unit (e.g., per megabase) in a predetermined set of genes (e.g., in the coding regions of the predetermined set of genes). Mutation load can be measured, e.g., on a whole genome or exome basis, or on the basis of a subset of genome or exome. In certain embodiments, the mutation load measured on the basis of a subset of genome or exome can be extrapolated to determine a whole genome or exome mutation load.

In certain embodiments, the mutation load is measured in a sample, e.g., a tumor sample (e.g., a melanoma sample or a sample acquired or derived from a melanoma), from a subject, e.g., a subject described herein. In certain embodiments, the mutation load is measured by determining one, two, three or all of the following:

(i) the level of a somatic alteration in a predetermined set of genes set forth in Table 1,
(ii) the presence of a somatic alteration in an NF1 gene,
(iii) the number of a somatic alteration in an LRP1B gene, or
(iv) the number of a C to T transition.

In certain embodiments, the level of a somatic alteration in a predetermined set of genes set forth in Table 1 correlates with the mutation load (e.g., the whole genome or exome mutation load). In certain embodiments, the presence of a somatic alteration in an NF1 gene correlates with the mutation load (e.g., the mutation load measured based on the level of a somatic alteration in a predetermined set of genes set forth in Table 1, or the whole genome or exome mutation load). In certain embodiments, the number of a somatic alteration in an LRP1B gene correlates with the mutation load (e.g., the mutation load measured based on the level of a somatic alteration in a predetermined set of genes set forth in Table 1, or the whole genome or exome mutation load). In certain embodiments, the number of a C to T transition correlates with the mutation load (e.g., the mutation load measured based on the level of a somatic alteration in a predetermined set of genes set forth in Table 1, or the whole genome or exome mutation load).

The terms "mutation load," "mutational load," "mutation burden," and "mutational burden" are used interchangeably herein. In the context of a tumor, a mutational load is also referred to herein as "tumor mutational burden," "tumor mutation burden," or "TMB."

Exemplary Genes Associated with Cancer

The invention described herein include, e.g., measuring the mutation load, e.g., by determining the level of a somatic alteration (e.g., one or more somatic alterations) in a predetermined set of genes associated with cancer, e.g., as disclosed herein.

In certain embodiments, the level of a somatic alteration in a gene or gene product set forth in Table 1 is determined. In certain embodiments, the level of a somatic alteration in the coding region of a gene set forth in Table 1 is determined.

TABLE 1

| Exemplary Genes |
|---|
| Gene List |
| ABL1 |
| ABL2 |
| ACVR1B |
| AKT1 |
| AKT2 |
| AKT3 |
| ALK |
| AMER1 (FAM123B) |
| APC |
| AR |

TABLE 1-continued

| Exemplary Genes |
|---|
| ARAF |
| ARFRP1 |
| ARID1A |
| ARID1B |
| ARID2 |
| ASXL1 |
| ATM |
| ATR |
| ATRX |
| AURKA |
| AURKB |
| AXIN1 |
| AXL |
| BAP1 |
| BARD1 |
| BCL2 |
| BCL2L1 |
| BCL2L2 |
| BCL6 |
| BCOR |
| BCORL1 |
| BLM |
| BRAF |
| BRCA1 |
| BRCA2 |
| BRD4 |
| BRIP1 |
| BTG1 |
| BTK |
| C11orf30 (EMSY) |
| CARD11 |
| CBFB |
| CBL |
| CCND1 |
| CCND2 |
| CCND3 |
| CCNE1 |
| CD274 |
| CD79A |
| CD79B |
| CDC73 |
| CDH1 |
| CDK12 |
| CDK4 |
| CDK6 |
| CDK8 |
| CDKN1A |
| CDKN1B |
| CDKN2A |
| CDKN2B |
| CDKN2C |
| CEBPA |
| CHD2 |
| CHD4 |
| CHEK1 |
| CHEK2 |
| CIC |
| CREBBP |
| CRKL |
| CRLF2 |
| CSF1R |
| CTCF |
| CTNNA1 |
| CTNNB1 |
| CUL3 |
| CYLD |
| DAXX |
| DDR2 |
| DICER1 |
| DNMT3A |
| DOT1L |
| EGFR |
| EP300 |
| EPHA3 |
| EPHA5 |
| EPHA7 |
| EPHB1 |
| ERBB2 |
| ERBB3 |
| ERBB4 |
| ERG |
| ERRFI1 |
| ESR1 |
| EZH2 |
| FAM46C |
| FANCA |
| FANCC |
| FANCD2 |
| FANCE |
| FANCF |
| FANCG |
| FANCL |
| FAS |
| FAT1 |
| FBXW7 |
| FGF10 |
| FGF14 |
| FGF19 |
| FGF23 |
| FGF3 |
| FGF4 |
| FGF6 |
| FGFR1 |
| FGFR2 |
| FGFR3 |
| FGFR4 |
| FH |
| FLCN |
| FLT1 |
| FLT3 |
| FLT4 |
| FOXL2 |
| FOXP1 |
| FRS2 |
| FUBP1 |
| GABRA6 |
| GATA1 |
| GATA2 |
| GATA3 |
| GATA4 |
| GATA6 |
| GID4 (C17orf39) |
| GLI1 |
| GNA11 |
| GNA13 |
| GNAQ |
| GNAS |
| GPR124 |
| GRIN2A |
| GRM3 |
| GSK3B |
| H3F3A |
| HGF |
| HNF1A |
| HRAS |
| HSD3B1 |
| HSP90AA1 |
| IDH1 |
| IDH2 |
| IGF1R |
| IGF2 |
| IKBKE |
| IKZF1 |
| IL7R |
| INHBA |
| INPP4B |
| IRF2 |
| IRF4 |
| IRS2 |
| JAK1 |
| JAK2 |
| JAK3 |
| JUN |
| KAT6A |

TABLE 1-continued

Exemplary Genes (MYST3)
KDM5A
KDM5C
KDM6A
KDR
KEAP1
KEL
KIT
KLHL6
KMT2A
(MLL)
KMT2C
(MLL3)
KMT2D
(MLL2)
KRAS
LMO1
LRP1B
LYN
LZTR1
MAGI2
MAP2K1
MAP2K2
MAP2K4
MAP3K1
MCL1
MDM2
MDM4
MED12
MEF2B
MEN1
MET
MITF
MLH1
MPL
MRE11A
MSH2
MSH6
MTOR
MUTYH
MYC
MYCL
(MYCL1)
MYCN
MYD88
NF1
NF2
NFE2L2
NFKBIA
NKX2-1
NOTCH1
NOTCH2
NOTCH3
NPM1
NRAS
NSD1
NTRK1
NTRK2
NTRK3
NUP93
PAK3
PALB2
PARK2
PAX5
PBRM1
PDCD1LG2
PDGFRA
PDGFRB
PDK1
PIK3C2B
PIK3CA
PIK3CB
PIK3CG
PIK3R1
PIK3R2
PLCG2
PMS2
POLD1
POLE
PPP2R1A
PRDM1
PREX2
PRKAR1A
PRKCI
PRKDC
PRSS8
PTCH1
PTEN
PTPN11
QKI
RAC1
RAD50
RAD51
RAF1
RANBP2
RARA
RB1
RBM10
RET
RICTOR
RNF43
ROS1
RPTOR
RUNX1
RUNX1T1
SDHA
SDHB
SDHC
SDHD
SETD2
SF3B1
SLIT2
SMAD2
SMAD3
SMAD4
SMARCA4
SMARCB1
SMO
SNCAIP
SOCS1
SOX10
SOX2
SOX9
SPEN
SPOP
SPTA1
SRC
STAG2
STAT3
STAT4
STK11
SUFU
SYK
TAF1
TBX3
TERC
TERT
(promoter
only)
TET2
TGFBR2
TNFAIP3
TNFRSF14
TOP1
TOP2A
TP53
TSC1
TSC2
TSHR
U2AF1
VEGFA
VHL
WISP3
WT1
XPO1
ZBTB2

TABLE 1-continued

Exemplary Genes

ZNF217
ZNF703
Select Rearrangements

ALK
BCL2
BCR
BRAF
BRCA1
BRCA2
BRD4
EGFR
ETV1
ETV4
ETV5
ETV6
FGFR1
FGFR2
FGFR3
KIT
MSH2
MYB
MYC
NOTCH2
NTRK1
NTRK2
PDGFRA
RAF1
RARA
RET
ROS1
TMPRSS2

Neurofibromin 1 (NF1)

The invention described herein include, e.g., determining a presence of an alteration (e.g., a somatic alteration) in an NF1 gene, or measuring the mutation load, e.g., by determining a presence of an alteration (e.g., a somatic alteration) in an NF1 gene.

The neurofibromin 1 (NF1) gene, which is also known as WSS, NFNS, or VRNF, encodes a protein that functions as a negative regulator of the Ras signal transduction pathway. Mutations in this gene have been linked, e.g., to neurofibromatosis type 1, juvenile myelomonocytic leukemia and Watson syndrome. The mRNA for this gene is subject to RNA editing (CGA>UGA→Arg1306Term) resulting in premature translation termination. Alternatively spliced transcript variants encoding different isoforms have also been described for this gene.

The nucleotide and amino acid sequences of human NF1 are described, e.g., in Wallace et al. *Science.* 1990; 249: 181-186, Erratum: Wallace et al. *Science.* 1990; 250: 1749-1749 (isoform 1); Marchuk et al. *Genomics.* 1991; 11: 931-940 (isoform 1); Cawthon et al. *Cell.* 1990; 62:193-201 (isoform 1); Bernards et al. *DNA Cell Biol.* 1992; 11: 727-734 (isoforms 1 and 2); Li et al. *Genomics.* 1995; 25: 9-18 (isoforms 1 and 2); Nishi et al. *Oncogene.* 1991; 6: 1555-1559 (isoforms 1 and 2); Andersen et al. *Mol. Cell. Biol.* 1993; 13: 487-495 (isoform 2); Suzuki et al. *Biochem. Biophys. Res. Commun.* 1991; 181:955-961 (isoform 2); Suzuki et al. *Biochem. Biophys. Res. Commun.* 1992; 187: 984-990 (isoform 3); Martin et al. *Cell.* 1990; 63: 843-849 (isoform 4); Suzuki et al. *Tohoku J. Exp. Med.* 1995; 175: 225-233 (isoform 5); and Xu et al. *Cell.* 1990; 62: 599-608 (isoforms 1 and 6).

Additional variants, mutations, and polymorphisms of human NF1 are also described, e.g., in Upadhyaya et al. *Hum. Mutat.* 1994; 4: 83-101; Shen et al. *J. Med. Genet.* 1996; 33: 2-17; Li et al. *Cell.* 1992; 69: 275-281 (variant Glu-1444); Upadhyaya et al. *Hum. Mol. Genet.* 1992; 1: 735-740 (variants NF1 Met-2164 and Asn-2192); Tassabehji et al. *Am. J. Hum. Genet.* 1993; 53: 90-95 (variant Gly-His-Glu-Gln-Gln-Lys-Leu-Pro-Ala-Ala-Thr-Leu-Ala-Leu-1733 ins); Shen et al. *Hum. Mol. Genet.* 1993; 2: 1861-1864 (variant Met-991 del); Purandare et al. *Hum. Mol. Genet.* 1994; 3: 1109-1115 (variants NF1 Asp-1166 and Arg-1440); Abernathy et al. *Hum. Mutat.* 1994; 3: 347-352 (variant NF1 2387-Asn-Phe-2388 del); Upadhyaya et al. *J. Med. Genet.* 1995; 32: 706-710 (variant NF1 Ala-2631); Gasparini et al. *Hum. Genet.* 1996; 97: 492-495 (variant NF1 Arg-629); Wu et al. *Hum. Mutat.* 1996; 8: 51-56 (variant NF1 Arg-1035); Upadhyaya et al. *Hum. Genet.* 1997; 99: 88-92 (variants NF1 Ser-1412; Gln-1440; Glu-1444 And Gly-1489); Maynard et al. *Hum. Genet.* 1997; 99: 674-676 (variants NF1 Arg-844 and Pro-898); Hudson et al. *Hum. Mutat.* 1997; 9: 366-367 (variant NF1 Arg-1952); Upadhyaya et al. *Hum. Mutat.* 1997; 10: 248-250 (variants NF1 GLY-338 and TRP-1611); Klose et al. *Hum. Mol. Genet.* 1998; 7: 1261-1268 (variant NF1 Pro-1276); Krkljus et al. *Hum. Mutat.* 1998; 11: 411-411 (variant NF1 Gly-1204, variant His-765); Messiaen et al. *Genet. Med.* 1999; 1: 248-253 (variant NF1 Pro-508); Peters et al. *Hum. Mutat.* 1999; 13: 337-337 (variant NF1 Pro-1446); Fahsold et al. *Am. J. Hum. Genet.* 2000; 66: 790-818 (variants NF1 Pro-216; Pro-357; Cys-491; Pro-549; Thr-581; Arg-583; Phe-665; Pro-695; Pro-763; Ser-777; Lys-780; Pro-781; Pro-847; Ser-1156; Pro-1250; Gln-1276; Pro-1276; Pro-1446; Val-1605 and Ile-2507, variant Glu-176); Ars et al. *Hum. Mol. Genet.* 2000; 9: 237-247 (variants NF1 Ser-117; Trp-1204; Pro-1446 and 2387-Asn-Phe-2388 del), Erratum Ars et al. *Hum. Mol. Genet.* 2000; 9:659-659; Boulandet et al. *Hum. Mutat.* 2000; 16: 274-275 (variant NF1 Phe-844); Kaufmann et al. *Am. J. Hum. Genet.* 2001; 69: 1395-1400 (variant spinal FSNF Pro-2088); Han et al. *Hum. Genet.* 2001; 109:487-497 (variants NF1 Lys-780; Cys-784; Pro-1147; Cys-1193; Arg-1444; Ser-1785; Asn-2012 and Lys-2357); Kluwe et al. *Hum. Mutat.* 2002; 19:309-309 (variants NF1 Phe-82; Arg-784 and Glu-1444); Baralle et al. *Am. J. Med. Genet. A* 2003; 119:1-8 (variant NFNS Glu-1459 del); Wang et al. *Hum. Genet.* 2003; 112: 117-123 (variants NF1 Tyr-93; Val-604; Arg-844 and Pro-898, Variants Asp-74; Glu-176; Arg-712 and Gln-1276); De Luca et al. *Hum. Mutat.* 2003; 21: 171-172 (variants NF1 Lys-780; Pro-847; Glu-848 And Arg-968; Asn-1444; Leu-1953 del and Arg-2001); Kluwe et al. *J. Med. Genet.* 2003; 40: 368-371 (variants NF1 Arg-578; Pro-920 and Ala-2221); Zatkova et al. *Hum. Mutat.* 24:491-501 (variant NF1 Val-186, characterization of variant NF1 Val-186); De Luca et al. *Hum. Mutat.* 2004; 23: 629-629 (variants NF1 Asn-157; Arg-629; Ser-777; Lys-780; Arg-784; Pro-847; Glu-848; Arg-968; Asn-1444; Leu-1953 del and Arg-2001, variant Glu-176); Mattocks et al. *J. Med. Genet.* 2004; 41: E48-E48 (variants NF1 Arg-31; Pro-145; Arg-324; Val-337; Cys-489; Pro-532; Arg-574; Arg-629; Phe-665; Phe-844; Pro-844; Met-991 del; Val-1073; Arg-1196; Gly-1276; Gln-1276; Glu-1430; Glu-1459 del and Gly-1489, variants Glu-176 and Cys-873); Ferner et al. *J. Med. Genet.* 2004; 41: 837-841 (variant NF1 Pro-1243); Bertola et al. *Am. J. Med. Genet. A* 2005; 136: 242-245 (variant NF1 Arg-844); De Luca et al. *Am. J. Hum. Genet.* 2005; 77: 1092-1101 (variants NFNS Arg-194; Glu-1444; Thr-1451; Leu-1453 and Glu-1459 del); Sjoeblom et al. *Science.* 2006; 314:268-274 (variants Ile-1187; Leu-1951 and Arg-2745); Upadhyaya et al. *Am. J. Hum. Genet.* 2007; 80: 140-151 (variant NF1 Met-991 del); Nystrom et al. *Clin. Genet.* 76:524-534 (variant NFNS Phe-1411); Ponti et al. *Hered. Cancer Clin. Pract.* 2011; 9: 6-6 (variant NF1

Thr-160); Thomas et al. *Eur. J. Hum. Genet.* 2012; 20: 411-419 (variants Glu-176; Thr-330; Asp-393; Leu-393; Pro-519; Thr-776 and Phe-1484); Nemethova et al. *Ann. Hum. Genet.* 2013; 77: 364-379 (variants Nf1 Trp-93; Arg-1048; Arg-1189; Arg-1661 (isoform 1) and Thr-1918 (isoform 1); and Ben-Salem et al. *Childs Nerv. Syst.* 2014; 30: 1183-1189 (variant NF1 Pro-2125).

Low Density Lipoprotein Receptor-Related Protein 1B (LRP1B)

The invention described herein includes, e.g., determining the number of an alteration (e.g., a somatic alteration) in an LRP1B gene, or measuring the mutation load, e.g., by determining the number of an alteration (e.g., a somatic alteration) in an LRP1B gene.

The Low Density Lipoprotein Receptor-Related Protein 1B (LRP1B) gene, which is also known as LRP-DIT, LRP-1B, or LRPDIT, belongs to the low density lipoprotein (LDL) receptor gene family. These receptors play a wide variety of roles in normal cell function and development due to their interactions with multiple ligands.

The nucleotide and amino acid sequences of human LRP1B are described, e.g., in Liu et al. *Cancer Res.* 2000; 60:1961-1967; Lie et al. Genomics 2000; 69: 271-274.

Evaluation of Subjects

Subjects, e.g., patients, can be evaluated for a responder status to a therapy described herein, e.g, a cancer immunotherapy, e.g., a therapy comprising an inhibitor of PD-1 or PD-L1. For example, the evaluation can include determining the mutation load in a cancer, e.g., a cancer described herein, and/or the presence of an alteration, e.g., an alteration as described herein or an alteration in a gene described herein. A patient can be evaluated, for example, by acquiring knowledge of the mutation load in a tumor sample from the patient. Alternatively, or in addition, a patient can be evaluated, for example, by determining the genomic sequence of the patient, e.g., by an NGS method. Alternatively, or in addition, evaluation of a patient can include directly assaying for the presence of a mutation in the patient, such as by an assay to detect a mutated nucleic acid (e.g., DNA or RNA), such as by, Southern blot, Northern blot, or RT-PCR, e.g., qRT-PCR. Alternatively, or in addition, a patient can be evaluated for the presence of a protein mutation, such as by immunohistochemistry, Western blot, immunoprecipitation, or immunomagnetic bead assay.

In one aspect, the results of a clinical trial, e.g., a successful or unsuccessful clinical trial, can be repurposed to identify agents for treating cancer, e.g., in a subset patient population. By one exemplary method, a candidate agent used in a clinical trial can be reevaluated to determine if the agent in the trial is effective to treat a tumor having a particular level of mutation load or containing a particular mutation. For example, subjects who participated in a clinical trial for an agent, such as an immune checkpoint modulator, can be identified. Patients who experienced an improvement in symptoms, e.g., cancer (e.g., a melanoma) symptoms, such as decreased tumor size, or decreased rate of tumor growth, can be evaluated for the mutation load and/or the presence of a mutation. Patients who did not experience an improvement in cancer symptoms can also be evaluated for the mutation load and/or the presence of a mutation. In an embodiment, where patients having a predetermined level of mutation load in a tumor sample are found to have been more likely to respond to the test agent than patients who do not have such a predetermined level of mutation load, then the agent is determined to be an appropriate treatment option for a patient having the predetermined level of mutation load. In another embodiment, where patients carrying a mutation are found to have been more likely to respond to the test agent than patients who did not carry such a mutation, then the agent is determined to be an appropriate treatment option for a patient carrying the mutation.

"Reevaluation" of patients can include, for example, acquiring knowledge of the mutation load in a tumor sample, e.g., a melanoma sample, from the subject. Alternatively, or in addition, reevaluation of the patients can include determining the genomic sequence of the patients, or a subset of the clinical trial patients, e.g., by an NGS method. Alternatively, or in addition, reevaluation of the patients can include directly assaying for the presence of a mutation in the patient, such as by an assay to detect a mutated nucleic acid (e.g., RNA), such as by RT-PCR, e.g., qRT-PCR. Alternatively, or in addition, a patient can be reevaluated for the presence of a protein mutation, such as by immunohistochemistry, Western blot, immunoprecipitation, or immunomagnetic bead assay.

Methods for Detection of Nucleic Acids and Polypeptides

Methods for evaluating an altered gene, mutations and/or gene products are known to those of skill in the art. In one embodiment, the alteration (e.g., mutation) is detected in a nucleic acid molecule by a method chosen from one or more of: nucleic acid hybridization assay, selective suppression of PCR (SSP), HPLC or mass-spectrometric genotyping.

Additional exemplary methods include traditional "direct probe" methods such as Southern blots and "comparative probe" methods such as comparative genomic hybridization (CGH), e.g., cDNA-based or oligonucleotide-based CGH, can be used. The methods can be used in a wide variety of formats including, but not limited to, substrate (e.g., membrane or glass) bound methods or array-based approaches.

In certain embodiments, the evaluation methods include probes/primers against the alterations described herein.

In one embodiment, probes/primers can be designed to detect a mutation or a reciprocal thereof. These probes/primers are suitable, e.g., for PCR amplification. Probes are used that contain DNA segments that are essentially complementary to DNA base sequences existing in different portions of chromosomes. Examples of probes useful according to the invention, and labeling and hybridization of probes to samples are described in two U.S. patents to Vysis, Inc. U.S. Pat. Nos. 5,491,224 and 6,277,569 to Bittner, et al.

Chromosomal probes are typically about 50 to about $10^5$ nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromosome) along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic Histochem., 1998, 73(1):6-22, Wheeless et al., Cytometry 1994, 17:319-326, and U.S. Pat. No. 5,491,224.

The probes to be used hybridize to a specific region of a chromosome to determine whether a cytogenetic abnormality is present in this region. One type of cytogenetic abnormality is a deletion. Although deletions can be of one or more entire chromosomes, deletions normally involve loss of part of one or more chromosomes. If the entire region of a chromosome that is contained in a probe is deleted from a cell, hybridization of that probe to the DNA from the cell will normally not occur and no signal will be present on that chromosome. If the region of a chromosome that is partially contained within a probe is deleted from a cell, hybridization of that probe to the DNA from the cell can still occur, but less of a signal can be present. For example, the loss of a signal is compared to probe hybridization to DNA from control cells that do not contain the genetic abnormalities which the probes are intended to detect. In some embodiments, at least 1, 5, 10, 20, 30, 40, 50, 60, 70, 80, 90, 100, 110, 120, 130, 140, 150, 160, 170, 180, 190, 200, or more cells are enumerated for the presence of the cytogenetic abnormality.

Cytogenetic abnormalities to be detected can include, but are not limited to, non-reciprocal translocations, balanced translocations, intra-chromosomal inversions, point mutations, deletions, gene copy number changes, gene expression level changes, and germ line mutations. In particular, one type of cytogenetic abnormality is a duplication. Duplications can be of entire chromosomes, or of regions smaller than an entire chromosome. If the region of a chromosome that is contained in a probe is duplicated in a cell, hybridization of that probe to the DNA from the cell will normally produce at least one additional signal as compared to the number of signals present in control cells with no abnormality of the chromosomal region contained in the probe.

Chromosomal probes are labeled so that the chromosomal region to which they hybridize can be detected. Probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

U.S. Pat. No. 5,491,224 describes probe labeling as a number of the cytosine residues having a fluorescent label covalently bonded thereto. The number of fluorescently labeled cytosine bases is sufficient to generate a detectable fluorescent signal while the individual so labeled DNA segments essentially retain their specific complementary binding (hybridizing) properties with respect to the chromosome or chromosome region to be detected. Such probes are made by taking the unlabeled DNA probe segment, transaminating with a linking group a number of deoxycytidine nucleotides in the segment, or covalently bonding a fluorescent label to at least a portion of the transaminated deoxycytidine bases.

Probes can also be labeled by nick translation, random primer labeling or PCR labeling. Labeling is done using either fluorescent (direct)—or haptene (indirect)—labeled nucleotides. Representative, non-limiting examples of labels include: AMCA-6-dUTP, CascadeBlue-4-dUTP, Fluorescein-12-dUTP, Rhodamine-6-dUTP, TexasRed-6-dUTP, Cy3-6-dUTP, Cy5-dUTP, Biotin (BIO)-11-dUTP, Digoxygenin (DIG)-11-dUTP or Dinitrophenyl (DNP)-11-dUTP.

Probes also can be indirectly labeled with biotin or digoxygenin, or labeled with radioactive isotopes such as $^{32}P$ and $^{3}H$, although secondary detection molecules or further processing then is required to visualize the probes. For example, a probe labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Probes can also be prepared such that a fluorescent or other label is not part of the DNA before or during the hybridization, and is added after hybridization to detect the probe hybridized to a chromosome. For example, probes can be used that have antigenic molecules incorporated into the DNA. After hybridization, these antigenic molecules are detected using specific antibodies reactive with the antigenic molecules. Such antibodies can themselves incorporate a fluorochrome, or can be detected using a second antibody with a bound fluorochrome.

However treated or modified, the probe DNA is commonly purified in order to remove unreacted, residual products (e.g., fluorochrome molecules not incorporated into the DNA) before use in hybridization.

Prior to hybridization, chromosomal probes are denatured according to methods well known in the art. Probes can be hybridized or annealed to the chromosomal DNA under hybridizing conditions. "Hybridizing conditions" are conditions that facilitate annealing between a probe and target chromosomal DNA. Since annealing of different probes will vary depending on probe length, base concentration and the like, annealing is facilitated by varying probe concentration, hybridization temperature, salt concentration and other factors well known in the art.

Hybridization conditions are facilitated by varying the concentrations, base compositions, complexities, and lengths of the probes, as well as salt concentrations, temperatures, and length of incubation. For example, in situ hybridizations are typically performed in hybridization buffer containing 1-2×SSC, 50-65% formamide and blocking DNA to suppress non-specific hybridization. In general, hybridization conditions, as described above, include temperatures of about 25° C. to about 55° C., and incubation lengths of about 0.5 hours to about 96 hours.

Non-specific binding of chromosomal probes to DNA outside of the target region can be removed by a series of washes. Temperature and concentration of salt in each wash are varied to control stringency of the washes. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes. In some applications it is necessary to block the hybridization capacity of repetitive sequences. Thus, in some embodiments, tRNA, human genomic DNA, or Cot-I DNA is used to block non-specific hybridization. After washing, the slide is allowed to drain and air dry, then mounting medium, a counterstain such as DAPI, and a coverslip are applied to the slide. Slides can be viewed immediately or stored at −20° C. before examination.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH can also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays.

Hybridization protocols suitable for use with the methods featured in the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology, Vol.* 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used. Array-based CGH is described in U.S. Pat. No. 6,455,258, the contents of which are incorporated herein by reference.

In still another embodiment, amplification-based assays can be used to measure presence/absence and copy number. In such amplification-based assays, the nucleic acid sequences act as a template in an amplification reaction (e.g., Polymerase Chain Reaction (PCR)). In a quantitative amplification, the amount of amplification product will be proportional to the amount of template in the original sample. Comparison to appropriate controls, e.g., healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR can also be used. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Nucleic Acid Samples

A variety of tissue samples can be the source of the nucleic acid samples used in the present methods. Genomic or subgenomic DNA fragments can be isolated from a subject's sample (e.g., a tumor sample, a normal adjacent tissue (NAT), a blood sample or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. The isolating step can include flow-sorting of individual chromosomes; and/or micro-dissecting a subject's sample (e.g., a tumor sample, a NAT, a blood sample). In certain embodiments, the sample comprises circulating tumor DNA (ctDNA).

Protocols for DNA isolation, fragmentation and processing from a tissue sample are known in the art as described, e.g., in WO 2012/092426, entitled "Optimization of Multigene Analysis of Tumor Samples," incorporated herein by reference in its entirety. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429; Ambion RecoverAll™ Total Nucleic Acid Isolation Protocol (Ambion, Cat. No. AM1975, September 2008); and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. QIAamp® DNA FFPE Tissue Kit uses QIAamp® DNA Micro technology for purification of genomic and mitochondrial DNA.

Design of Baits

A bait can be a nucleic acid molecule, e.g., a DNA or RNA molecule, which can hybridize to (e.g., be complementary to), and thereby allow capture of a target nucleic acid. In one embodiment, a bait is an RNA molecule. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

Baits can be produced and used by methods and hybridization conditions as described in US 2010/0029498, Gnirke, A. et al. (2009) *Nat Biotechnol.* 27(2):182-189, and WO 2012/092426, entitled "Optimization of Multigene Analysis of Tumor Samples, which are each incorporated herein by reference.

Sequencing

The invention also includes methods of sequencing nucleic acids. In one embodiment, any of a variety of sequencing reactions known in the art can be used to directly sequence at least a portion of a mutation. In one embodiment, the mutated sequence is compared to a corresponding reference (control) sequence.

In one embodiment, the sequence of the nucleic acid molecule comprising an alteration described herein is determined by a method that includes one or more of: hybridizing an oligonucleotide, e.g., an allele specific oligonucleotide for one mutation described herein to said nucleic acid molecule; hybridizing a primer, or a primer set (e.g., a primer pair), that amplifies a region comprising the mutation of the allele; amplifying, e.g., specifically amplifying, a region comprising the mutation of the allele; attaching an adapter oligonucleotide to one end of a nucleic acid that comprises the mutation of the allele; generating an optical, e.g., a colorimetric signal, specific to the presence of the mutation; hybridizing a nucleic acid comprising the mutation to a second nucleic acid, e.g., a second nucleic acid attached to a substrate; generating a signal, e.g., an electrical or fluorescent signal, specific to the presence of the mutation; and incorporating a nucleotide into an oligonucleotide that is hybridized to a nucleic acid that contains the mutation.

In another embodiment, the sequence is determined by a method that comprises one or more of: determining the nucleotide sequence from an individual nucleic acid molecule, e.g., where a signal corresponding to the sequence is derived from a single molecule as opposed, e.g., from a sum of signals from a plurality of clonally expanded molecules; determining the nucleotide sequence of clonally expanded proxies for individual nucleic acid molecules; massively parallel short-read sequencing; template-based sequencing; pyrosequencing; real-time sequencing comprising imaging the continuous incorporation of dye-labeling nucleotides during DNA synthesis; nanopore sequencing; sequencing by hybridization; nano-transistor array based sequencing; polony sequencing; scanning tunneling microscopy (STM) based sequencing; or nanowire-molecule sensor based sequencing.

Any method of sequencing known in the art can be used. Exemplary sequencing reactions include those based on techniques developed by Maxam and Gilbert (*Proc. Natl Acad Sci USA* (1977) 74:560) or Sanger (Sanger et al. (1977) *Proc. Nat. Acad. Sci* 74:5463). Any of a variety of automated sequencing procedures can be utilized when performing the assays (*Biotechniques* (1995) 19:448), including sequencing by mass spectrometry (see, for example, U.S. Pat. No. 5,547,835 and international patent application Publication Number WO 94/16101, entitled DNA Sequencing by Mass Spectrometry by H. Köster; U.S. Pat. No. 5,547,835 and international patent application Publication Number WO 94/21822 entitled DNA Sequencing by Mass Spectrometry Via Exonuclease Degradation by H. Köster), and U.S. Pat. No. 5,605,798 and International Patent Application No. PCT/US96/03651 entitled DNA Diagnostics Based on Mass Spectrometry by H. Köster; Cohen et al. (1996) *Adv Chromatogr* 36:127-162; and Griffin et al. (1993) *Appl Biochem Biotechnol* 38:147-159).

Sequencing of nucleic acid molecules can also be carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference.

In one embodiment, the next-generation sequencing allows for the determination of the nucleotide sequence of an individual nucleic acid molecule (e.g., Helicos BioSciences' HeliScope Gene Sequencing system, and Pacific Biosciences' PacBio RS system). In other embodiments, the sequencing method determines the nucleotide sequence of clonally expanded proxies for individual nucleic acid molecules (e.g., the Solexa sequencer, Illumina Inc., San Diego, Calif.; 454 Life Sciences (Branford, Conn.), and Ion Torrent). e.g., massively parallel short-read sequencing (e.g., the Solexa sequencer, Illumina Inc., San Diego, Calif.), which generates more bases of sequence per sequencing unit than other sequencing methods that generate fewer but longer reads. Other methods or machines for next-generation sequencing include, but are not limited to, the sequencers provided by 454 Life Sciences (Branford, Conn.), Applied Biosystems (Foster City, Calif.; SOLiD sequencer), and Helicos BioSciences Corporation (Cambridge, Mass.).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system. NGS technologies can include one or more of steps, e.g., template preparation, sequencing and imaging, and data analysis as described in WO 2012/092426, entitled "Optimization of Multigene Analysis of Tumor Samples, incorporated herein by reference.

Various types of alterations, e.g., somatic alterations and germline mutations, can be detected by a method (e.g., a sequencing method) described herein. In certain embodiments, a germline mutation is further identified by a method using the SGZ algorighm. The SGZ algorithm is described in International Application Publication No. WO2014/183078 and U.S. Application Publication No. 2014/0336996, the contents of which are incorporated by reference in their entirety.

Data Analysis

After NGS reads have been generated, they can be aligned to a known reference sequence or assembled de novo.

For example, identifying genetic variations such as single-nucleotide polymorphism and structural variants in a sample (e.g., a tumor sample) can be accomplished by aligning NGS reads to a reference sequence (e.g., a wild-type sequence). Methods of sequence alignment for NGS are described e.g., in Trapnell C. and Salzberg S. L. *Nature Biotech.*, 2009, 27:455-457. Examples of de novo assemblies are described, e.g., in Warren R. et al., *Bioinformatics*, 2007, 23:500-501; Butler J. et al., *Genome Res.*, 2008, 18:810-820; and Zerbino D. R. and Birney E., *Genome Res.*, 2008, 18:821-829. Sequence alignment or assembly can be performed using read data from one or more NGS platforms, e.g., mixing Roche/454 and Illumina/Solexa read data. Algorithms and methods for data analysis are described in WO 2012/092426, entitled "Optimization of Multigene Analysis of Tumor Samples, incorporated herein by reference.

Reporting

Methods described herein can include providing a report, such as, in electronic, web-based, or paper form, to the patient or to another person or entity, e.g., a caregiver, e.g., a physician, e.g., an oncologist, a hospital, clinic, third-party payor, insurance company or government office. The report can include output from the method, e.g., the identification of a value of responder status to a therapy, the identification of a value for mutation load, the identification of the number of an alteration in a gene described herein, and/or the indication of the presence or absence of an alteration described herein, or wildtype sequence. In one embodiment, a report is generated, such as in paper or electronic form, which identifies the value of responder status to a therapy, the value for mutation load, the number of an alteration in a gene described herein, or the presence or absence of an alteration described herein, and optionally includes an identifier for the patient from whom the value, the number, or the sequence containing the alteration was obtained.

The report can also include information on the role of an alteration as described herein, or wildtype sequence, in a cancer, e.g., a melanoma. Such information can include information on prognosis, resistance, or potential or suggested therapeutic options, e.g., an agent as described herein, e.g., a cancer therapy (e.g., a cancer immunotherapy, e.g., an inhibitor of PD-1 or PD-L1). The report can include information on the likely effectiveness of a therapeutic option, the acceptability of a therapeutic option, or the advisability of applying the therapeutic option to a patient, e.g., a patient having a predetermined value of responder status to a therapy, a predetermined level of mutation load, a predetermined number of an alteration in a gene described herein, or a sequence, alteration or mutation identified in the test, and in embodiments, identified in the report. For example, the report can include information, or a recommendation on, the administration of a drug, e.g., the administration at a preselected dosage or in a preselected treatment regimen, e.g., in combination with other drugs, to the patient. In one embodiment, not all mutations identified in the method are identified in the report. For example, the report can be limited to mutations in genes having a preselected level of correlation with the occurrence, prognosis, stage, or susceptibility of the cancer to treatment, e.g., with a preselected therapeutic option. The report can be delivered, e.g., to an entity described herein, within 7, 14, or 21 days from receipt of the sample by the entity practicing the method.

In another aspect, the invention features a method for generating a report, e.g., a personalized cancer treatment report, by obtaining a sample, e.g., a tumor sample (e.g., a melanoma sample), from a subject, acquiring a value of responder status to a therapy, determining mutation load in the sample, determining the number of an alteration in a gene, or detecting a mutation as described herein in the sample, and selecting a treatment based on the value of responder status to a therapy, the value for mutation load, the number of alterations in the gene, or the mutation detected. In one embodiment, a report is generated that annotates the selected treatment, or that lists, e.g., in order of preference, two or more treatment options based on the value of responder status to a therapy, the value for mutation load, the number of alterations in the gene, or the mutation detected. In another embodiment, the subject, e.g., a patient, is further administered the selected method of treatment.

Kits

In one aspect, the invention features, a kit, e.g., containing an oligonucleotide having an alteration described herein, e.g., an alteration in a gene described herein. Optionally, the kit can also contain an oligonucleotide that is the wildtype counterpart of the mutant oligonucleotide.

In certain embodiments, the kit comprises:

(a) one or more detection reagents, capable of detecting one or more of:
 (i) a somatic alteration in a predetermined set of genes set forth in Table 1,
 (ii) a somatic alteration in an NF1 gene,
 (iii) a somatic alteration in an LRP1B gene, or
 (iv) a C to T transition; and
(b) instructions for use in determining the mutation load in a melanoma sample and/or the presence or absence of one or more of the aforesaid alterations.

In some embodiments, the kit further comprises an inhibitor of PD-1 or PD-L1 or a composition thereof. In some embodiments, the kit further instructions for use in treating a melanoma in a subject.

A kit can include a carrier, e.g., a means being compartmentalized to receive in close confinement one or more container means. In one embodiment the container contains an oligonucleotide, e.g., a primer or probe as described above. The components of the kit are useful, for example, to diagnose or identify a mutation in a tumor sample in a patient. The probe or primer of the kit can be used in any sequencing or nucleotide detection assay known in the art, e.g., a sequencing assay, e.g., an NGS method, RT-PCR, or in situ hybridization.

In some embodiments, the components of the kit are useful, for example, to diagnose or identify a mutation and/or to evaluate mutation load in a tumor sample in a patient, and to accordingly identify an appropriate therapeutic agent to treat the cancer.

A kit featured in the invention can include, e.g., assay positive and negative controls, nucleotides, enzymes (e.g., RNA or DNA polymerase or ligase), solvents or buffers, a stabilizer, a preservative, a secondary antibody, e.g., an anti-HRP antibody (IgG) and a detection reagent.

An oligonucleotide can be provided in any form, e.g., liquid, dried, semi-dried, or lyophilized, or in a form for storage in a frozen condition.

Typically, an oligonucleotide, and other components in a kit are provided in a form that is sterile. An oligonucleotide, e.g., an oligonucleotide that contains a mutation described herein, or an oligonucleotide complementary to an alteration described herein, is provided in a liquid solution, the liquid solution generally is an aqueous solution, e.g., a sterile aqueous solution. When the oligonucleotide is provided as a dried form, reconstitution generally is accomplished by the addition of a suitable solvent. The solvent, e.g., sterile buffer, can optionally be provided in the kit.

The kit can include one or more containers for the composition containing an oligonucleotide in a concentration suitable for use in the assay or with instructions for dilution for use in the assay. In some embodiments, the kit contains separate containers, dividers or compartments for the oligonucleotide and assay components, and the informational material. For example, the oligonucleotides can be contained in a bottle or vial, and the informational material can be contained in a plastic sleeve or packet. In other embodiments, the separate elements of the kit are contained within a single, undivided container. For example, an oligonucleotide composition is contained in a bottle or vial that has attached thereto the informational material in the form of a label. In some embodiments, the kit includes a plurality (e.g., a pack) of individual containers, each containing one or more unit forms (e.g., for use with one assay) of an oligonucleotide. For example, the kit includes a plurality of ampoules, foil packets, or blister packs, each containing a single unit of oligonucleotide for use in sequencing or detecting a mutation in a tumor sample. The containers of the kits can be air tight and/or waterproof. The container can be labeled for use.

For antibody-based kits, the kit can include: (1) a first antibody (e.g., attached to a solid support) which binds to a mutated polypeptide; and, optionally, (2) a second, different antibody which binds to either the polypeptide or the first antibody and is conjugated to a detectable agent.

In one embodiment, the kit can include informational material for performing and interpreting the sequencing or diagnostic. In another embodiment, the kit can provide guidance as to where to report the results of the assay, e.g., to a treatment center or healthcare provider. The kit can include forms for reporting the results of a sequencing or diagnostic assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with a particular chemotherapeutic drug, depending on the results of the assay.

The informational material of the kits is not limited in its form. In many cases, the informational material, e.g., instructions, is provided in printed matter, e.g., a printed text, drawings, and/or photographs, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about the sequencing or diagnostic assay and/or its use in the methods described herein. The informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a blood or tissue sample, e.g., a biopsy sample, and evaluates the sample using an assay described herein, e.g., a sequencing assay or in situ hybridization assay, and determines that the sample contains a mutation. The assay provider, e.g., a service provider or healthcare provider, can then conclude that the subject is, or is not, a candidate for a particular drug or a particular cancer treatment regimen.

Detection Reagents

In another aspect, the invention features a detection reagent, e.g., a purified or an isolated preparation thereof. Detection reagents can distinguish a nucleic acid, or protein sequence, having an alteration described herein, e.g., of a nucleic acid molecule comprising an alteration described herein, e.g., a somatic alteration in a predetermined set of genes set forth in Table 1; a somatic alteration in an NF1 gene; a somatic alteration in an LRP1B gene; or a C to T transition.

Detection reagents, e.g., nucleic acid-based detection reagents, can be used to identify mutations in a target nucleic acid, e.g., DNA, e.g., genomic DNA or cDNA, or RNA, e.g., in a sample, e.g., a sample of nucleic acid acquired or derived from a melanoma, e.g., an advanced or metastatic melanoma. Detection reagents, e.g., antibody-based detection reagents, can be used to identify mutations in a target protein, e.g., in a sample, e.g., a sample of protein acquired or derived from, or produced by, a melanoma cell, e.g., an advanced or metastatic melanoma cell.

In one embodiment, the detection reagent comprises a nucleic acid molecule, e.g., a DNA, RNA or mixed DNA/RNA molecule, comprising sequence which is complementary with a nucleic acid sequence on a target nucleic acid (the sequence on the target nucleic acid that is bound by the detection reagent is referred to herein as the "detection reagent binding site" and the portion of the detection reagent that corresponds to the detection reagent binding site is referred to as the "target binding site"). In one embodiment, the detection reagent binding site is disposed in relationship to the interrogation position such that binding (or in embodiments, lack of binding) of the detection reagent to the detection reagent binding site allows differentiation of mutant and reference sequences for a mutant described herein (nucleic acid molecule comprising an alteration described herein, e.g., a somatic alteration in a predetermined set of genes set forth in Table 1; a somatic alteration in an NF1 gene; a somatic alteration in an LRP1B gene; and/or a C to T transition. The detection reagent can be modified, e.g., with a label or other moiety, e.g., a moiety that allows capture.

In one embodiment, the detection reagent comprises a nucleic acid molecule, e.g., a DNA, RNA or mixed DNA/RNA molecule, which, e.g., in its target binding site, includes the interrogation position and which can distinguish (e.g., by affinity of binding of the detection reagent to a target nucleic acid or the ability for a reaction, e.g., a ligation or extension reaction with the detection reagent) between a mutation, e.g., an alteration described herein, and a reference sequence. In embodiments, the interrogation position can correspond to a terminal, e.g., to a 3' or 5' terminal nucleotide, a nucleotide immediately adjacent to a 3' or 5' terminal nucleotide, or to another internal nucleotide, of the detection reagent or target binding site.

In embodiments, the difference in the affinity of the detection reagent for a target nucleic acid comprising the alteration described herein and that for a target nucleic acid comprising the reference sequence allows determination of the presence or absence of the mutation (or reference) sequence. Typically, such detection reagents, under assay conditions, will exhibit substantially higher levels of binding only to the mutant or only to the reference sequence, e.g., will exhibit substantial levels of binding only to the mutation or only to the reference sequence.

In embodiments, binding allows (or inhibits) a subsequent reaction, e.g., a subsequent reaction involving the detection reagent or the target nucleic acid. E.g., binding can allow ligation, or the addition of one or more nucleotides to a nucleic acid, e.g., the detection reagent, e.g., by DNA polymerase, which can be detected and used to distinguish mutant from reference. In embodiments, the interrogation position is located at the terminus, or sufficiently close to the terminus, of the detection reagent or its target binding site, such that hybridization, or a chemical reaction, e.g., the addition of one or more nucleotides to the detection reagent, e.g., by DNA polymerase, only occurs, or occurs at a substantially higher rate, when there is a perfect match between the detection reagent and the target nucleic acid at the interrogation position or at a nucleotide position within 1, 2, or 3 nucleotides of the interrogation position.

In one embodiment, the detection reagent comprises a nucleic acid, e.g., a DNA, RNA or mixed DNA/RNA molecule wherein the molecule, or its target binding site, is adjacent (or flanks), e.g., directly adjacent, to the interrogation position, and which can distinguish between a mutation described herein, and a reference sequence, in a target nucleic acid.

In embodiments, the detection reagent binding site is adjacent to the interrogation position, e.g., the 5' or 3' terminal nucleotide of the detection reagent, or its target binding site, is adjacent, e.g., between 0 (directly adjacent) and 1,000, 500, 400, 200, 100, 50, 10, 5, 4, 3, 2, or 1 nucleotides from the interrogation position. In embodiments, the outcome of a reaction will vary with the identity of the nucleotide at the interrogation position allowing one to distinguish between mutant and reference sequences. E.g., in the presence of a first nucleotide at the interrogation position a first reaction will be favored over a second reaction. E.g., in a ligation or primer extension reaction, the product will differ, e.g., in charge, sequence, size, or susceptibility to a further reaction (e.g., restriction cleavage) depending on the identity of the nucleotide at the interrogation position. In embodiments the detection reagent comprises paired molecules (e.g., forward and reverse primers), allowing for amplification, e.g., by PCR amplification, of a duplex containing the interrogation position. In such embodiments, the presence of the mutation can be determined by a difference in the property of the amplification product, e.g., size, sequence, charge, or susceptibility to a reaction, resulting from a sequence comprising the interrogation position and a corresponding sequence having a reference nucleotide at the interrogation positions. In embodiments, the presence or absence of a characteristic amplification product is indicative of the identity of the nucleotide at the interrogation site and thus allows detection of the mutation.

In embodiments, the detection reagent, or its target binding site, is directly adjacent to the interrogation position, e.g., the 5' or 3' terminal nucleotide of the detection reagent is directly adjacent to the interrogation position. In embodiments, the identity of the nucleotide at the interrogation position will determine the nature of a reaction, e.g., a reaction involving the detection reagent, e.g., the modification of one end of the detection reagent. E.g., in the presence of a first nucleotide at the interrogation position a first reaction will be favored over a second reaction. By way of example, the presence of a first nucleotide at the interrogation position, e.g., a nucleotide associated with a mutation, can promote a first reaction, e.g., the addition of a complementary nucleotide to the detection reagent. By way of example, the presence of an A at the interrogation position will cause the incorporation of a T, having, e.g., a first colorimetric label, while the presence of a G and the interrogation position will cause the incorporation of a C, having, e.g., a second colorimetric label. In one embodiment, the presence of a first nucleotide at the position will result in ligation of the detection reagent to a second nucleic acid. E.g., a third nucleic acid can be hybridized to the target nucleic acid sufficiently close to the interrogation site if the third nucleic acid has an exact match at the interrogation site it will be ligated to the detection reagent. Detection of the ligation product, or its absence, is indicative of the identity of the nucleotide at the interrogation site and thus allows detection of the mutation.

A variety of readouts can be employed. E.g., binding of the detection reagent to the mutant or reference sequence can be followed by a moiety, e.g., a label, associated with the detection reagent, e.g., a radioactive or enzymatic label. In embodiments the label comprises a quenching agent and a signaling agent and hybridization results in altering the distance between those two elements, e.g., increasing the distance and un-quenching the signaling agent. In embodiments, the detection reagent can include a moiety that allows separation from other components of a reaction mixture. In embodiments, binding allows cleavage of the bound detection reagent, e.g., by an enzyme, e.g., by the nuclease activity of the DNA polymerase or by a restriction enzyme. The cleavage can be detected by the appearance or disappearance of a nucleic acid or by the separation of a quenching agent and a signaling agent associated with the detection reagent. In embodiments, binding protects, or renders the target susceptible, to further chemical reaction, e.g., labeling or degradation, e.g., by restriction enzymes. In embodiments binding with the detection reagent allows capture, separation or physical manipulation of the target nucleic acid to thereby allow for identification. In embodiments binding can result in a detectable localization of the detection reagent or target, e.g., binding could capture the target nucleic acid or displace a third nucleic acid. Binding can allow for the extension or other size change in a component, e.g., the detection reagent, allowing distinction between mutant and reference sequences. Binding can allow for the production, e.g., by PCR, of an amplicon that distinguishes mutant from reference sequence.

In one embodiment the detection reagent, or the target binding site, is between 5 and 500, 5 and 300, 5 and 250, 5 and 200, 5 and 150, 5 and 100, 5 and 50, 5 and 25, 5 and 20, 5 and 15, or 5 and 10 nucleotides in length. In one embodiment the detection reagent, or the target binding site, is between 10 and 500, 10 and 300, 10 and 250, 10 and 200, 10 and 150, 10 and 100, 10 and 50, 10 and 25, 10 and 20, or 10 and 15, nucleotides in length. In one embodiment the detection reagent, or the target binding site, is between 20 and 500, 20 and 300, 20 and 250, 20 and 200, 20 and 150, 20 and 100, 20 and 50, or 20 and 25 nucleotides in length. In one embodiment the detection reagent, or the target binding site, is sufficiently long to distinguish between mutant and reference sequences and is less than 100, 200, 300, 400, or 500 nucleotides in length.

A mutant protein described herein can be distinguished from a reference, e.g., a non-mutant or wild-type protein, by reaction with a reagent, e.g., a substrate, e.g., a substrate for catalytic activity or functional activity, or an antibody, that reacts differentially with the mutant and reference protein. In one aspect, the invention includes a method of contacting a sample having a predetermined level of mutation load and/or comprising a mutant protein described herein with such reagent and determining if the mutant protein is present in the sample.

In one embodiment of the reaction mixture, or the method of making the reaction mixture, the detection reagent comprises a probe or primer specific for a nucleic acid containing an alteration described herein, or an antibody specific for a mutant protein described herein. In one embodiment of the reaction mixture, or the method of making the reaction mixture, the alteration is a somatic alteration in a gene described herein, e.g., a gene described in Table 1, e.g., an NF1 gene or an LRP1B gene.

Preparations of Nucleic Acids and Uses Thereof

In another aspect, the invention features purified or isolated preparations of a neoplastic or tumor cell nucleic acid, e.g., DNA, e.g., genomic DNA or cDNA, or RNA, containing an interrogation position described herein, useful for determining the mutation load of a sample or the presence or absence of an alteration disclosed. The nucleic acid includes the interrogation position, and typically additional sequence on one or both sides of the interrogation position. In addition the nucleic acid can contain heterologous sequences, e.g., adaptor or priming sequences, typically attached to one or both termini of the nucleic acid. The nucleic acid also includes a label or other moiety, e.g., a moiety that allows separation or localization.

In certain embodiments, the purified or isolated preparation of a nucleic acid, e.g., derived from a melanoma sample, comprises one or more of:

(i) a somatic alteration in a predetermined set of genes set forth in Table 1;

(ii) a somatic alteration in an NF1 gene;

(iii) a somatic alteration in an LRP1B gene; or (iv) a C to T transition.

In some embodiments, the preparation is used to determine the mutation load of the sample, e.g., the melanoma sample. In some embodiments, the preparation is disposed in a sequencing device, or a sample holder for use in such a device.

In embodiments, the nucleic acid is between 20 and 1,000, 30 and 900, 40 and 800, 50 and 700, 60 and 600, 70 and 500, 80 and 400, 90 and 300, or 100 and 200 nucleotides in length (with or without heterologous sequences). In one embodiment, the nucleic acid is between 40 and 1,000, 50 and 900, 60 and 800, 70 and 700, 80 and 600, 90 and 500, 100 and 400, 110 and 300, or 120 and 200 nucleotides in length (with or without heterologous sequences). In another embodiment, the nucleic acid is between 50 and 1,000, 50 and 900, 50 and 800, 50 and 700, 50 and 600, 50 and 500, 50 and 400, 50 and 300, or 50 and 200 nucleotides in length (with or without heterologous sequences). In embodiments, the nucleic acid is of sufficient length to allow sequencing (e.g., by chemical sequencing or by determining a difference in $T_m$ between mutant and reference preparations) but is optionally less than 100, 200, 300, 400, or 500 nucleotides in length (with or without heterologous sequences). Such preparations can be used to sequence nucleic acid from a sample, e.g., a neoplastic or tumor sample. In one embodiment the purified preparation is provided by in situ amplification of a nucleic acid provided on a substrate. In embodiments the purified preparation is spatially distinct from other nucleic acids, e.g., other amplified nucleic acids, on a substrate.

In one embodiment, the purified or isolated preparation of nucleic acid is derived from a melanoma, e.g., an advanced melanoma. Such preparations can be used to determine the mutation load in the melanoma, and/or the presence or absence of an altered sequence, e.g., an alteration described herein, in the melanoma.

In another aspect, the invention features, a method of determining the sequence of an interrogation position for an alteration described herein, comprising:

(a) providing a purified or isolated preparation of nucleic acid, e.g., DNA, e.g., genomic DNA or cDNA, or RNA, containing an interrogation position described herein; and (b) sequencing, by a method that breaks or forms a chemical bond, e.g., a covalent or non-covalent chemical bond, e.g., in a detection reagent or a target sequence, the nucleic acid so as to determine the identity of the nucleotide at an interrogation position. The method allows determining if an alteration described herein is present.

In one embodiment, sequencing comprises contacting the nucleic acid comprising an alteration described herein with a detection reagent described herein.

In one embodiment, sequencing comprises determining a physical property, e.g., stability of a duplex form of the nucleic acid comprising an alteration described herein, e.g., $T_m$, that can distinguish mutant from reference sequence.

Reaction Mixtures and Devices

In one aspect, the invention features, reaction mixtures containing a detection reagent and a nucleic acid, e.g., DNA, e.g., genomic DNA or cDNA, or RNA, containing an interrogation position described herein, useful for determining the mutation load of a sample or the presence or absence of an alteration disclosed. In one embodiment, the nucleic acid is acquired or derived from a melanoma, e.g., an advanced melanoma.

In another aspect, the invention features, reaction mixtures containing a detection reagent and a nucleic acid, e.g., DNA, e.g., genomic DNA or cDNA, or RNA, containing an interrogation position described herein, useful for determining the mutation load of a sample or the presence or absence of an alteration disclosed, disposed in a device for determining a physical or chemical property, e.g., stability of a duplex, e.g., $T_m$ or a sample holder for use in such a device. In one embodiment, the device is a calorimeter. In one embodiment the nucleic acid comprising an alteration described herein is acquired or derived from a melanoma, e.g., an advanced melanoma.

In certain embodiments, the reaction mixture described herein comprises:

(a) one or more detection reagents, capable of detecting one or more of:
   (i) a somatic alteration in a predetermined set of genes set forth in Table 1,
   (ii) a somatic alteration in an NF1 gene,
   (iii) a somatic alteration in an LRP1B gene,
   (iv) a C to T transition; and (b) a nucleic acid derived from a melanoma sample comprising one or more of:
   (i) a somatic alteration in a predetermined set of genes set forth in Table 1,
   (ii) a somatic alteration in an NF1 gene,
   (iii) a somatic alteration in an LRP1B gene,
   (iv) a C to T transition.

The detection reagents described herein can be used to determine the mutation load of a sample or the presence or absence of an alteration disclosed in a sample. In embodiments, the sample comprises a nucleic acid that is derived from a melanoma, e.g., an advanced melanoma. The cell can be from a neoplastic or a tumor sample, e.g., a biopsy taken from the neoplasm or the tumor; from circulating tumor cells, e.g., from peripheral blood; or from a blood or plasma sample. In one embodiment, the nucleic acid is derived from e.g., a melanoma, e.g., an advanced melanoma.

Accordingly, in one aspect, the invention features a method of making a reaction mixture comprising combining a detection reagent, capable detecting an alteration described herein, with a nucleic acid derived from a sample comprising a sequence having an interrogation position for an alteration described herein. In certain embodiments, the method comprises combining one or more detection reagents, capable of detecting one or more of: (i) a somatic alteration in a predetermined set of genes set forth in Table 1, (ii) a somatic alteration in an NF1 gene, (iii) a somatic alteration in an LRP1B gene, or (iv) a C to T transition; with a nucleic acid derived from a tumor cell or sample, e.g., a melanoma cell or sample, comprising one or more of: (i) a somatic alteration in a predetermined set of genes set forth in Table 1, (ii) a somatic alteration in an NF1 gene, (iii) a somatic alteration in an LRP1B gene, or (iv) C to T transition.

In one embodiment of the reaction mixture, or the method of making the reaction mixture: the detection reagent comprises a nucleic acid, e.g., a DNA, RNA or mixed DNA/RNA, molecule which is complementary with a nucleic acid sequence on a target nucleic acid (the detection reagent binding site) wherein the detection reagent binding site is disposed in relationship to the interrogation position such that binding of the detection reagent to the detection reagent binding site allows differentiation of mutant and reference sequences for a mutation sequence or event described herein.

In one embodiment of the reaction mixture, or the method of making the reaction mixture: the target nucleic acid sequence is derived from a melanoma, e.g., an advanced melanoma, as described herein. In one embodiment of the reaction mixture, or the method of making the reaction mixture: the mutation is an alteration described herein, including: a substitution, e.g., a base substitution described herein.

An alteration described herein, can be distinguished from a reference, e.g., a non-mutant or wildtype sequence, by reaction with an enzyme that reacts differentially with the mutation and the reference. E.g., they can be distinguished by cleavage with a restriction enzyme that has differing activity for the mutant and reference sequences. E.g., the invention includes a method of contacting a nucleic acid comprising an alteration described herein with such an enzyme and determining if a product of that cleavage which can distinguish mutant from reference sequence is present.

In one aspect the inventions provides, a purified preparation of a restriction enzyme cleavage product which can distinguish between mutant and reference sequence, wherein one end of the cleavage product is defined by an enzyme that cleaves differentially between mutant and reference sequence. In one embodiment, the cleavage product includes the interrogation position.

Detection of Mutated Polypeptide

The activity or level of a mutated polypeptide (e.g., a polypeptide encoded by a gene set forth in Table 1, e.g., a mutated NF1 polypeptide or LRP1B polypeptide) can also be detected and/or quantified by detecting or quantifying the expressed polypeptide. The mutated polypeptide can be detected and quantified by any of a number of means known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry (IHC), and the like. A skilled artisan can adapt known protein/antibody detection methods.

Another agent for detecting a mutated polypeptide is an antibody molecule capable of binding to a polypeptide corresponding to a polypeptide, e.g., an antibody with a detectable label. Techniques for generating antibodies are described herein. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In another embodiment, the antibody is labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair (e.g., biotin-streptavidin), or an antibody fragment (e.g., a single-chain antibody, an isolated antibody hypervariable domain, etc.) which binds specifically with a mutated protein, is used.

Mutated polypeptides from cells can be isolated using techniques that are known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

In another embodiment, Western blot (immunoblot) analysis is used to detect and quantify the presence of a polypeptide in the sample.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an antibody as opposed to the use of other physical or chemical properties to isolate, target, and quantify the analyte.

The mutated polypeptide is detected and/or quantified using any of a number of immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; and Stites & Terr (1991) *Basic and Clinical Immunology* 7th Edition.

Screening Methods

In another aspect, the invention features a method, or assay, for screening for agents that can be used to treat a tumor having a predetermined level of mutation load and/or having an alteration described herein.

The method includes contacting a cell or tissue, e.g., a tumor cell or tissue, having a predetermined level of mutation load and/or having an alteration described herein, with a candidate agent; and detecting a change in a parameter associated with the cell or tissue, e.g., the tumor cell or tissue, e.g., a change in tumor growth, angiogenesis, apoptosis, or metastasis. The method can, optionally, include comparing a value for the parameter to a reference value, e.g., comparing a value for a parameter obtained from a tumor sample with the candidate agent to a value for a parameter obtained from a tumor sample without the candidate agent. In one embodiment, if a decrease in a parameter associated with the tumor, e.g., a change in tumor growth, angiogenesis, apoptosis, or metastasis is detected, the candidate agent is identified.

Exemplary parameters evaluated include one or more of: (i) a change in an activity of a cell, e.g., a tumor cell, e.g., a change in proliferation, morphology or tumorigenicity of the cell; (ii) a change in a tumor present in an animal subject, e.g., size, appearance, proliferation, of the tumor; or (iii) a change in the level, e.g., expression level, of a nucleic acid or polypeptide or protein associated with an activity of a cell, e.g., a tumor cell.

In one embodiment, the contacting step is effected in a cell in culture, e.g., a cell having a predetermined level of mutation load and/or having an alteration described herein. In another embodiment, the contacting step is effected in a cell in vivo (a tumor cell present in a subject), e.g., an animal subject (e.g., an in vivo animal model).

In other embodiments, a change in an activity of a cell is detected in a cell in culture, e.g., a cell having a predetermined level of mutation load and/or having an alteration described herein (e.g., a mammalian cell, a tumor cell or cell line, a recombinant cell). In one embodiment, the cell is a cell isolated from a tumor having a predetermined level of mutation load. In one embodiment, the cell is a recombinant cell that is modified to express a nucleic acid comprising an alteration described herein, e.g., is a recombinant cell transfected with a nucleic acid comprising an alteration described herein. The transfected cell can show a change in response to the expressed mutation, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of the effectiveness of the agent in treating a tumor having a predetermined level of mutation load and/or having an alteration described herein.

In yet other embodiment, a change in a tumor present in an animal subject (e.g., an in vivo animal model) is detected. In one embodiment, the animal model is a tumor containing animal or a xenograft comprising cells having a predetermined level of mutation load and/or having an alteration described herein (e.g., tumorigenic cells having a predetermined level of mutation load and/or having an alteration described herein). The candidate agent can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is effective in treating a tumor having a predetermined level of mutation load and/or having an alteration described herein.

In certain embodiments, the screening methods described herein can be repeated and/or combined. In one embodiment, a candidate agent that is evaluated in a cell-based assay described herein can be further tested in an animal subject.

In one embodiment, the candidate agent is a modulator, e.g., an inhibitor, of an immune checkpoint molecule, e.g., an inhibitor of PD-1 or PD-L1. In one embodiment, the candidate agent is a small molecule compound, a nucleic acid (e.g., antisense, siRNA, aptamer, ribozyme, microRNA), or an antibody molecule (e.g., a full antibody or antigen binding fragment thereof that binds to the protein encoded by the mutated DNA, e.g., a chimeric, humanized, or human antibody molecule). The candidate agent can be obtained from a library (e.g., a commercial library of inhibitors) or rationally designed.

The candidate agents can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Phage display and combinatorial methods for generating antibodies are known in the art (as described in, e.g., U.S. Pat. No. 5,223,409, International Application Publication Nos. WO 92/18619, WO 91/17271, WO 92/20791, WO 92/15679, WO 93/01288, WO 92/01047, WO 92/09690, WO 90/02809; Huse et al. (1989) *Science* 246:1275-1281; Fuchs et al. (1991) *Bio/Technology* 9:1370-1372; Clackson et al. (1991) *Nature* 352:624-628; Garrad et al. (1991) *Bio/Technology* 9:1373-1377; Hoogenboom et al. (1991) *Nuc Acid Res* 19:4133-4137; Barbas et al. (1991) *PNAS* 88:7978-7982; Hawkins et al. (1992) *J Mol Biol* 226:889-896; Hay et al. (1992) *Hum Antibod Hybridomas* 3:81-85; Gram et al. (1992) *PNAS* 89:3576-3580; and Griffths et al. (1993) *EMBO J* 12:725-734.

Chimeric antibodies can be produced by recombinant DNA techniques known in the art (see International Application Publication Nos. WO 86/01533, WO 87/02671, Cabilly et al. U.S. Pat. No. 4,816,567; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060. Also within the scope of the invention are humanized antibodies in which specific amino acids have been substituted, deleted or added. Criteria for selecting amino acids from the donor are described in U.S. Pat. No. 5,585,089. Other techniques for humanizing antibodies are described in U.S. Pat. Nos. 5,693,761, 5,693,762; European Patent No. EP 519596; Morrison, S. L., 1985, *Science* 229:1202-1207, and Oi et al., 1986, *BioTechniques* 4:214.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., International Application Publication Nos. WO 91/00906, WO 91/10741, WO 92/03918, WO 92/03917; Bruggeman et al. 1991 *Eur J Immunol* 21:1323-1326; Bruggeman et al. 1993 *Year Immunol* 7:33-40; Tuaillon et al. 1993 *PNAS* 90:3720-3724; Lonberg, N. et al. 1994 *Nature* 368:856-859; Green, L. L. et al. 1994 *Nature Genet.* 7:13-21; and Morrison, S. L. et al. 1994 *Proc. Natl. Acad. Sci. USA* 81:6851-6855).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; and Felici (1991) *J. Mol. Biol.* 222:301-310; Ladner supra.).

Other embodiments of the invention include the following.

The invention also features an isolated nucleic acid molecule, or an isolated preparation of nucleic acid molecules, that includes an alteration described herein. Such nucleic acid molecules or preparations thereof can include an alteration described herein or can be used to detect, e.g., sequence, an alteration.

The invention also features a nucleic acid molecule, e.g., nucleic acid fragment, suitable as probe, primer, bait or library member that includes, flanks, hybridizes to, which is useful for identifying, or is otherwise based on, an alteration described herein. In certain embodiments, the probe, primer or bait molecule is an oligonucleotide that allows capture, detection or isolation of a nucleic acid molecule containing an alteration described herein, e.g., an alteration in a gene set forth in Table 1, e.g., an NF1 gene or an LRP1B gene.

The oligonucleotide can comprise a nucleotide sequence substantially complementary to nucleic acid molecules or fragments of nucleic acid molecules comprising an alteration described herein. The sequence identity between the nucleic acid molecule, e.g., the oligonucleotide, and the target sequence need not be exact, so long as the sequences are sufficiently complementary to allow the capture, detection or isolation of the target sequence. In one embodiment, the nucleic acid fragment is a probe or primer that includes an oligonucleotide between about 5 and 25, e.g., between 10 and 20, or 10 and 15 nucleotides in length. In other embodiments, the nucleic acid fragment is a bait that includes an oligonucleotide between about 100 to 300 nucleotides, 130 and 230 nucleotides, or 150 and 200 nucleotides, in length.

In one embodiment, the nucleic acid fragment can be used to identify or capture, e.g., by hybridization, a nucleic acid molecule comprising an alteration described herein, e.g., an alteration in a gene set forth in Table 1, e.g., an NF1 gene or an LRP1B gene. For example, the nucleic acid fragment can be a probe, a primer, or a bait, for use in identifying or capturing, e.g., by hybridization, an alteration described herein.

The probes or primers described herein can be used, for example, in PCR amplification. In one exemplary embodiment where detection is based on PCR, amplification of the mutation can be performed using a primer or a primer pair, e.g., for amplifying a sequence flanking an alteration described herein.

In other embodiments, the nucleic acid fragment includes a bait that comprises a nucleotide sequence that hybridizes to a nucleic acid molecules comprising an alteration described herein, and thereby allows the capture or isolation of said nucleic acid molecule. In one embodiment, a bait is suitable for solution phase hybridization. In other embodiments, a bait includes a binding entity, e.g., an affinity tag, that allows capture and separation, e.g., by binding to a binding entity, of a hybrid formed by a bait and a nucleic acid hybridized to the bait.

In other embodiments, the nucleic acid fragment includes a library member comprising a nucleic acid molecule described herein. In one embodiment, the library member includes a mutation, e.g., a base substitution that results in an alteration described herein.

The nucleic acid fragment can be detectably labeled with, e.g., a radiolabel, a fluorescent label, a bioluminescent label, a chemiluminescent label, an enzyme label, a binding pair label, or can include an affinity tag; a tag, or identifier (e.g., an adaptor, barcode or other sequence identifier).

In another aspect, the invention features a polypeptide comprising an alteration described herein (e.g., a purified polypeptide comprising an alteration described herein), a biologically active or antigenic fragment thereof, as well as reagents (e.g., antibody molecules that bind to a polypeptide comprising an alteration described herein), methods for modulating the activity of a polypeptide comprising an alteration described herein and detection of a polypeptide comprising an alteration described herein.

In another embodiment, the polypeptide or fragment is a peptide, e.g., an immunogenic peptide or protein that contains an alteration described herein. Such immunogenic peptides or proteins can be used to raise antibodies specific to the polypeptide or protein comprising an alteration described herein. In other embodiments, such immunogenic peptides or proteins can be used for vaccine preparation. The vaccine preparation can include other components, e.g., an adjuvant.

In another aspect, the invention features antibody molecules that bind to a polypeptide comprising an alteration described herein or fragment described herein. In embodiments the antibody can distinguish wild type from the mutated polypeptide, e.g., the polypeptide comprising an alteration described herein. Techniques for generating antibody molecules are known in the art, and are described, for example, in WO 2012/092426, entitled "Optimization of Multigene Analysis of Tumor Samples, incorporated herein by reference.

The present invention may be defined, e.g., in any of the following numbered paragraphs:

1. A method of treating a subject having a melanoma, the method comprising:

(a) acquiring a value of responder status to a therapy comprising an inhibitor of PD-1 or PD-L1 for the subject, wherein said value of responder status comprises a measure of the tumor mutational burden (TMB) in a melanoma sample, or a sample derived from the melanoma, from the subject; and (b) responsive to an increased value of responder status, e.g., compared to a reference value of responder status, administering to the subject the therapy, thereby treating the subject.

2. A method of treating a subject having a melanoma, the method comprising:

administering a therapy comprising an inhibitor of PD-1 or PD-L1 to the subject, wherein the subject has, or has been identified as having, an increased value of responder status, e.g., compared to a reference value of responder status, and wherein said value of responder status comprises a measure of the tumor mutational burden in a melanoma sample, or a sample derived from the melanoma, from the subject, thereby treating the subject.

3. A method of selecting a therapy comprising an inhibitor of PD-1 or PD-L1 for a subject having a melanoma, the method comprising:

acquiring a value of responder status to the therapy for the subject, wherein said value of responder status comprises a measure of the tumor mutational burden in a melanoma sample, or a sample derived from the melanoma, from the subject, and wherein an increased value of responder status, e.g., compared to a reference value of responder status, indicates that said subject is, or is likely to be, a responder, or said subject will respond, or will likely respond, to the therapy, thereby selecting the therapy.

4. A method of evaluating a subject having a melanoma, the method comprising:

(a) acquiring a value of responder status to a therapy comprising an inhibitor of PD-1 or PD-L1 for the subject, wherein said value of responder status comprises a measure of the tumor mutational burden in a melanoma sample, or a sample derived from the melanoma, from the subject, and (b) identifying the subject as a responder (e.g., a complete responder or partial responder) or non-responder to the therapy, wherein a value of responder status equal to or greater than a reference value of responder status indicates that said subject is, or is likely to be, a responder, or will respond, or will likely respond, to the therapy; or wherein a value of responder status less than a reference value of responder status indicates that said subject is, or is likely to be, a non-responder, or said subject will not respond, or will likely not respond, to the therapy, thereby evaluating the subject.

5. The method of any of claims 1-4, wherein the measure of the tumor mutational burden comprises a determination of one, two, three or all of the following in the sample from the subject:

(i) the level of a somatic alteration (e.g., one or more somatic alterations) in a predetermined set of genes set forth in Table 1;

(ii) the presence of a somatic alteration (e.g., one or more somatic alterations) in an NF1 gene;

(iii) the number of a somatic alteration (e.g., one or more somatic alterations) in an LRP1B gene; or (iv) the number of a C to T transition (e.g., one or more C to T transitions) in a predetermined set of genes set forth in Table 1.

6. The method of any of claims 1-5, wherein the therapy is administered to, or selected for, the subject, responsive to one, two, three or all of the following in the sample from the subject:

(i) an increased level of a somatic alteration (e.g., one or more somatic alterations) in a predetermined set of genes set forth in Table 1, compared to a reference level of a somatic alteration (e.g., one or more somatic alterations) in the predetermined set of genes set forth in Table 1;

(ii) the presence of a somatic alteration (e.g., one or more somatic alterations) in an NF1 gene;

(iii) an increased number of a somatic alteration (e.g., one or more somatic alterations) in an LRP1B gene, compared to a reference level of a somatic alteration (e.g., one or more somatic alterations) in the LRP1B gene; or (iv) an increased number of a C to T transition (e.g., one or more C to T transitions) in an predetermined set of genes set forth in Table 1, compared to a reference level of a C to T transition (e.g., one or more C to T transitions) in the predetermined set of genes set forth in Table 1.

7. A method of treating a subject having a melanoma, the method comprising:

(a) determining one or more of the following in a melanoma sample, or a sample derived from the melanoma, from the subject:

(i) the level of a somatic alteration (e.g., one or more somatic alterations) in a predetermined set of genes set forth in Table 1;

(ii) the presence or absence of a somatic alteration (e.g., one or more somatic alterations) in an NF1 gene;

(iii) the number of a somatic alteration (e.g., one or more somatic alterations) in an LRP1B gene; or (iv) the number of a C to T transition in a predetermined set of genes set forth in Table 1;

(b) responsive to one or more of the following:

(i) an increased level of a somatic alteration (e.g., one or more somatic alterations) in a predetermined set of genes set forth in Table 1, e.g., compared to a reference level of a somatic alteration (e.g., one or more somatic alterations) in the predetermined set of genes set forth in Table 1;

(ii) the presence of a somatic alteration (e.g., one or more somatic alterations) in the NF1 gene;

(iii) an increased number of a somatic alteration (e.g., one or more somatic alterations) in the LRP1B gene, e.g., compared to a reference number of a somatic alterations (e.g., one or more somatic alterations) in the LRP1B gene; or (iv) an increased number of a C to T transition in a predetermined set of genes set forth in Table 1, e.g., compared to a reference number of a C to T transition in the predetermined set of genes set forth in Table 1, administering a therapy comprising an inhibitor of PD-1 or PD-L1 to the subject, thereby treating the subject.

8. The method of any of claims 1-7, wherein the reference value of responder status is a value of responder status for a non-responder to the therapy.

9. The method of any of claims 1-8, wherein the therapy is administered to, or selected for, the subject, responsive to an increased level of tumor mutational burden in the sample from the subject, compared to a reference level of tumor mutational burden.

10. The method of claim 9, wherein the reference level of tumor mutational burden is the level of tumor mutational burden in a melanoma sample, or a sample derived from a melanoma, from a non-responder to the therapy.

11. The method of any of claims 1-10, wherein the subject is identified as a responder to the therapy, when the sample from the subject has one, two, three or all of the following:

(i) an increased level of a somatic alteration in a predetermined set of genes set forth in Table 1, compared to a reference level of a somatic alteration in the predetermined set of genes set forth in Table 1;

(ii) the presence of a somatic alteration in an NF1 gene;

(iii) an increased number of a somatic alteration in an LRP1B gene, compared to a reference level of a somatic alteration in the LRP1B gene; or (iv) an increased number of a C to T transition in a predetermined set of genes set forth in Table 1, compared to a reference level of a C to T transition in the predetermined set of genes set forth in Table 1.

12. The method of any of claims 1-11, wherein the subject is identified as a non-responder to the therapy, when the sample from the subject has one, two, three or all of the following:

(i) a decreased or unchanged level of a somatic alteration in a predetermined set of genes set forth in Table 1, compared to a reference level of a somatic alteration in the predetermined set of genes set forth in Table 1;

(ii) the absence of a somatic alteration in an NF1 gene;

(iii) a similar, same or decreased number of a somatic alteration in an LRP1B gene, compared to a reference level of somatic alterations in the LRP1B gene; or (iv) a similar, same or decreased number of a C to T transition in a predetermined set of genes set forth in Table 1, compared to a reference level of a C to T transition in the predetermined set of genes set forth in Table 1.

13. The method of any of claims 1-12, wherein the predetermined set of genes comprise at least about 50 or more, about 100 or more, about 150 or more, about 200 or more, about 250 or more, about 300 or more, or all of the genes set forth in Table 1.

14. The method of any of claims 9-13, wherein the reference level of a somatic alteration in the predetermined set of genes set forth in Table 1 is the level of a somatic alteration in the predetermined set of genes set forth in Table 1 in a melanoma sample, or a sample derived from a melanoma, from a non-responder to the therapy.

15. The method of any of claims 6-14, wherein the reference level of a somatic alteration in the LRP1B gene is the level of a somatic alteration in the LRP1B gene in a melanoma sample, or a sample derived from a melanoma, from a non-responder to the therapy.

16. The method of any of claims 6-15, wherein the reference level of a C to T transition in a predetermined set of genes set forth in Table 1 is the level of a C to T transition in a melanoma sample, or a sample derived from a melanoma, from a non-responder to the therapy.

17. The method of any of claims 5-16, wherein the level of a somatic alteration in the predetermined set of genes set forth in Table 1 is determined by a method comprising sequencing the predetermined set of genes set forth in Table 1, e.g., sequencing the coding regions of the predetermined set of genes set forth in Table 1.

18. The method of any of claims 5-17, wherein the presence or absence of a somatic alteration in the NF1 gene is determined by a method comprising sequencing the NF1 gene, e.g., the coding region of the NF1 gene.

19. The method of any of claims 5-18, wherein the number of somatic alterations in the LRP1B gene is determined by a method comprising sequencing the LRP1B gene, e.g., the coding region of the LRP1B gene.

20. The method of any of claims 5-19, wherein the number of a C to T transition in a predetermined set of genes set forth in Table 1 is determined by a method comprising sequencing the predetermined set of genes set forth in Table 1.

21. The method of any of claims 1-20, further comprising, responsive to measure of the tumor mutational burden, performing one, two, three or all of the following:
(a) administering an altered dose of the therapy to the subject;
(b) altering a schedule or time course of the therapy for the subject;
(c) administering, e.g., to a non-responder or a partial responder, an additional agent in combination with the therapy; or
(d) prognosticating a time course in the progression of the melanoma in the subject.

22. The method of any of claims 5-21, wherein the determination of the level of a somatic alteration in the predetermined set of genes set forth in Table 1 comprises a determination of the level of a somatic alteration in about 25 or more, e.g., about 50 or more, about 100 or more, about 150 or more, about 200 or more, about 250 or more, about 300 or more, or all genes set forth in Table 1.

23. The method of any of claims 5-22, wherein the determination of the level of a somatic alteration in the predetermined set of genes set forth in Table 1 comprises a determination of the number of a somatic alteration per a preselected unit, e.g., per megabase in the coding regions of the predetermined set of genes, e.g., in the coding regions of the predetermined set of genes sequenced.

24. The method of any of claims 1-23, wherein the therapy is administered to, or selected for, the subject, responsive an increased level of a somatic alteration in the predetermined set of genes set forth in Table 1, e.g., at least about 2-fold, at least about 3-fold, at least about 5-fold, at least about 10-fold, at least about 15-fold, at least about 20-fold, at least about 30-fold, at least about 40-fold, or at least about 50-fold increase, compared to the reference level of a somatic alteration in the predetermined set of genes set forth in Table 1.

25. The method of any of claims 1-24, wherein the therapy is administered to, or selected for, the subject, responsive to a determination that the number of somatic alterations in the predetermined set of genes set forth in Table 1 is about 3.3 or more, e.g., about 5 or more, about 10 or more, about 15 or more, about 20 or more, about 25 or more, about 30 or more, about 35 or more, about 40 or more, about 45 or more, or about 50 or more, somatic alterations per megabase in the coding regions of the predetermined set of genes.

26. The method of any of claims 1-25, wherein the therapy is administered to, or selected for, the subject, responsive to a determination that the number of somatic alterations in the predetermined set of genes set forth in Table 1 is about 23.1 more, e.g., about 25 or more, about 30 or more, about 35 or more, about 40 or more, about 45 or more, or about 50 or more, somatic alterations per megabase in the coding regions of the predetermined set of genes.

27. The method of any of claims 1-26, wherein the therapy is administered to, or selected for, the subject, responsive to a determination that the number of somatic alterations in the predetermined set of genes set forth in Table 1 is between about 3.3 and about 23.1, e.g., between about 5 and about 20, between about 10 and about 20, or between about 15 and about 20, somatic alterations per megabase in the coding regions of the predetermined set of genes.

28. The method of any of claims 1-27, wherein an increased level of somatic alterations in the predetermined set of genes set forth in Table 1, e.g., at least about 2-fold, at least about 3-fold, at least about 5-fold, at least about 10-fold, at least about 15-fold, at least about 20-fold, at least about 30-fold, at least about 40-fold, or at least about 50-fold increase, compared to the reference level of somatic alterations in the predetermined set of genes set forth in Table 1, indicates that the subject is a responder to the therapy.

29. The method of any of claims 1-28, wherein a similar, same or decreased level of a somatic alteration in the predetermined set of genes set forth in Table 1, compared to the reference level of a somatic alteration in the predetermined set of genes set forth in Table 1, indicates that the subject is a non-responder to the therapy.

30. The method of any of claims 1-29, wherein a determination that the number of somatic alterations in the predetermined set of genes set forth in Table 1 is about 3.3 or more, e.g., about 5 or more, about 10 or more, about 15 or more, about 20 or more, about 25 or more, about 30 or more, about 35 or more, about 40 or more, about 45 or more, or about 50 or more, somatic alterations per megabase in the coding regions of the predetermined set of genes, indicates that the subject is a responder, e.g., a complete responder or partial responder, to the therapy.

31. The method of any of claims 1-30, wherein a determination that the number of somatic alterations in the predetermined set of genes set forth in Table 1 is less than about 3.3 somatic alterations per megabase in the coding regions of the predetermined set of genes, indicates that the subject is a non-responder to the therapy.

32. The method of any of claims 1-31, wherein a determination that the number of somatic alterations in the predetermined set of genes set forth in Table 1 is about 23.1 or more, e.g., about 25 or more, about 30 or more, about 35 or more, about 40 or more, about 45 or more, or about 50 or more, somatic alterations per megabase in the coding regions of the predetermined set of genes, indicates that the subject is a responder, e.g., a complete responder, to the therapy.

33. The method of any of claims 1-32, wherein a determination that the number of a somatic alteration in the predetermined set of genes set forth in Table 1 is less than about 23.1 somatic alterations per megabase in the coding regions of the predetermined set of genes set forth in Table 1, indicates that the subject is a partial responder or non-responder to the therapy.

34. The method of any of claims 1-33, wherein a determination that the number of somatic alterations in the predetermined set of genes set forth in Table 1 is between about 3.2 (e.g., about 3.3) and about 20, e.g., between about 5 and about 20, between about 10 and about 20, or between about 15 and about 20, somatic alterations per megabase in the coding regions of the predetermined set of genes set forth in Table 1, indicates that the subject is a partial responder to the therapy.

35. The method of any of claims 1-34, wherein the therapy is administered to, or selected for, the subject, responsive to a determination that a somatic alteration is present in the coding region of the NF1 gene.

36. The method of any of claims 1-35, wherein the presence of a somatic alteration in the coding region of the NF1 gene indicates that the subject is, or is likely to be, a responder, or will respond, or will likely respond, to the therapy.

37. The method of any of claims 1-36, wherein the therapy is administered to, or selected for, the subject, responsive to a determination that:
(a) a somatic alteration is present in the coding region of an NF1 gene; and
(b) the level of somatic alterations in a predetermined set of genes set forth in Table 1 is about 35 or more, about 38.5 or more, about 40 or more, about 45 or more, or about 50 or more somatic alterations per megabase in the coding regions of the predetermined set of genes set forth in Table 1.

38. The method of any of claims 1-37, wherein the therapy is administered to, or selected for, the subject, responsive to a determination of:
(a) a presence of a somatic alteration in the coding region of an NF1 gene; and
(b) an increased, e.g., increased at least about 2-fold, at least about 3-fold, at least about 5-fold, or at least about 10-fold, level of a somatic alteration in a predetermined set of genes set forth in Table 1, compared to a level of a somatic alteration in the predetermined set of genes set forth in Table 1 in a melanoma sample or a sample derived from a melanoma that comprises a somatic alteration in an BRAF gene, a somatic alteration in an NRAS gene, or is triple WT (wild type) for BRAF, NRAS and NF1 genes.

39. The method of any of claims 1-38, wherein the therapy is administered to, or selected for, the subject, responsive to a determination of a presence of about 1 or more, about 2 or more, about 3 or more, about 4 or more, or about 5 or more, somatic alterations in an LRP1B gene.

40. The method of any of claims 1-39, wherein the presence of about 1 or more, about 2 or more, about 3 or more, about 4 or more, or about 5 or more, somatic alterations in an LRP1B gene indicates that the subject is, or is likely to be, a responder, or will respond, or will likely respond, to the therapy.

41. The method of any of claims 1-40, wherein the therapy is administered to, or selected for, the subject, responsive to a determination of an increased number of a somatic alteration in LRP1B, e.g., increased by at least about 2-fold, at least about 2.5-fold, at least about 2.8-fold, at least about 3-fold, at least about 3.5-fold, at least about 4-fold, or at least about 5-fold, compared to a reference number of a somatic alteration in the LRP1B gene.

42. The method of claim 41, wherein the reference number of a somatic alteration in the LRP1B gene is the number of a somatic alteration in the LRP1B gene in a melanoma sample or a sample derived from a melanoma from a non-responder to the therapy.

43. The method of claim 41 or 42, wherein the reference number of a somatic alteration in the LRP1B gene is 0 or 1 somatic alteration.

44. The method of any of claims 1-43, wherein the therapy is administered to, or selected for, the subject, responsive to a determination of a presence of about 20 or more, about 25 or more, about 30 or more, about 40 or more, or about 50 or more a C to T transition in a predetermined set of genes set forth in Table 1.

45. The method of any of claims 1-44, wherein a determination of a presence of about 20 or more, about 25 or more, about 30 or more, about 40 or more, or about 50 or more C to T transitions in a predetermined set of genes set forth in Table 1, indicates that the subject is a responder to the therapy comprising the inhibitor of PD-1 or PD-L1.

46. The method of any of claims 1-45, wherein the therapy is administered to, or selected for, the subject, responsive to a determination of an increased number of a C to T transition in a predetermined set of genes set forth in Table 1, e.g., increased by at least about 8-fold, at least about 10-fold, at least about 12-fold, at least about 15-fold, or at least about 20-fold, compared to the reference number of a C to T transition in the predetermined set of genes set forth in Table 1.

47. The method of claim 46, wherein the reference number of a C to T transition is the number of a C to T transition in a melanoma sample or a sample derived from a melanoma from a non-responder to the therapy.

48. The method of claim 46 or 47, wherein the reference number of a C to T transition is about two C to T transitions.

49. The method of any of claims 1-48, wherein the subject is receiving, or has received, a different therapy comprising a therapeutic agent or modality other than an inhibitor of PD-1 or PD-L1.

50. The method of claim 49, wherein the different therapy is discontinued, responsive to the determination of one, two, three or all of the following:
(i) an increased level of a somatic alteration in a predetermined set of genes set forth in Table 1, compared to a reference level of a somatic alteration in the predetermined set of genes set forth in Table 1;
(ii) the presence of a somatic alteration in an NF1 gene;
(iii) an increased number of a somatic alteration in an LRP1B gene, compared to a reference level of a somatic alteration in the LRP1B gene; or
(iv) an increased number of a C to T transition in a predetermined set of genes set forth in Table 1, compared to a reference level of a C to T transition in the predetermined set of genes set forth in Table 1.

51. The method of claim 49 or 50, wherein the therapy is administered after cessation of the different therapy.

52. The method of claim 49 or 50, wherein the therapy is administered in combination with the different therapy.

53. The method of any of claims 49-52, wherein the different therapy is chosen from a chemotherapy, a radiation therapy, an immunotherapy, an immunoradiotherapy, an oncolytic virotherapy, a surgical procedure, or any combination thereof.

54. The method of any of claims 49-53, wherein the different therapy comprises one or more of: dacarbazine, temozolomide, interleukin-2 (IL-2), an interferon, ipilimumab, a BRAF inhibitor, a MEK inhibitor, talimogene laherparepvec, an adoptive cell transfer, or any combination thereof.

55. The method of claim 54, wherein the interferon is a recombinant interferon alfa-2b or a peginterferon alfa-2b.

56. The method of claim 54, wherein the BRAF inhibitor is vemurafenib or dabrafenib.

57. The method of claim 54, wherein the MEK inhibitor is cobimetinib or trametinib.

58. The method of claim 54, wherein the adoptive cell transfer comprises modified T cells or modified dendritic cells.

59. The method of any of claims 1-58, wherein the inhibitor of PD-1 is an anti-PD-1 antibody.

60. The method of claim 59, wherein the inhibitor of PD-1 is chosen from nivolumab (ONO-4538, BMS-936558, or MDX1106), pembrolizumab (MK-3475 or lambrolizumab), pidilizumab (CT-011), MED10680 (AMP-514), PDR001, REGN2810, BGB-108, BGB-A317, SHR-1210 (HR-301210, SHR1210, or SHR-1210), PF-06801591, or AMP-224.

61. The method of any of claims 1-58, wherein the inhibitor of PD-L1 is an anti-PD-L1 antibody.

62. The method of claim 61, wherein inhibitor of PD-L1 is chosen from atezolizumab (MPDL3280A, RG7446, or RO5541267), YW243.55.S70, MDX-1105, durvalumab (MED14736), or avelumab (MSB0010718C).

63. The method of any of claims 1-62, wherein the somatic alterations comprise one or more of the following: a silent mutation (e.g., a synonymous alteration), a somatic alteration that has not been identified as being associated with a cancer phenotype, a passenger mutation (e.g., an alteration that has no detectable effect on the fitness of a clone), a variant of unknown significance (VUS) (e.g., an alteration, the pathogenicity of which can neither be confirmed nor ruled out), a point mutation, a coding short variant (e.g., a base substitution or an indel), a non-synonymous single nucleotide variant (SNV), a splice variant.

64. The method of any of claims 1-63, wherein the alterations (e.g., somatic alterations) do not comprise one or more of the following: a rearrangement (e.g., a translocation), a functional alteration, or a germline mutation, 65. The method of any of claims 1-64, wherein the somatic alteration is a silent mutation, e.g., a synonymous alteration.

66. The method of any of claims 1-64, wherein the somatic alteration has not been identified as being associated with a cancer phenotype.

67. The method of any of claims 1-64, wherein the somatic alteration is a passenger mutation, e.g., an alteration that has no detectable effect on the fitness of a clone.

68. The method of any of claims 1-64, wherein the somatic alteration is a variant of unknown significance (VUS), e.g., an alteration, the pathogenicity of which can neither be confirmed nor ruled out.

69. The method of any of claims 1-64, wherein the somatic alteration is a point mutation.

70. The method of any of claims 1-64, wherein the somatic alteration is other than a rearrangement, e.g., other than a translocation.

71. The method of any of claims 1-64, wherein the somatic alteration is a coding short variant, e.g., a base substitution or an indel.

72. The method of any of claims 1-64, wherein the somatic alteration is a non-synonymous single nucleotide variant (SNV).

73. The method of any of claims 1-64, wherein the somatic alteration is a splice variant.

74. The method of any of claims 1-64, wherein the somatic alteration is not a functional alteration.

75. The method of any of claims 1-64, wherein the alteration is not a germline mutation.

76. A system for evaluating a subject having a melanoma, comprising:
at least one processor operatively connected to a memory, the at least one processor when executing is configured to:
(a) acquire a value of responder status to a therapy comprising an inhibitor of PD-1 or PD-L1 for the subject, wherein said value of responder status comprises a measure of the tumor mutational burden in a melanoma sample, or a sample derived from the melanoma, from the subject, and
(b) identify the subject as a responder (e.g., a complete responder or partial responder) or non-responder to the therapy,
wherein a value of responder status equal to or greater than a reference value of responder status indicates that said subject is, or is likely to be, a responder, or will respond, or will likely respond, to the therapy; or
wherein a value of responder status less than a reference value of responder status indicates that said subject is, or is likely to be, a non-responder, or will not respond, or will not likely respond, to the therapy,
thereby evaluating the subject.

77. The system of claim 76, wherein the measure of the tumor mutational burden comprises a determination of one, two, three or all of the following in the sample from the subject:
(i) the level of a somatic alteration (e.g., one or more somatic alterations) in a predetermined set of genes set forth in Table 1;
(ii) the presence of a somatic alteration (e.g., one or more somatic alterations) in an NF1 gene;
(iii) the number of a somatic alteration (e.g., one or more somatic alterations) in an LRP1B gene; or
(iv) the number of a C to T transition a predetermined set of genes set forth in Table 1.

78. The system of claim 76 or 77, wherein the therapy is administered to, or selected for, the subject, responsive to one, two, three or all of the following in the sample from the subject:
(i) an increased level of a somatic alteration in a predetermined set of genes set forth in Table 1, compared to a reference level of a somatic alteration in the predetermined set of genes set forth in Table 1;
(ii) the presence of a somatic alteration in the NF1 gene;
(iii) an increased number of somatic alteration in the LRP1B gene, compared to a reference level of a somatic alteration in the LRP1B gene; or
(iv) an increased number of a C to T transition in a predetermined set of genes set forth in Table 1, compared to a reference level of a C to T transition in the predetermined set of genes set forth in Table 1.

79. A kit comprising:
(a) one or more detection reagents, capable of detecting one or more of:
(i) a somatic alteration (e.g., one or more somatic alterations) in a predetermined set of genes set forth in Table 1,
(ii) a somatic alteration (e.g., one or more somatic alterations) in an NF1 gene,
(iii) a somatic alteration (e.g., one or more somatic alterations) in an LRP1B gene, (iv) a C to T transition (e.g., one or more C to T transitions) in a predetermined set of genes set forth in Table 1;

(b) instructions for use in determining the tumor mutational burden in a melanoma sample, or a sample derived from a melanoma, and/or in treating a melanoma in a subject; and (optionally) (c) an inhibitor of PD-1 or PD-L1 or a composition thereof.

80. A purified or isolated preparation of a nucleic acid derived from a melanoma sample, or a sample derived from a melanoma, the preparation comprising one or more of:

(i) a somatic alteration (e.g., one or more somatic alterations) in a predetermined set of genes set forth in Table 1, (ii) a somatic alteration (e.g., one or more somatic alterations) in an NF1 gene, (iii) a somatic alteration (e.g., one or more somatic alterations) in an LRP1B gene, (iv) a C to T transition (e.g., one or more C to T transitions) in a predetermined set of genes set forth in Table 1;

wherein the preparation is used to determine the tumor mutational burden of the sample, disposed in a sequencing device, or a sample holder for use in such a device.

81. A reaction mixture, comprising:

(a) one or more detection reagents, capable of detecting one or more of:

(i) a somatic alteration (e.g., one or more somatic alterations) in a predetermined set of genes set forth in Table 1, (ii) a somatic alteration (e.g., one or more somatic alterations) in an NF1 gene, (iii) a somatic alteration (e.g., one or more somatic alterations) in an LRP1B gene, (iv) a C to T transition (e.g., one or more C to T transitions) in a predetermined set of genes set forth in Table 1;

(b) a nucleic acid derived from a melanoma sample, or a sample derived from a melanoma, comprising one or more of:

(i) a somatic alteration (e.g., one or more somatic alterations) in a predetermined set of genes set forth in Table 1, (ii) a somatic alteration (e.g., one or more somatic alterations) in an NF1 gene, (iii) a somatic alteration (e.g., one or more somatic alterations) in an LRP1B gene, (iv) a C to T transition (e.g., one or more C to T transitions) in a predetermined set of genes set forth in Table 1;

wherein the reaction mixture is used to determine the tumor mutational burden of the sample, disposed in a sequencing device, or a sample holder for use in such a device.

82. A method of making a reaction mixture, the method comprising:

combining one or more detection reagents, capable of detecting one or more of:

(i) a somatic alteration (e.g., one or more somatic alterations) in a predetermined set of genes set forth in Table 1, (ii) a somatic alteration (e.g., one or more somatic alterations) in an NF1 gene, (iii) a somatic alteration (e.g., one or more somatic alterations) in an LRP1B gene, (iv) a C to T transition (e.g., one or more C to T transitions) in a predetermined set of genes set forth in Table 1;

with a nucleic acid derived from a melanoma sample, or a sample derived from a melanoma, comprising one or more of:

(i) a somatic alteration (e.g., one or more somatic alterations) in a predetermined set of genes set forth in Table 1, (ii) a somatic alteration (e.g., one or more somatic alterations) in an NF1 gene, (iii) a somatic alteration (e.g., one or more somatic alterations) in an LRP1B gene, (iv) a C to T transition (e.g., one or more C to T transitions) in a predetermined set of genes set forth in Table 1;

thereby making the reaction mixture.

EXAMPLES

Example 1: Targeted Next Generation Sequencing Identifies Markers of Response to PD-1 Blockade Summary Therapeutic antibodies blocking programmed death-1 and its ligand (PD-1/PD-L1) induce durable responses in a substantial fraction of melanoma patients. This study sought to determine whether the number and/or type of mutations identified using a hybrid capture-based next generation sequencing (NGS) panel was correlated with response to anti-PD-1 in melanoma.

Using archival melanoma samples from anti-PD-1/PD-L1-treated patients, hybrid capture-based NGS was performed on 236-315 genes and T-cell receptor (TCR) sequencing was performed on initial and validation cohorts from two centers.

Patients who responded to the anti-PD-1 or anti-PD-L1 had higher mutational load in an initial cohort (median 45.6 vs. 3.9 mutations/MB; P=0.003), and a validation cohort (37.1 vs. 12.8 mutations/MB; P=0.002) compared with non-responders. Response rate, progression-free survival (PFS), and overall survival (OS) were superior in the high, compared with intermediate and low, mutation load groups. Melanomas with NF1 mutations harbored high mutational loads (median 62.7 mutations/MB) and high response rates (74%), whereas BRAF/NRAS/NF1 wild type melanomas had a lower mutational load. In these archival samples, TCR clonality did not predict response. Mutation numbers in the 315 genes in the NGS platform strongly correlated with those detected by whole-exome sequencing in The Cancer Genome Atlas samples, but was not associated with survival.

Thus, mutational load, as determined by a hybrid capture-based NGS platform, effectively stratified patients by likelihood of response. This approach can provide a clinically feasible predictor of response to an anti-PD-1 and/or anti-PD-L1 therapy.

Methods

Patients

Protected health information was reviewed according to the Health Insurance Portability and Accountability Act (HIPAA) guidelines. Patients and samples were retrospectively selected under IRB-approved protocols. All patients had metastatic melanoma and began anti-PD-1 (nivolumab or pembrolizumab) or anti-PD-L1 (atezolizumab) treatment as part of a clinical trial or as standard of care. All patients had evaluable responses determined by radiographic imaging or had rapid clinical progression precluding further imaging. Cross-sectional imaging was performed at 8-12 week intervals per study protocols or standard of care. Baseline characteristics, treatment response, progression-free survival (PFS), and overall survival (OS), were obtained through medical record and tumor imaging review. Patients were classified as responders if they experienced classical partial or complete responses by RECIST 1.1 (Eisenhauer E A, et al. *Eur J Cancer* 2009; 45: 228-47; n=30), or atypical immune-related responses lasting at least 12 months (n=2), or as nonresponders if they failed to respond.

Most formalin-fixed paraffin embedded (FFPE) specimens underwent testing for research purposes only (n=40). These samples comprised all patients with remaining available FFPE with evaluable therapeutic responses at the time of analysis. Patients treated with anti-PD-1/PD-L1 that had been obtained testing for clinical purposes (e.g., to identify actionable mutations; n=25) were also included. Most samples were obtained within 12 months prior to starting treatment (n=43). Other specimens were obtained >12 months prior to therapy (n=15) or even shortly after treatment initiation (n=7). All pre-treatment samples with available tissue underwent ImmunoSeq strictly for research purposes.

Next Generation Sequencing (NGS), e.g., Targeted NGS, and the Cancer Genome Atlas (TCGA) Analysis DNA sequencing was performed using an extensively-validated, Clinical Laboratory Improvement Amendments-certified, hybrid capture-based NGS platform (Foundation-One®, Foundation Medicine, Cambridge Mass.) (Frampton G M et al. *Nat Biotechnol* 31:1023-31, 2013). The initial cohort (n=32) was sequenced by a version which evaluated exons from 236 cancer-related genes and introns of 19 genes. A second, independent cohort (n=33) was sequenced by a subsequent version which evaluates exons from 315 genes and introns from 28 genes (hereafter termed "validation cohort"). Methods for DNA extraction and sequencing have been extensively validated and published previously (Frampton et al. *Nat Biotechnol* 31:1023-31, 2013).

To calculate total mutational burden, the number of somatic mutations detected on the test involving the genes set forth in Table 1 was quantified, and that value was extrapolated to the exome as a whole using the following algorithm. All short variant alterations, base substitutions and indels detected on the test were counted. All coding alterations, including silent alterations, were also counted, whereas non-coding alterations were not counted. Alterations with known (occurring as known somatic alterations in the COSMIC database; cancer.sanger.ac.uk/cosmic) and likely (truncations in tumor suppressor genes) functional status were not counted. This correction was performed to avoid upward skewing of mutational load, since the test preferentially profiles genes known to be recurrently mutated in cancer. Predicted germline variants were excluded and filtered using the dbSNP database (www.ncbi.nlm.nih.gov/SNP), the ExAC database (those with ≥2 counts) (exac.broadinstitute.org), and the SGZ (somatic germline zygosity) algorithm (e.g., as described in International Application Publication No. WO2014/183078 and U.S. Application Publication No. 2014/0336996, the contents of which are incorporated by reference in their entirety). The SGZ algorithm was refined using the cohort of >60,000 clinical specimens to further reduce the chance of calling germline variants. To calculate the mutation load per megabase (MB), the total number of mutations counted was divided by the coding region target territory of the test, covering 0.91 and 1.25 megabases for the 236 gene and 315 gene versions, respectively.

Matched somatic mutation and clinical data from 345 skin cutaneous melanoma tumor samples from TCGA (including 263 with clinical data) were retrieved from the CbioPortal (www.cbioportal.org/public-portal) using the Cancer Genome Data Server-R (CGDS-R) API, which provided a set of functions for extracting data from the CGDS. Using TCGA, the number of nonsynonymous mutations in 315 genes sequenced in the test was compared to total mutations identified by all coding genes by whole exome sequencing (WES) (n=20,022). Survival data was also evaluated for these samples.

T Cell Receptor Sequencing

TCR sequencing and clonality quantification, and determination of T-cell fraction, were assessed in pretreatment FFPE tumor samples using survey level ImmunoSeq™, as has been previously described (Adaptive Biotechnologies; Tumeh et al. *Nature* 515:568-71, 2014; Gerlinger et al. *J Pathol*, 2013). T cell clonality was calculated as follows: Shannon entropy was calculated on the clonal abundance of all productive TCR sequences in the data set. Shannon entropy was normalized by dividing Shannon entropy by the logarithm of the number of unique productive TCR sequences. This normalized entropy value was then inverted (1—normalized entropy) to produce the clonality metric.

Statistical Analysis

Mutational load was compared between responders and non-responders using the Mann Whitney U test. The performance of mutational load across a range of values was calculated, and thresholds for the low, intermediate, and high groups were selected from local maxima across a range of clinically meaningful values using ROC curves. ROC was used to identify the optimal mutation cutoffs from the initial cohort to assess in the validation cohort. Response rates between patients with particular genomic changes were compared using $\chi^2$ testing and were not corrected for multiple comparisons. T-cell clonality and T-cell fraction were compared between responders and nonresponders using the Mann-Whitney U test. In the TCGA samples, mutation number identified in 315 tested genes was correlated with all coding genes (n=20,022) using the Spearman test (Cancer Genome Atlas Network. *Cell* 2015; 161: 1681-96). Survival in the TCGA was also correlated with mutational load calculated by WES and tested genes, and compared between mutational load groups using Cox proportional hazards. PFS and OS were assessed by the Kaplan-Meier and patients were censored at last follow-up, if progression-free and/or alive. PFS and OS for high, intermediate, and low mutation were compared between mutation groups using the logrank test. Cox proportional hazards analysis was performed to assess the impact of mutation load, controlled for stage, age, gender, and prior ipilimumab. All analyses were performed using GraphPad Prism version 6.05 and the R statistical computing package version 3.2.1.

Results

Figure 1B:
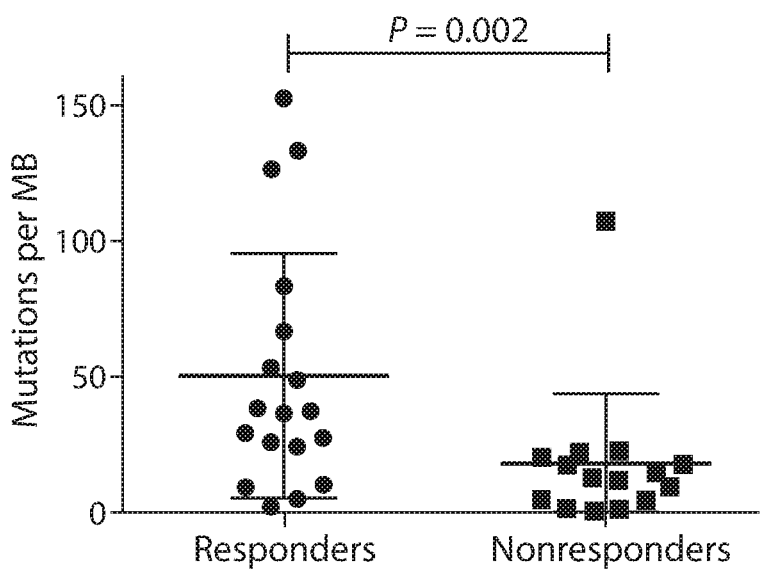
FIG. 1B depicts the mutational load in responders vs. non-responders in validation cohort.

Mutational Burden as Assessed by Hybrid Capture-Based NGS Correlates with Response to an Anti-PD-1 or Anti-PD-L1 Therapy Hybrid capture-based NGS was performed in samples from patients treated with an anti-PD-1 or anti-PD-L1 therapy (Table 3). In an initial cohort, the mutation load in anti-PD-1 or anti-PD-L1 responders was significantly greater than in non-responders (median 45.6 vs. 3.9 mutations/MB; P=0.003, FIG. 1A). A similar difference was observed in the validation cohort (median 37.1 vs. 12.8 mutations/MB, P=0.002; FIG. 1B). Results were similar in "optimal" samples obtained within 12 months of starting treatment compared to other samples (Table 4).

TABLE 3

Clinical characteristics of initial and validation cohort

| Variable | Initial Cohort (n = 32) Number (%) | Validation Cohort (n = 33) Number (%) | P-value |
|---|---|---|---|
| Age (median, range) | 55 (33-80) | 62 (32-85) | 0.65 |
| Sex | | | |
| Male | 21 (66) | 17 (52) | 0.25 |
| Female | 11 (34) | 16 (48) | |
| Metastatic stage | | | |
| IV M1a | 3 (9) | 2 (6) | 0.79 |
| IV M1b | 5 (16) | 4 (12) | |
| IV M1c | 24 (75) | 27 (82) | |
| Primary tumor site | | | |
| Cutaneous | 18 (56) | 26 (79) | 0.13 |
| Non-cutaneous | 10 (31) | 4 (12) | |
| Unknown | 4 (13) | 3 (9) | |
| Treatment | | | |
| Nivolumab | 15 | 4 | <0.001 |
| Pembrolizumab | 14 | 29 | |
| Atezolizumab | 3 | 0 | |
| Prior therapy | | | |
| Lines of prior therapy (median, range) | 1 (0-4) | 1 (0-6) | 0.23 |
| Prior BRAF inhibitor | 3 (9) | 8 (24) | 0.11 |
| Prior ipilimumab | 14 (44) | 23 (70) | 0.03 |
| Prior chemotherapy | 5 (16) | 5 (15) | 0.96 |

TABLE 4

Results for samples obtained ≤12 months prior to therapy ("optimal") vs. those obtained >12 months from treatment or shortly after starting therapy ("non-optimal")

Optimal samples (n = 43)

| | Responders n = 21 | Non-responders n = 22 | p-value |
|---|---|---|---|
| Mutational load (mutations/MB) | 43.5 | 8.1 | <0.001 |

Non-optimal samples (n = 22)

| | Responders n = 11 | Non-responders n = 11 | p-value |
|---|---|---|---|
| Mutational load (mutations/MB) | 37.5 | 5.5 | 0.027 |

Figure 2A:
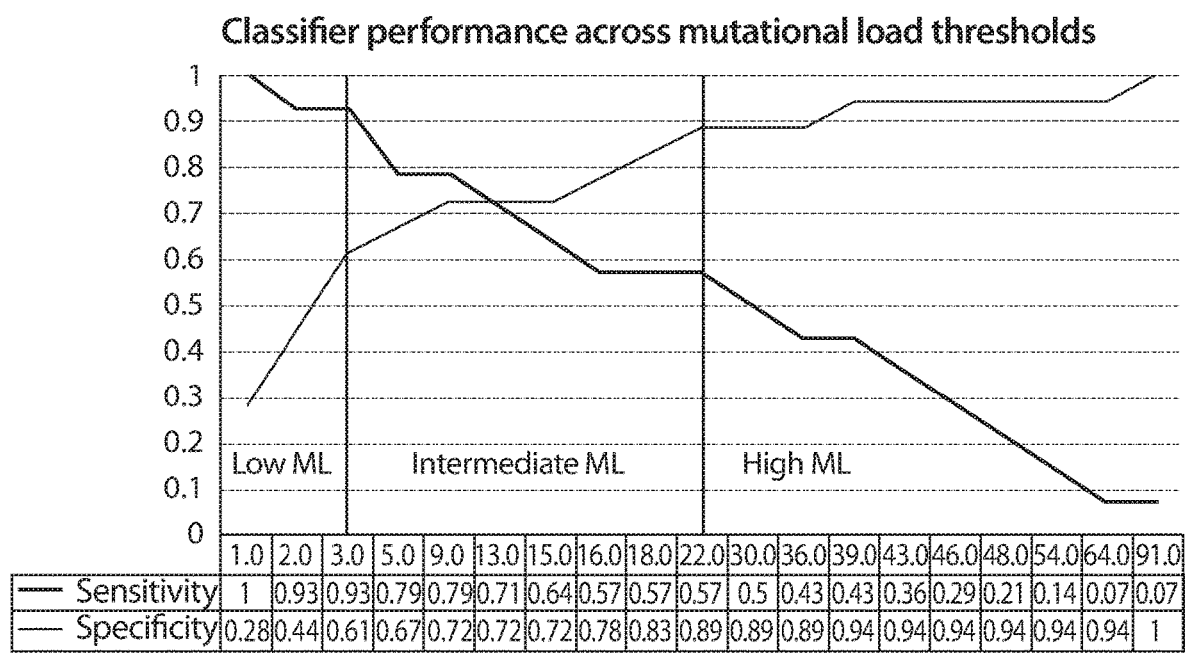
FIG. 2A depicts the performance of mutational load across a range of potential thresholds. Vertical bars indicate the thresholds selected based on local performance maxima and clinical relevance.
Figure 2B:
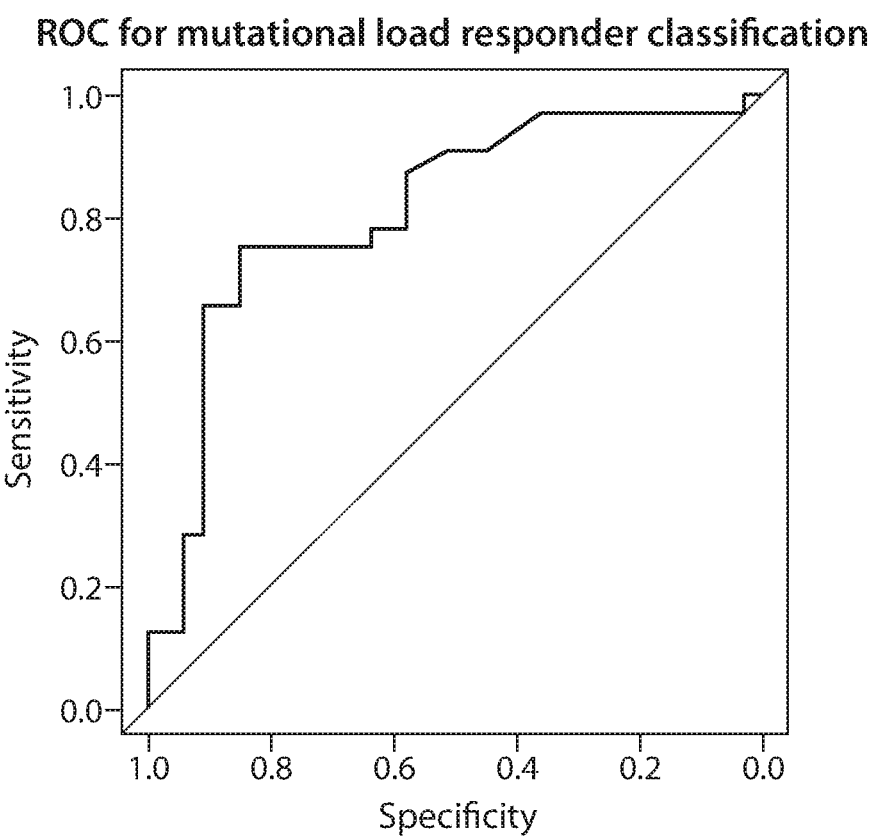
FIG. 2B depicts the Receiver Operating Curve (ROC) for mutational loads cutoffs of 3.3 mutations/MB (low mutational load group) and 23.1 mutations/MB (high mutational load group).

Whether particular cutoffs could be used to classify patients by likelihood of response to therapy was assessed. Using optimized ROC on the initial cohort, it appears that stratifying patients into three groups had superior predictive capacity compared to binary cutoff classification (FIGS. 2A-2B). Patients were divided into high (>23.1 mutations/MB), intermediate (3.3-23.1 mutations/MB), and low (<3.3 mutations/MB) mutation load groups. Using these thresholds, superior objective response rates (ORR) were observed in the high mutational load group, followed by intermediate and low groups (82% vs. 36% vs. 10% response rate; $\chi^2$P=0.003, Table 5). These cutoffs were applied to the validation cohort; superior ORR also occurred in the high mutation load group (88% vs. 29% vs. 25%, $\chi^2$P=0.001). Aggregating the initial and validation cohort, the ORR was greatest in the high (85%) followed by intermediate (29%), and low (14%) mutation load groups (P<0.001).

TABLE 5

Response rate stratified by mutational burden

| | Response | No Response | P-value |
|---|---|---|---|
| Initial cohort (n = 32) | | | |
| High (>23.1 mutations/MB) n = 11 | 9 (82%) | 2 (18%) | 0.003 |
| Intermediate (3.3-23.1 mutations/MB) n = 11 | 4 (36%) | 7 (64%) | |
| Low (<3.3 mutations/MB) n = 10 | 1 (10%) | 9 (90%) | |
| Validation cohort (n = 33) | | | |
| High (>23.1 mutations/MB) n = 16 | 14 (88%) | 2 (12%) | 0.001 |
| Intermediate (3.3-23.1 mutations/MB) n = 13 | 3 (23%) | 10 (77%) | |
| Low (<3.3 mutations/MB) n = 4 | 1 (25%) | 3 (75%) | |
| Entire cohort (n = 65) | | | |
| High (>23.1 mutations/MB) n = 27 | 23 (85%) | 4 (15%) | <0.001 |
| Intermediate (3.3-23.1 mutations/MB) n = 24 | 7 (29%) | 17 (71%) | |
| Low (<3.3 mutations/MB) n = 14 | 2 (14%) | 12 (86%) | |

Figure 1C:
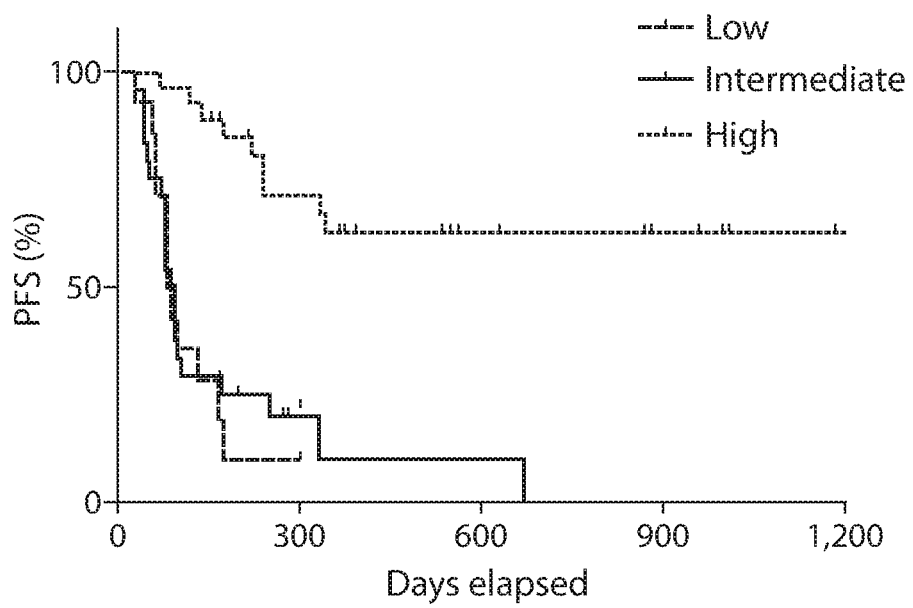
FIG. 1C depicts the progression-free survival in patients with high, intermediate, and low mutational load.
Figure 1D:
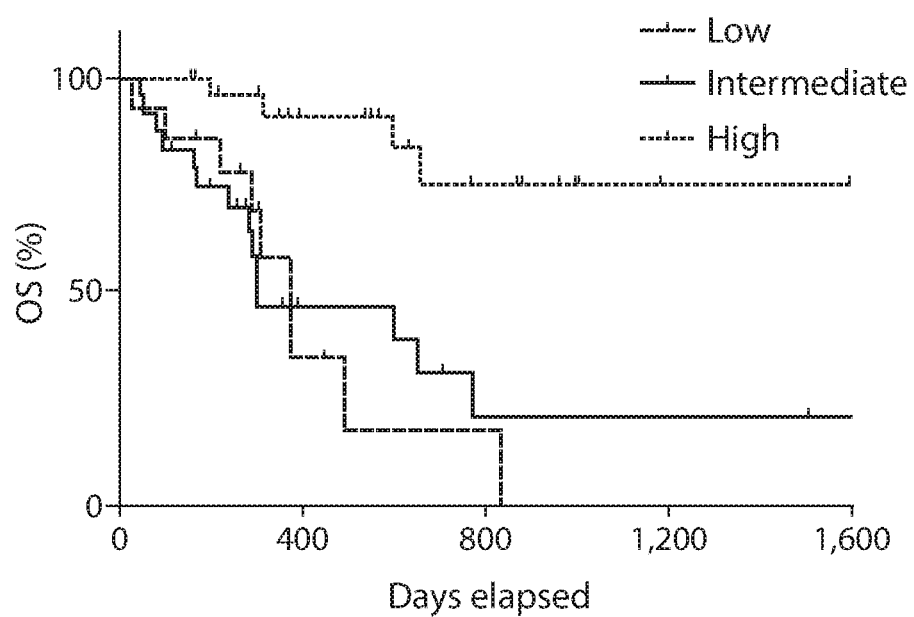
FIG. 1D depicts the overall survival in patients with high, intermediate, and low mutational load.

Other clinical outcomes were then evaluated. Across both cohorts, progression-free survival (PFS) correlated with mutation load; superior PFS was observed in the high mutation load group compared to the intermediate and low groups (median not reached vs. 89 days vs. 86 days, P<0.001; FIG. 1C). Overall survival (OS) followed a similar pattern (median not reached vs. 300 days vs. 375 days, P<0.001; FIG. 1D). Notably, although ORR seemed higher in the intermediate than in the low mutation load group, PFS and OS appeared similar between these groups. High mutation load was also associated with superior OS and PFS using Cox proportional hazards model, adjusted for age, gender, stage, and prior ipilimumab (high vs. low HR, 0.14, P<0.001 for PFS; HR, 0.09, P<0.001 for OS; Tables 6-7).

TABLE 6

Cox proportional hazards model of OS adjusting for baseline variables

| VARIABLE | COEFFICIENT (β) | STANDARD ERROR (β) | P VALUE | HR | 95% CI* |
|---|---|---|---|---|---|
| MUTATIONAL LOAD GROUP | | | | | |
| Intermediate vs. Low | −0.22 | 0.48 | 0.64 | 0.80 | (0.31, 2.0) |
| High vs. Low | −2.39 | 0.65 | 0.0002 | 0.09 | (0.02, 0.32) |
| AGE | −0.01 | 0.02 | 0.54 | 0.99 | (0.95, 1.0) |
| GENDER | | | | | |
| M vs. F | 0.49 | 0.48 | 0.30 | 1.64 | (0.64, 4.2) |
| STAGE | | | | | |
| IVc vs. IIIC-IVb | 0.29 | 0.64 | 0.65 | 1.33 | (0.38, 4.67) |
| PRIOR IPILIMUMAB | | | | | |
| Yes vs. No | 1.35 | 0.47 | 0.004 | 3.85 | (1.53, 9.69) |

*CI: confidence interval

TABLE 7

Cox proportional hazards model of PFS adjusting for baseline variables

| VARIABLE | COEFFI-CIENT ($\beta$) | STAN-DARD ERROR ($\beta$) | P VALUE | HR | 95% CI* |
|---|---|---|---|---|---|
| MUTATIONAL LOAD GROUP | | | | | |
| Intermediate vs. Low | −0.10 | 0.40 | 0.80 | 0.90 | (0.41, 1.99) |
| High vs. Low | −2.00 | 0.48 | <0.0001 | 0.14 | (0.05, 0.35) |
| AGE | 0.0002 | 0.01 | 0.99 | 1.0 | (0.97, 1.0) |
| GENDER | | | | | |
| M vs. F | −0.20 | 0.34 | 0.54 | 0.81 | (0.42, 1.58) |
| STAGE | | | | | |
| IVc vs. IIIC-IVb | −0.10 | 0.44 | 0.82 | 0.90 | (0.38, 2.16) |
| PRIOR IPILIMUMAB | | | | | |
| Yes vs. No | 0.20 | 0.35 | 0.56 | 1.23 | (0.62, 2.44) |

*CI: confidence interval

Figure 3A:
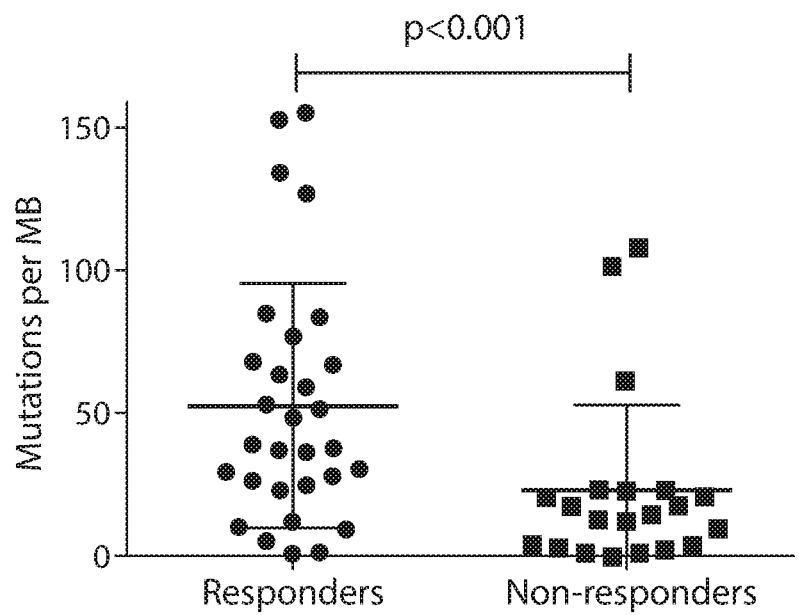
FIG. 3A depicts the mutational load in tumors with cutaneous/unknown primaries in responders vs. non-responders.
Figure 3B:
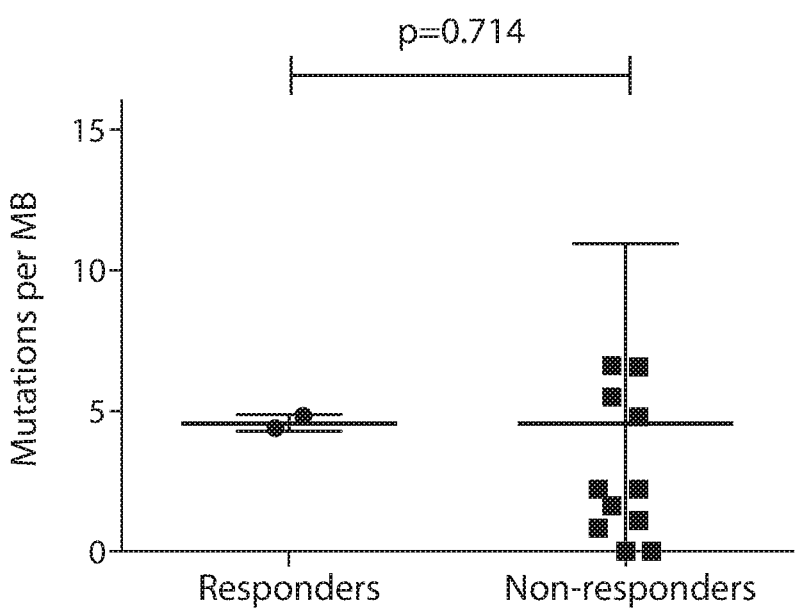
FIG. 3B depicts the mutational load in tumors with non-cutaneous primaries (acral, mucosal, uveal) in responders vs. non-responders.

Non-cutaneous melanomas (including acral subtype) have far fewer mutations than those of cutaneous origin, and perhaps less frequent responses to immune therapy, whereas the mutational profile of melanomas of unknown origin mirrors cutaneous melanomas (Hodis E, Watson I R, Kryukov G V, et al. Cell 150:251-63, 2012; Krauthammer et al. Nat Genet 44:1006-14, 2012; Postow et al. Oncologist 18:726-32, 2013; Luke et al. Cancer, 2013; Johnson et al. Oncologist 20:648-52, 2015). To exclude confounding from non-cutaneous melanomas, mutational load in melanomas of cutaneous/unknown origin was assessed separately and a higher mutation load was observed in responders (median, 39.0 vs. 14.4 mutations/MB, P<0.001; FIG. 3A). No difference in mutational load was identified in 14 patients (albeit with only 2 responders) in patients with non-cutaneous melanomas (median, 4.5 vs. 2.2 mutations/MB, P=0.714; FIG. 3B).

Figure 3C:
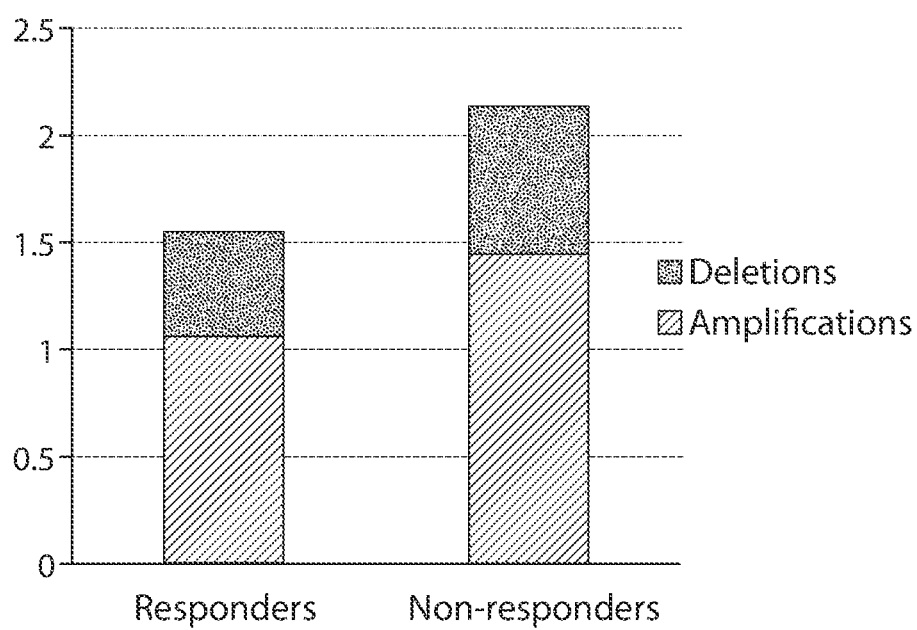
FIG. 3C depicts gene amplifications and deletions in responders vs. non-responders.
Figure 4A:
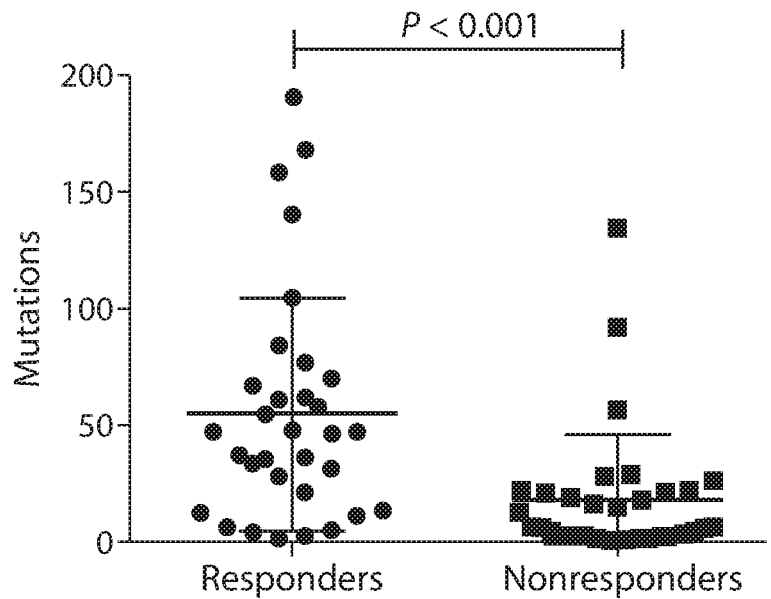
FIG. 4A depicts the total number of mutations observed in responders versus nonresponders.
Figure 4B:
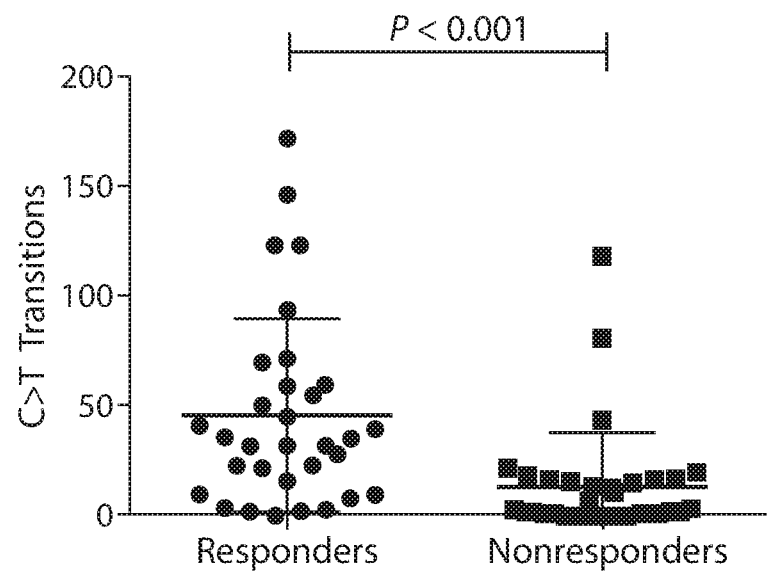
FIG. 4B depicts the total number of C>T transitions observed in responders versus nonresponders.
Figure 4C:
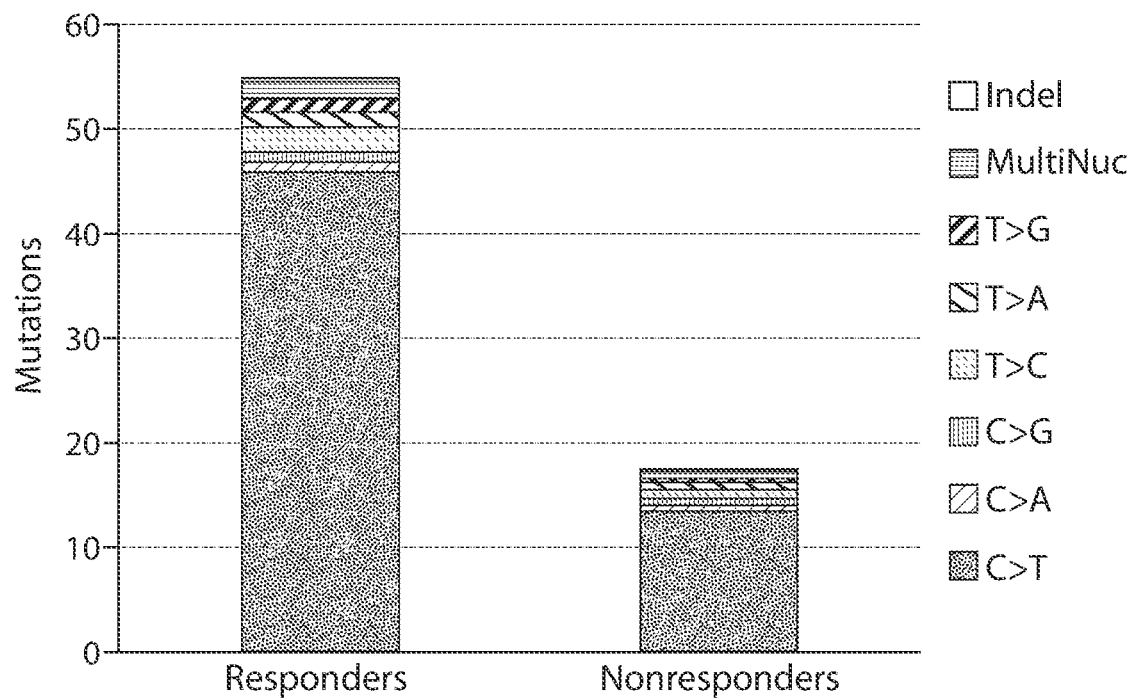
FIG. 4C depicts the types of nucleotide alterations observed in responders versus nonresponders.

Next, whether particular types of genomic changes correlated with response was assessed. Total identified mutations (including those with known or likely functional significance) were strongly associated with response to therapy (median 46.5 vs. 6.0 mutations, p<0.001; FIG. 4A). It was also found that C>T transitions (highly associated with ultraviolet radiation damage), were more numerous in responders (median 33.5 vs. 3.0 transitions, p<0.001; FIG. 4B). Most other nucleotide variants also occurred more commonly in responders, albeit at lower frequencies (FIG. 4C). By contrast, gene amplifications and deletions were similar between groups (FIG. 3C).

Figure 4D:
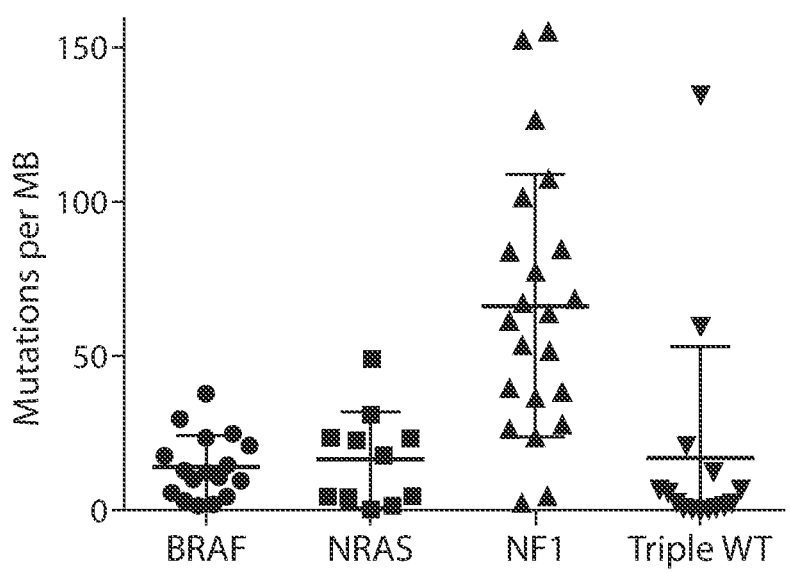
FIG. 4D depicts the mutational load of patients with BRAF mutations, NRAS mutations, NF1 mutations/loss, and "triple WT" (defined as wild-type for BRAF, NRAS, and NF1). BRAF non-V600 mutations were included with in the BRAF cohort except for 1 patient with concurrent NF1 mutation. One patient with NRAS$^{Q61R}$ mutation and concurrent NF1 mutation was included in the NRAS cohort.

Whether mutational load differed between particular "driver mutation"-defined subsets was then investigated. Marked differences were observed between BRAF, NRAS, NF1, and "triple WT" (wild type) melanomas (median 12.0 vs. 17.6 vs. 62.7 vs. 2.2 mutations/MB respectively, p<0.001) (FIG. 4D). Melanomas with NF1 mutations have been linked with chronic ultraviolet light damage and high mutational loads previously (Cancer Genome Atlas Network. Cell 161:1681-96, 2015; Krauthammer et al. Nat Genet 44:1006-14, 2012). By contrast, the "triple WT" group harbored an extremely low mutational load.

Figure 5A:
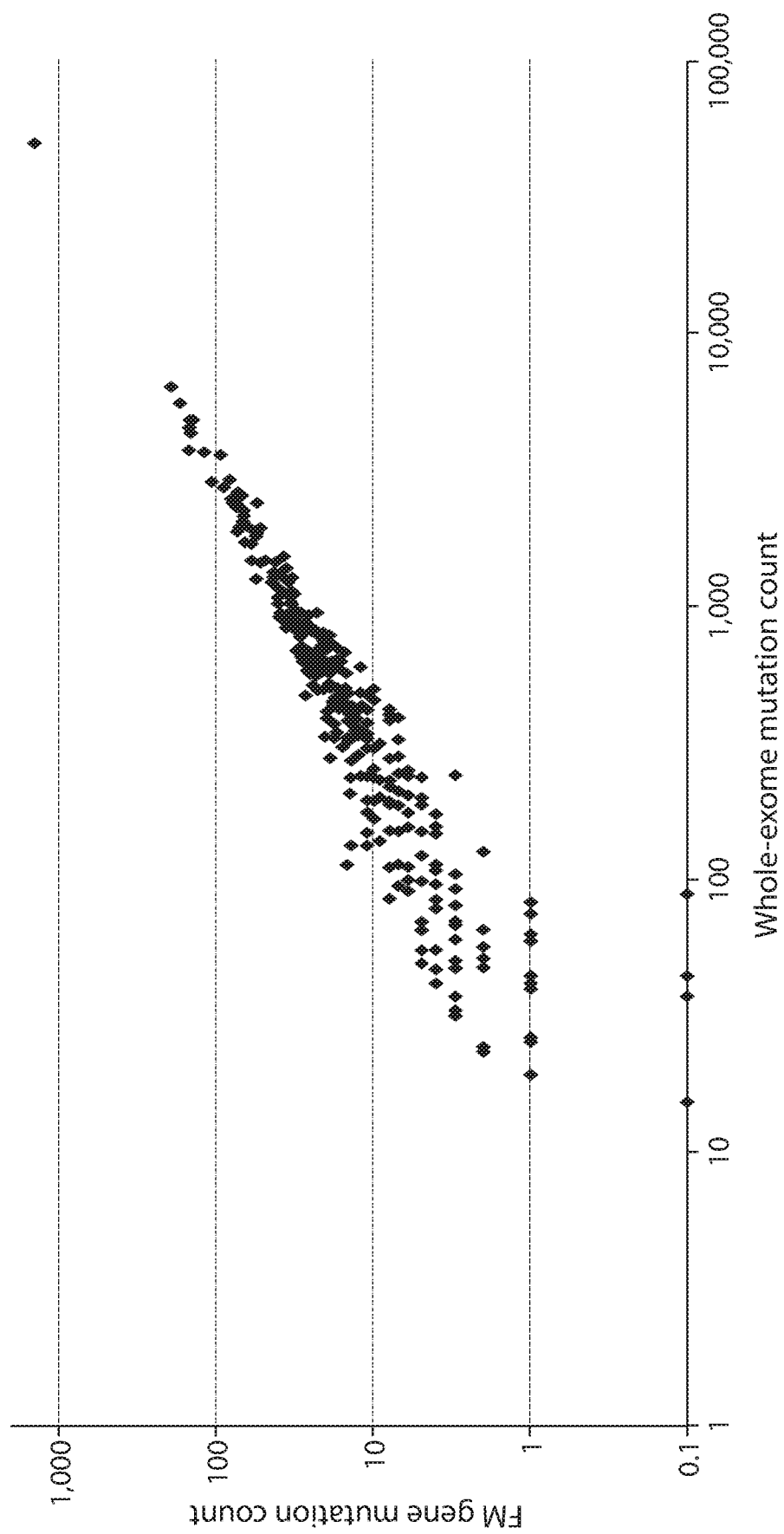
FIG. 5A depicts that the mutational load in TCGA skin cutaneous melanoma (SKCM) samples using 315 genes included on a hybrid capture NGS panel is highly correlated with mutations assessed by whole exome sequencing.
Figure 5B:
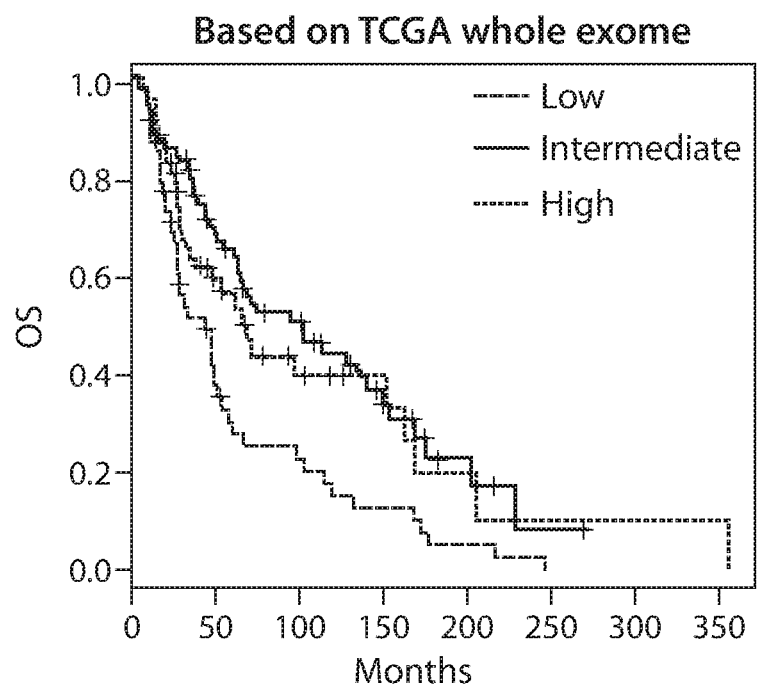
FIG. 5B depicts the mutational load groups and survival in the TCGA using whole exome sequencing (WES).
Figure 5C:
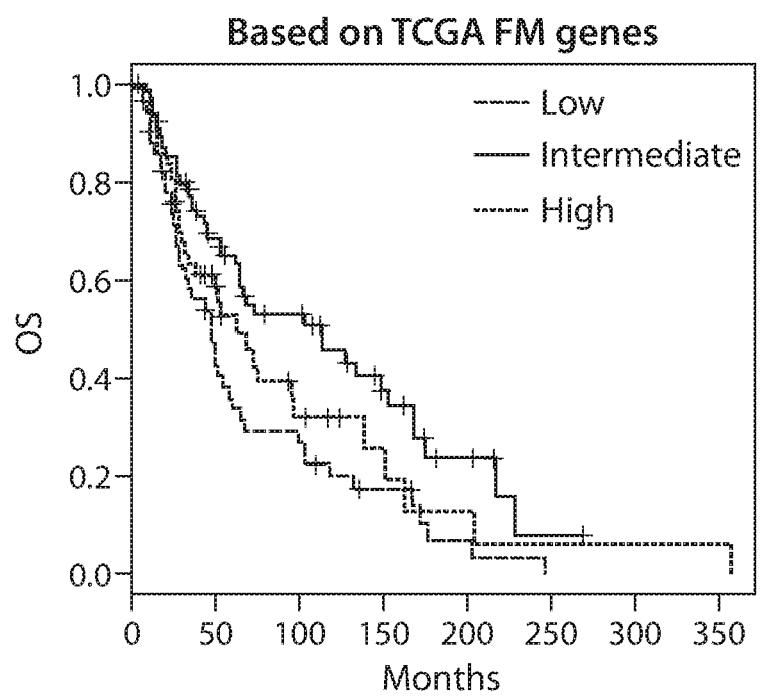
FIG. 5C depicts the mutational load groups and survival in the TCGA using 315 tested (FM) genes.

To determine whether mutation load in the 236-315 genes sequenced in this hybrid capture-based NGS panel could serve as a robust correlate for total genomic mutational load by WES, 345 archival TCGA samples were assessed (Cancer Genome Atlas Network. Electronic address imo, Cancer Genome Atlas N: Genomic Classification of Cutaneous Melanoma. Cell 161:1681-96, 2015). The total number of mutations identified in these genes strongly correlated with total exome mutation number in these samples (R=0.995, p<0.001; FIG. 5A). This correlation appeared particularly robust in samples with high mutational loads. To assess whether mutational load associated with improved outcomes in unselected patients (not receiving anti-PD-1/PD-L1), survival among TCGA samples with evaluable survival data (n=263) was assessed. No significant correlation was observed using the tested genes (P=0.14) or WES (P=0.06). For low, intermediate, and high mutation load groups, a difference in OS using WES (median, OS 43.4 months vs. 103.0 months vs. 68.0 months, P=0.001) and tested genes (median, 47.3 vs. 112.5 months vs. 61.5 months, P=0.008). Using three mutation load groups, patients with intermediate mutational load experienced the longest survival (HR=2.1 for intermediate vs. low, P=0.008; FIGS. 5B-5C).

Specific Mutations and Response to an Anti-PD-1 or Anti-PD-L1 Therapy

Figure 6:
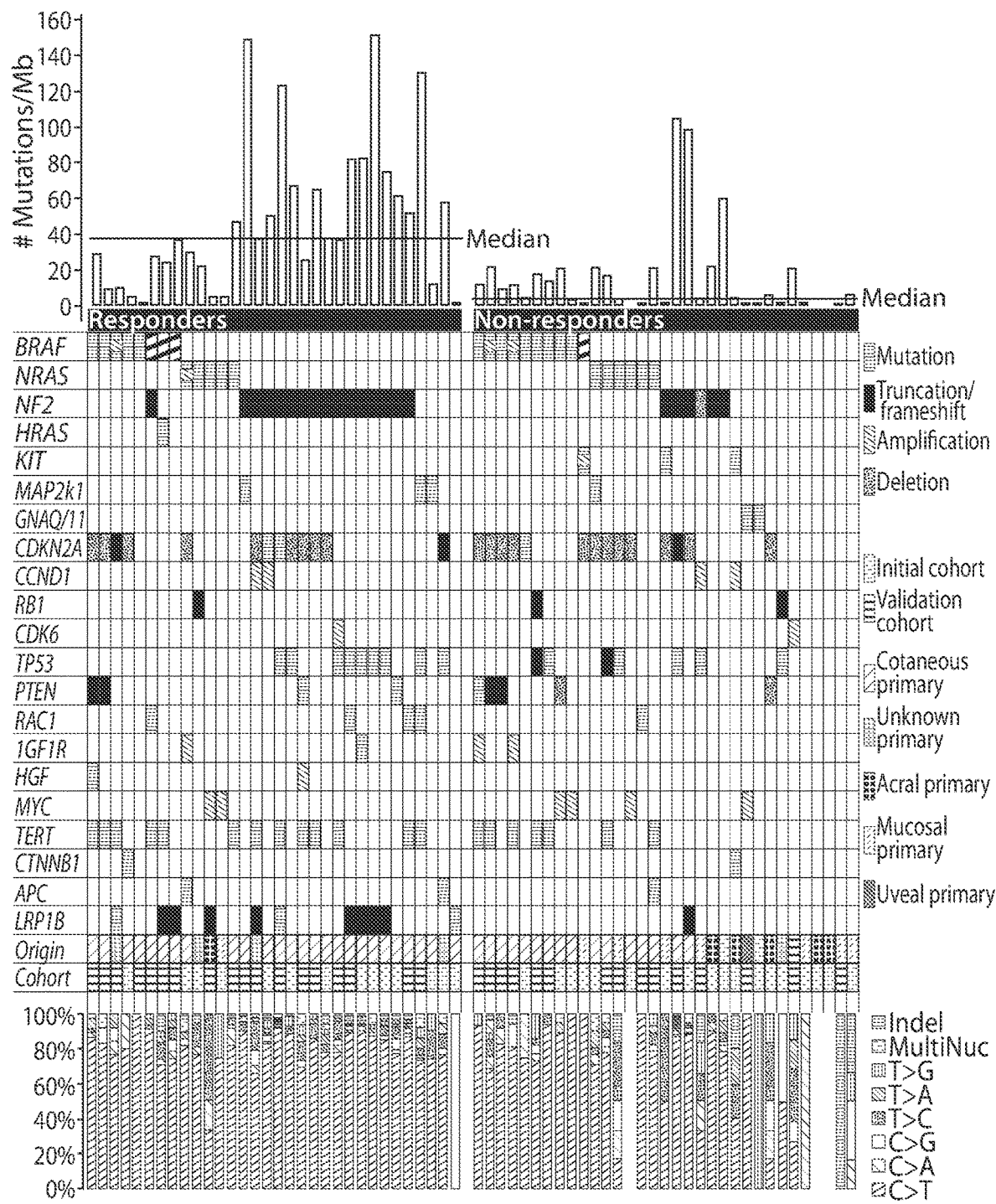
FIG. 6 depicts the calculated mutational load per sample (top); color-coded matrix of individual mutations, copy-number alterations; and clinical characteristics (middle); and mutation spectra of individual samples (bottom).

Next, mutations in particular cancer-related genes were examined to assess their impact on response to anti-PD-1. This analysis focused on previously-described alterations predicted to be functional, and variants of unknown significance (VUS) were excluded unless noted. Several genes that were more frequently altered in responders or non-responders were identified (Table 8, FIG. 6). Some genomic alterations correlated with mutational load; for example, NF1 alterations were more common in responders (50% vs. 21%, p=0.015; ORR 74%) whereas "triple WT" patients were more often in the non-responding group (13% vs. 35%, p=0.045). In smaller numbers, responses correlated with gene alterations previously linked to immunotherapy response (NRAS; Johnson et al. Cancer Immunol Res 3:288-95, 2015), T cell exclusion (CTNNB1; Spranger et al. Nature, 523:231-5, 2015), or PD-L1 regulation (MYC; Casey et al. Science 352:227-31, 2016). Loss of PTEN has been linked to PD-L1 expression (in glioblastoma) and immunosuppressive cytokine profiles (in melanoma) (Peng et al. Cancer Discov, 2015). Although both patients with PTEN loss failed to respond, a significant difference in the incidence of PTEN-inactivating mutations when comparing responders vs. non-responders (13% vs. 15%, p=0.76). MYC amplification appeared to ber more common in non-responders, but conclusions were limited by sample size. BRCA2 mutations (including VUS) appeared more common in responders (5 of 32) compared with nonresponders (2 of 33); melanomas with BRCA2 mutations had higher mutational load than those lacking these mutations (median, 68.2 vs. 15.9 mut/MB; P=0.028; Hugo et al. Cell 165:35-44, 2016).

TABLE 8

Altered genes in responders and non-responders

| Gene | Responders (n = 32) Number (%) | Non-responders (N = 33) Number (%) | P value |
|---|---|---|---|
| BRAF V600 | 5 (16) | 9 (27) | 0.25 |
| BRAF non-V600 | 3 (9) | 1 (3) | 0.29 |
| NRAS | 5 (16) | 6 (18) | 0.78 |
| NF1 | 16 (50) | 7 (21) | 0.02 |
| "Triple WT"* | 4 (13) | 11 (33) | 0.05 |

TABLE 8-continued

Altered genes in responders and non-responders

| Gene | Responders (n = 32) Number (%) | Non-responders (N = 33) Number (%) | P value |
|---|---|---|---|
| TP53 | 9 (28) | 7 (21) | 0.57 |
| MYC | 2 (6) | 4 (12) | 0.41 |
| APC/CTNNB1 | 3 (9) | 2 (6) | 0.61 |
| IGF1R/HGF | 4 (13) | 2 (6) | 0.37 |
| PTEN | 4 (13) | 5 (15) | 0.76 |
| CDKN2A/CDK4/ CDK6/RB1 alterations | 14 (44) | 19 (58) | 0.27 |
| LRP1B | 11 (34) | 1 (3) | 0.001 |

LRP1B Mutations and Total Mutation Burden

Figure 7A:
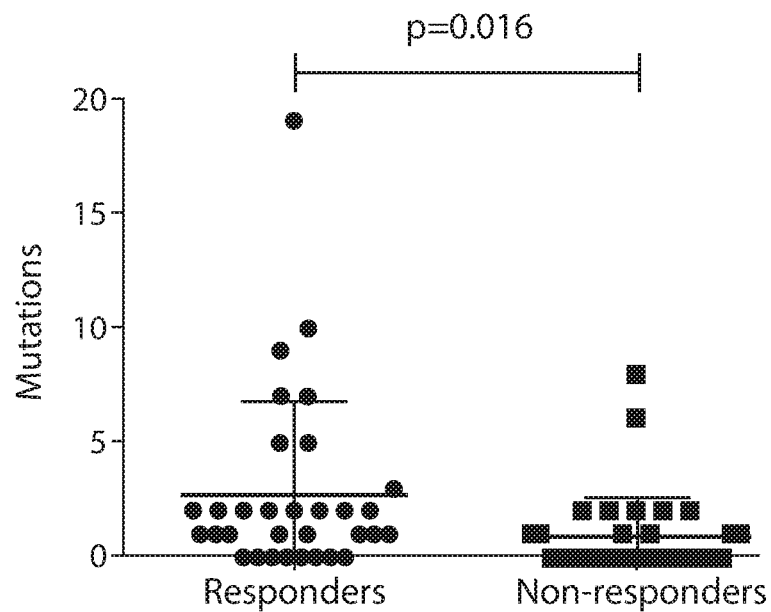
FIG. 7A depicts the LRP1B mutations/variants of unknown significance in responders vs. non-responders.
Figure 7B:
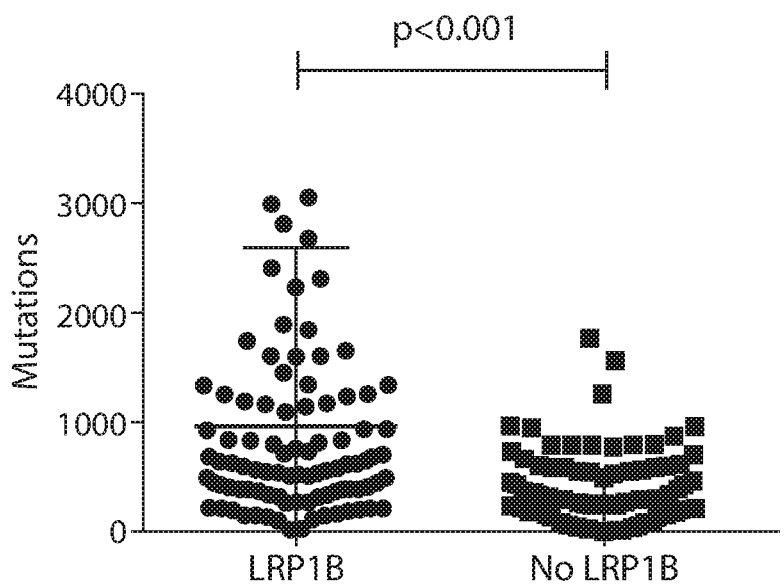
FIG. 7B depicts the total number of mutations among melanomas with and without LRP1B mutations.
Figure 7C:
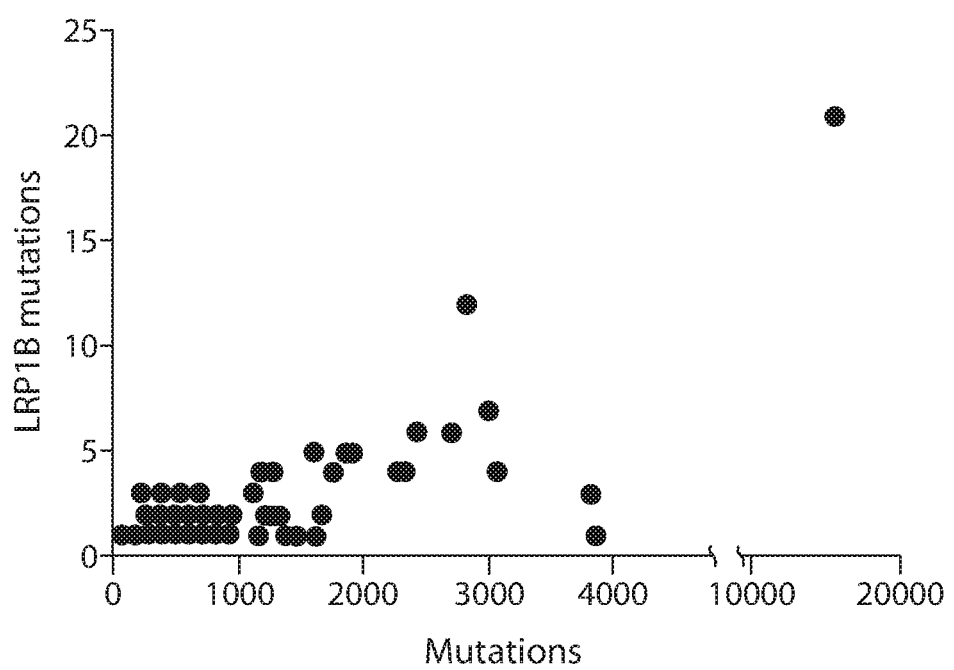
FIG. 7C depicts the association between the number of LRP1B mutations and total mutations in the melanoma TCGA.

Frequent mutations in LRP1B were observed. This putative tumor suppressor is a large, 1.9-MB gene designated a common fragile site (region of profound genomic instability; Smith et al. *Cancer Lett* 232:48-57, 2006). The hypothesis was that mutations detected herein might serve as a single gene surrogate for total mutational burden and response (a "biometer" of total exonic mutational load). Among responders, 11 patients harbored LRP1B mutations compared with 1 non-responder (34% vs. 3%, P=0.008). When extended to VUS, responders had on average 2.8 mutations/VUS compared with 0.9 for non-responders (P=0.016; FIG. 7A); 75% of responders had ≥1 mutation/VUS compared to 38% of non-responders (p=0.002). To investigate in a larger population, the TCGA was queried (Cancer Genome Atlas Network. *Cell* 161:1681-96, 2015). Melanomas with LRP1B mutations had significantly more total mutations compared with those lacking LRP1B mutations (median 542 vs. 219, p<0.001; FIG. 7B), and mutational load correlated with number of LRP1B mutations per tumor (Spearman's R=0.54, p<0.001; FIG. 7C). These data suggest that sequencing even a single, frequently mutated gene can provide insight into genome-wide mutational load and even correlate with anti-PD-1 responses. It remains unclear whether LRP1B mutations have intrinsic immune effects.

Figure 8A:
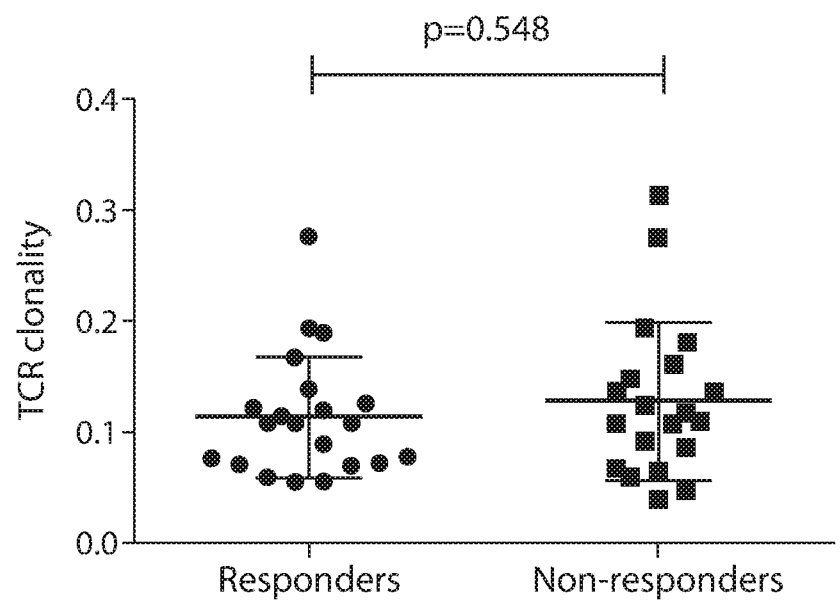
FIG. 8A depicts the T cell receptor (TCR) clonality in responders vs. non-responders.
Figure 8B:
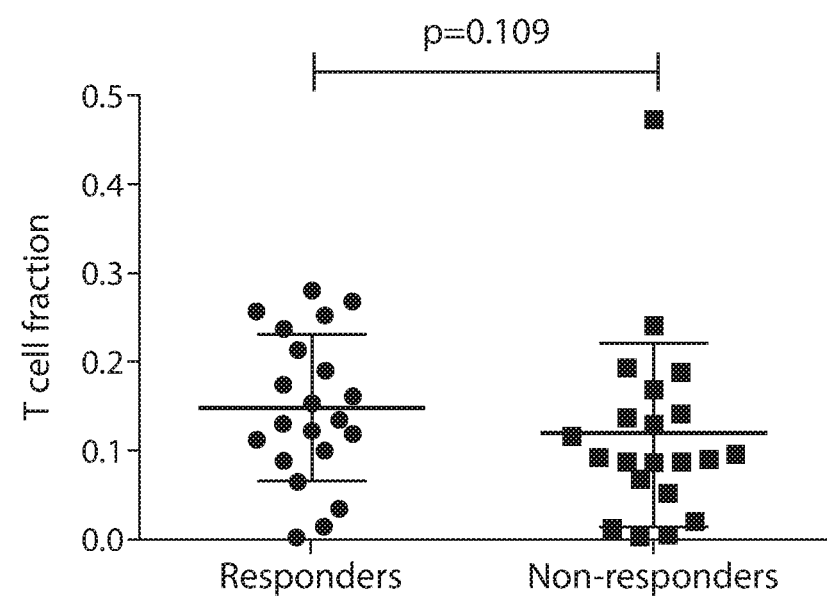
FIG. 8B depicts the T cell fraction in responders vs. non-responders.
Figure 8C:
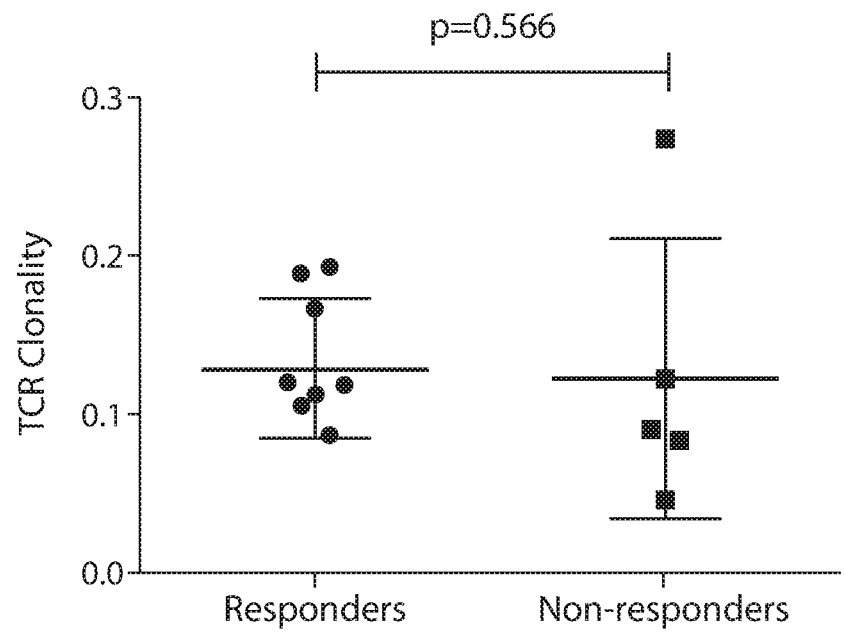
FIG. 8C depicts the TCR clonality in responders vs. non-responders in "ideal" samples, defined as those obtained within 4 months of anti-PD-1/anti-PD-L1 treatment without other prior therapies.
Figure 8D:
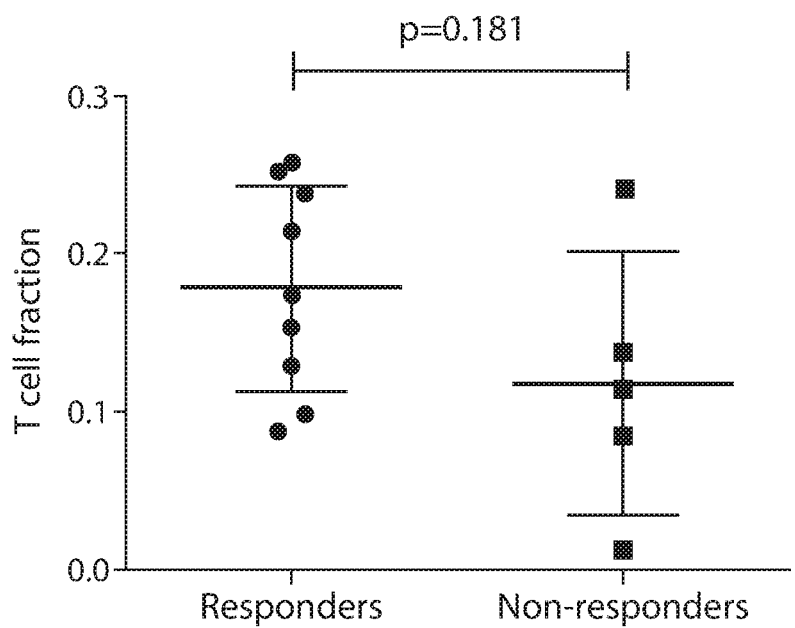
FIG. 8D depicts the T cell fraction in these "ideal" samples, defined as those obtained within 4 months of anti-PD-1/anti-PD-L1 treatment without other prior therapies.
Figure 9A:
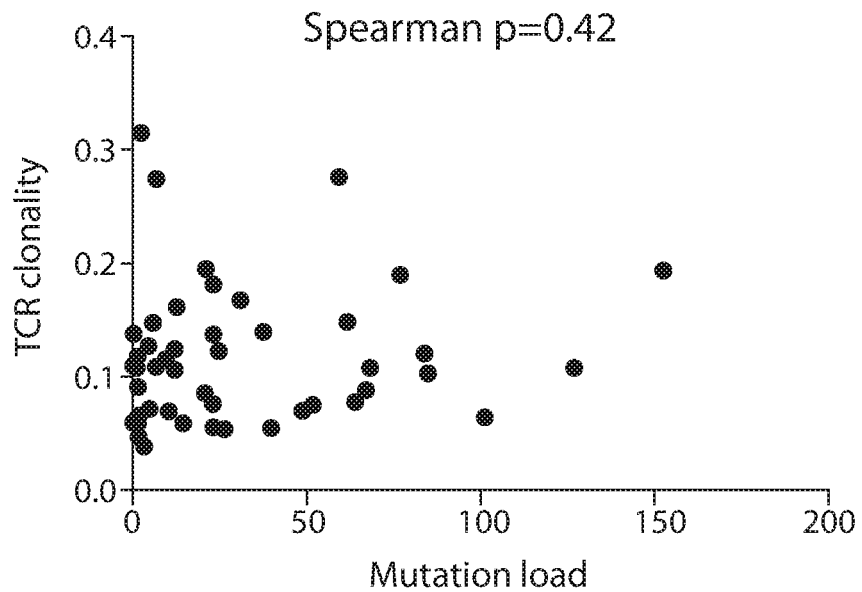
FIG. 9A depicts the correlation between mutation load and T cell receptor (TCR) clonality.
Figure 9B:
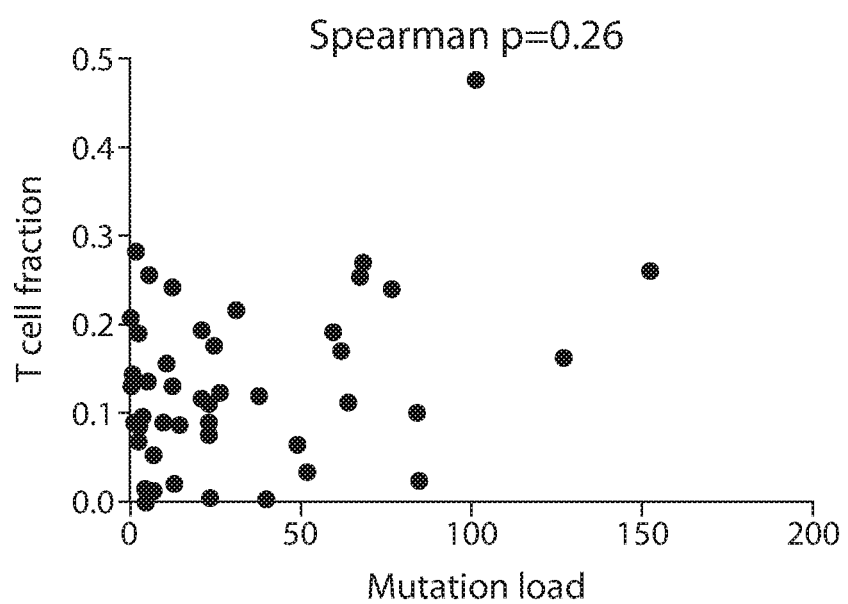
FIG. 9B depicts the correlation between mutation load and T cell fraction.

T Cell Receptor (TCR) Clonality does not Correlate with Clinical Benefit or Mutational Load It was then investigated whether T cell infiltration and clonality correlated with mutational load and could enhance the predictive capacity of this approach by performing TCR NGS in available tumor samples (n=42). Increased clonality (and decreased diversity) of the TCR β-chain repertoire may indicate preexisting infiltration of tumor-specific antigen populations and has been linked with response to anti-PD-1 (Tumeh et al. *Nature* 515:568-71, 2014). It was observed that TCR clonality did not correlate with response to anti-PD-1 (median 0.11 vs. 0.11, P=0.54; FIG. 8A). Furthermore, T cell fraction did not correlate with response (median 0.13 vs. 0.09, P=0.11; FIG. 8B). Since time or intervening therapies may modulate TCR clonality/T-cell infiltration, a subset of samples obtained within 4 months of starting anti-PD-1 without any interval therapies were assessed. Among this group (n=14), nonstatistically significant trends to increasing clonality and T cell fraction among responders were observed (FIGS. 8C-8D; Tumeh et al. *Nature* 515:568-71, 2014). T-cell clonality and T-cell fraction also did not correlate with mutational load (FIGS. 9A-9B).

In this study, it was found that mutational number as detected by a several hundred gene hybrid capture-based NGS platform strongly correlated with benefit from anti-PD-1/anti-PD-L1. The link between anti-PD-1 responses and mutation load in melanoma was demonstrated and validated. In particular, stratifying patients into groups (e.g., "high," "intermediate," and "low" mutation load cohorts) provided a clinically feasible marker of response to anti-PD-1/anti-PD-L1 in advanced melanoma and perhaps other cancers. No differences in survival were noted between the "intermediate" and "low" mutation load groups in this study, which could imply the presence of a "threshold effect," and that the effect on response and survival may be most pronounced in the "high" mutation load group.

Alterations in several genes correlated with benefit from anti-PD-1. Although certain genetic changes may directly influence the immune microenvironment, the findings suggest that other alterations may simply correlate with or contribute to increased mutational load (e.g., NF1, LRP1B, and BRCA2).

To summarize, mutational load in advanced melanoma as determined by a hybrid capture-based NGS platform strongly correlated with response to an anti-PD-1 or anti-PD-L1 therapy in two independent cohorts. This was especially marked in the "high" mutational load group, which comprised >40% of studied samples. These data suggest that testing of mutational load by this rigorously validated approach can improve treatment decision-making, allow more rational use of costly agents, and enhance this new era of precision immunotherapy.

Incorporation by Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments described herein. Such equivalents are intended to be encompassed by the following claims.

We claim:

1. A method of treating a subject having a melanoma, the method comprising:
   (a) acquiring a value of responder status to a therapy comprising an inhibitor of PD-1 or PD-L1 for the subject, wherein said value of responder status comprises a measure of the tumor mutational burden (TMB) in a melanoma sample, or in a sample derived from the melanoma, from the subject, wherein the measure of the TMB comprises a determination of the number of one or more somatic alterations in a predetermined set of genes including ABL1, ABL2, ACVR1B, AKT1, AKT2, AKT3, ALK, AMER1, APC, AR, ARAF, ARFRP1, ARID1A, ARID1B, ARID2, ASXL1, ATM, ATR, ATRX, AURKA, AURKB, AXIN1, ALX, BAP1, BARD1, BCL2, BCL2L1, BCL2L2, BCL6, BCOR, BCORL1, BLM, BRAF, BRCA1, BRCA2, BRD4, BRIP1, BTG1, BTK, C11orf30, CARD11, CBFB, CBL, CCND1, CCND2, CCND3, CCNE1, CD274, CD79A, CD79B, CDC73, CDH1, CDK12, CDK4, CDK6, CDK8, CDKN1A, CDKN1B, CDKN2A, CDKN2B, CDKN2C, CEBPA, CHD2, CHD4, CHEK1, CHEK2, CIC, CREBBP, CRKL, CRLF2, CSF1R, CTCF, CTNNA1, CTNNB1, CUL3, CYLD, DAXX, DDR2, DICER1, DNMT3A, DOT1L, EGFR, EP300, EPHA3, EPHA5, EPHA7, EPHB1, ERBB2, ERBB3, ERBB4, ERG, ERRFI1, ESR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR1, FGFR2, FGFR3, FGFR4, FH, FLCN, FLT1, FLT3, FLT4, FOXL2, FOXP1, FRS2, FUBP1, GABRA6, GATA1, GATA2, GATA3, GATA4, GATA6, GID4, GLI1, GNA11, GNA13, GNAQ, GNAS, GPR124, GRIN2A, GRM3, GSK3B, H3F3A, HGF, HNF1A, HRAS, HSD3B1, HSP9OAA1, IDH1, IDH2, IGF1R, IGF2, IKBKE, IKZF1, IL7R, INHBA, IRF2, IRF4, IRS2, JAK1, JAK2, JAK3, JUN, KAT6A, KDM5A, KDM5C, KDM6A, KDR, KEAP1, KEL, KIT, KLHL6, KMT2A, KMT2C, KMT2D, KRAS, LMO1, LRP1B, LYN, LZTR1, MAGI2, MAP2K1, MAP2K2, MAP2K4, MAP3K1, MCL1, MDM2, MDM4, MED12, MEF2B, MEN1, MET, MITF, MLH1, MPL, MRE11A, MSH2, MSH6, MTOR, MUTYH, MYC, MYCL, MYCN, MYD88, NF1, NF2, NFE2L2, NFKB1A, NKX2-1, NOTCH1, NOTCH2, NOTCH3, NPM1, NRAS, NSD1, NTRK1, NTRK2, NTRK3, NUP93, PAK3, PALB2, PARK2, PAX5, PBRM1, PDCD1LG2, PDGFRA, PDGFRB, PDK1, PIK3C2B, PIK3CA, PIK3CB, PIK3CG, PIK3R1, PLCG2, PMS2, POLD1, POLE, PPP2R1A, PRDM1, PREX2, PRKAR1A, PRKCI, PRKDC, PRSS8, PTCH1, PTEN, PTPN11, QKI, RAC1, RAD50, RAD51, RAF1, RANBP2, RARA, RB1, RBM10, RET, RICTOR, RNF43, ROS1, RPTOR, RUNX1, RUNX1T1, SDHA, SDHB, SDHC, SDHD, SETD2, SF3B1, SLIT2, SMAD2, SMAD3, SMAD4, SMARCA4, SMARCB1, SMO, SNCAIP, SOCS1, SOX10, SOX2, SOX9, SPEN, SPOP, SPTA1, SRC, STAG2, STAT3, STAT4, STK11, SUFU, SYK, TAF1, TBX3, TERC, TERT (promoter only), TET2, TGFBR2, TNFAIP3, TNFRSF14, TOP1, TOP2A, TP53, TSC1, TSC2, TSHR, U2AF1, VEGFA, VHL, WISP3, WT1, XPO1, ZBTB2, ZNF217, or ZNF703; wherein the one or more somatic alterations do not comprise one or more of the following: a rearrangement, a translocation, a functional alteration, or a germline mutation, and wherein the one or more somatic alterations are detected in the sample by hybrid capture followed by sequencing; and
   (b) responsive to an increased value of responder status, compared to a reference value of responder status, administering to the subject the therapy,
   thereby treating the subject.

2. The method of claim 1, wherein the subject has, or has been identified as having, an increased value of responder status, compared to a reference value of responder status.

3. The method of claim 1, wherein the therapy is administered to the subject responsive to the following in the sample from the subject:
   an increased number of the one or more somatic alterations in the predetermined set of genes, compared to a reference number of one or more somatic alterations in the predetermined set of genes, wherein the one or more somatic alterations do not comprise one or more of the following: a rearrangement, a translocation, a functional alteration, or a germline mutation.

4. The method of claim 1, wherein the therapy is administered to the subject, responsive to an increased level of TMB in the sample from the subject, compared to a reference level of TMB.

5. The method of claim 1, wherein the subject is identified as a responder to the therapy, when the sample from the subject has:
   an increased number of the one or more somatic alterations in the predetermined set of genes, compared to a reference number of one or more somatic alterations in the predetermined set of genes, wherein the one or more somatic alterations do not comprise one or more of the following: a rearrangement, a translocation, a functional alteration.

6. The method of claim 1, wherein the subject is identified as a non-responder to the therapy, when the sample from the subject has the following:
   a decreased or unchanged number of the one or more somatic alterations in the predetermined set of genes, compared to a reference number of one or more somatic alterations in the predetermined set of genes, wherein the one or more somatic alterations do not comprise one or more of the following: a rearrangement, a translocation, a functional alteration, or a germline mutation.

7. The method of claim 1, wherein the predetermined set of genes comprises at least about 50 or more, about 100 or more, about 150 or more, about 200 or more, about 250 or more, about 300 or more, or all of the genes including ABL1, ABL2, ACVR1B, AKT1, AKT2, AKT3, ALK, AMER1, APC, AR, ARAF, ARFRP1, ARID1A, ARID1B, ARID2, ASXL1, ATM, ATR, ATRX, AURKA, AURKB, AXIN1, ALX, BAP1, BARD1, BCL2, BCL2L1, BCL2L2, BCL6, BCOR, BCORL1, BLM, BRAF, BRCA1, BRCA2, BRD4, BRIP1, BTG1, BTK, C11orf30, CARD11, CBFB, CBL, CCND1, CCND2, CCND3, CCNE1, CD274, CD79A, CD79B, CDC73, CDH1, CDK12, CDK4, CDK6, CDK8, CDKN1A, CDKN1B, CDKN2A, CDKN2B, CDKN2C, CEBPA, CHD2, CHD4, CHEK1, CHEK2, CIC, CREBBP, CRKL, CRLF2, CSF1R, CTCF, CTNNA1, CTNNB1, CUL3, CYLD, DAXX, DDR2, DICER1, DNMT3A, DOT1L, EGFR, EP300, EPHA3, EPHA5, EPHA7, EPHB1, ERBB2, ERBB3, ERBB4, ERG, ERRFI1, ESR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR1, FGFR2, FGFR3, FGFR4, FH, FLCN, FLT1, FLT3, FLT4, FOXL2, FOXP1, FRS2, FUBP1, GABRA6, GATA1, GATA2, GATA3, GATA4, GATA6, GID4, GLI1, GNA11, GNA13, GNAQ, GNAS, GPR124, GRIN2A, GRM3, GSK3B, H3F3A, HGF, HNF1A, HRAS, HSD3B1, HSP9OAA1, IDH1, IDH2, IGF1R, IGF2, IKBKE, IKZF1, IL7R, INHBA, IRF2, IRF4, IRS2, JAK1, JAK2, JAK3, JUN, KAT6A, KDM5A, KDM5C, KDM6A, KDR, KEAP1, KEL, KIT, KLHL6, KMT2A, KMT2C, KMT2D, KRAS, LMO1, LRP1B, LYN, LZTR1, MAGI2, MAP2K1, MAP2K2, MAP2K4, MAP3K1, MCL1, MDM2, MDM4, MED12, MEF2B, MEN1, MET, MITF, MLH1, MPL, MRE11A, MSH2, MSH6, MTOR, MUTYH, MYC, MYCL, MYCN, MYD88, NF1, NF2, NFE2L2, NFKB1A, NKX2-1, NOTCH1, NOTCH2, NOTCH3, NPM1, NRAS, NSD1, NTRK1, NTRK2, NTRK3, NUP93, PAK3, PALB2, PARK2, PAX5, PBRM1, PDCD1LG2, PDGFRA, PDGFRB, PDK1, PIK3C2B, PIK3CA, PIK3CB, PIK3CG, PIK3R1, PLCG2, PMS2, POLD1, POLE, PPP2R1A, PRDM1, PREX2, PRKAR1A, PRKCI, PRKDC, PRSS8, PTCH1, PTEN, PTPN11, QKI, RAC1, RAD50, RAD51, RAF1, RANBP2, RARA, RB1, RBM10, RET, RICTOR, RNF43, ROS1, RPTOR, RUNX1, RUNX1T1, SDHA, SDHB, SDHC, SDHD, SETD2, SF3B1, SLIT2, SMAD2, SMAD3, SMAD4, SMARCA4, SMARCB1, SMO, SNCAIP, SOCS1, SOX10, SOX2, SOX9, SPEN, SPOP, SPTA1, SRC, STAG2, STAT3, STAT4, STK11, SUFU, SYK, TAF1, TBX3, TERC, TERT (promoter only), TET2, TGFBR2, TNFAIP3, TNFRSF14, TOP1, TOP2A, TP53, TSC1, TSC2, TSHR, U2AF1, VEGFA, VHL, WISP3, WT1, XPO1, ZBTB2, ZNF217, or ZNF703.

8. The method of claim 1, further comprising, responsive to a measure of the tumor mutational burden, performing one, two, three or all of the following:
   (a) administering an altered dose of the therapy to the subject;
   (b) altering a schedule or time course of the therapy for the subject;
   (c) administering to a non-responder or a partial responder, an additional agent in combination with the therapy; or
   (d) prognosticating a time course in the progression of the melanoma in the subject.

9. The method of claim 1, wherein the determination of the number of the one or more somatic alterations in the predetermined set of genes comprises a determination of the number of a somatic alteration in about 25 or more, about 50 or more, about 100 or more, about 150 or more, about 200 or more, about 250 or more, about 300 or more, or all genes including ABL1, ABL2, ACVR1B, AKT1, AKT2, AKT3, ALK, AMER1, APC, AR, ARAF, ARFRP1, ARID1A, ARID1B, ARID2, ASXL1, ATM, ATR, ATRX, AURKA, AURKB, AXIN1, ALX, BAP1, BARD1, BCL2, BCL2L1, BCL2L2, BCL6, BCOR, BCORL1, BLM, BRAF, BRCA1, BRCA2, BRD4, BRIP1, BTG1, BTK, C11orf30, CARD11, CBFB, CBL, CCND1, CCND2, CCND3, CCNE1, CD274, CD79A, CD79B, CDC73, CDH1, CDK12, CDK4, CDK6, CDK8, CDKN1A, CDKN1B, CDKN2A, CDKN2B, CDKN2C, CEBPA, CHD2, CHD4, CHEK1, CHEK2, CIC, CREBBP, CRKL, CRLF2, CSF1R, CTCF, CTNNA1, CTNNB1, CUL3, CYLD, DAXX, DDR2, DICER1, DNMT3A, DOT1L, EGFR, EP300, EPHA3, EPHA5, EPHA7, EPHB1, ERBB2, ERBB3, ERBB4, ERG, ERRFI1, ESR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR1, FGFR2, FGFR3, FGFR4, FH, FLCN, FLT1, FLT3, FLT4, FOXL2, FOXP1, FRS2, FUBP1, GABRA6, GATA1, GATA2, GATA3, GATA4, GATA6, GID4, GLI1, GNA11, GNA13, GNAQ, GNAS, GPR124, GRIN2A, GRM3, GSK3B, H3F3A, HGF, HNF1A, HRAS, HSD3B1, HSP9OAA1, IDH1, IDH2, IGF1R, IGF2, IKBKE, IKZF1, IL7R, INHBA, IRF2, IRF4, IRS2, JAK1, JAK2, JAK3, JUN, KAT6A, KDMSA, KDMSC, KDM6A, KDR, KEAP1, KEL, KIT, KLHL6, KMT2A, KMT2C, KMT2D, KRAS, LMO1, LRP1B, LYN, LZTR1, MAGI2, MAP2K1, MAP2K2, MAP2K4, MAP3K1, MCL1, MDM2, MDM4, MED12, MEF2B, MEN1, MET, MITF, MLH1, MPL, MRE11A, MSH2, MSH6, MTOR, MUTYH, MYC, MYCL, MYCN, MYD88, NF1, NF2, NFE2L2 NFKB1A NKX2-1 NOTCH1 NOTCH2 NOTCH3 NPM1 NRAS NSD1 NTRK1 NTRK2, NTRK3, NUP93, PAK3, PALB2, PARK2, PAX5, PBRM1, PDCD1LG2, PDGFRA, PDGFRB, PDK1, PIK3C2B, PIK3CA, PIK3CB, PIK3CG, PIK3R1, PLCG2, PMS2, POLD1, POLE, PPP2R1A, PRDM1, PREX2, PRKAR1A, PRKCI, PRKDC, PRSS8, PTCH1, PTEN, PTPN11, QKI, RAC1, RAD50, RAD51, RAF1, RANBP2, RARA, RB1, RBM10, RET, RICTOR, RNF43, ROS1, RPTOR, RUNX1, RUNX1T1, SDHA, SDHB, SDHC, SDHD, SETD2, SF3B1, SLIT2, SMAD2, SMAD3, SMAD4, SMARCA4, SMARCB1, SMO, SNCAIP, SOCS1, SOX10, SOX2, SOX9, SPEN, SPOP, SPTA1, SRC, STAG2, STAT3, STAT4, STK11, SUFU, SYK, TAF1, TBX3, TERC, TERT (promoter only), TET2, TGFBR2, TNFAIP3, TNFRSF14, TOP1, TOP2A, TP53, TSC1, TSC2, TSHR, U2AF1, VEGFA, VHL, WISP3, WT1, XPO1, ZBTB2, ZNF217, or ZNF703 set forth in Table 1.

10. The method of claim 1, wherein the therapy is administered to the subject, responsive to:
   (i) an increased number of the one or more somatic alterations in the predetermined set of genes, compared to the reference number of one or more somatic alterations in the predetermined set of genes, wherein the one or more somatic alterations do not comprise one or more of the following: a rearrangement, a translocation, a functional alteration, or a germline mutation;
   (ii) a determination that the number of somatic alterations in the predetermined set of genes is about 3.3 or more, about 5 or more, about 10 or more, about 15 or more, about 20 or more, about 25 or more, about 30 or more, about 35 or more, about 40 or more, about 45 or more, or about 50 or more, somatic alterations per megabase in the coding regions of the predetermined set of genes; or (iii) a determination that the number of somatic alterations in the predetermined set of genes is about 23.1 more, about 25 or more, about 30 or more, about 35 or more, about 40 or more, about 45 or more, or about 50 or more, somatic alterations per megabase in the coding regions of the predetermined set of genes.

11. The method of claim 1, wherein the subject is receiving, or has received, a different therapy comprising a therapeutic agent or modality other than an inhibitor of PD-1 or PD-L1.

12. The method of claim 11, wherein:
(i) the therapy is administered: after cessation of the different therapy, or in combination with the different therapy;
(ii) the different therapy is chosen from a chemotherapy, a radiation therapy, an immunotherapy, an immunoradiotherapy, an oncolytic virotherapy, a surgical procedure, or any combination thereof; or
(iii) the different therapy comprises one or more of: dacarbazine, temozolomide, interleukin-2 (IL-2), an interferon, ipilimumab, a BRAF inhibitor, a MEK inhibitor, talimogene laherparepvec, an adoptive cell transfer, or any combination thereof.

13. The method of claim 1, wherein:
(i) the inhibitor of PD-1 is an anti-PD-1 antibody;
(ii) the inhibitor of PD-1 is chosen from nivolumab (ONO-4538, BMS-936558, or MDX1106), pembrolizumab (MK-3475 or lambrolizumab), pidilizumab (CT-011), MEDI0680 (AMP-514), PDR001, REGN2810, BGB-108, BGB-A317, SHR-1210 (HR-301210, SHR1210, or SHR-1210), PF-06801591, or AMP-224;
(iii) the inhibitor of PD-L1 is an anti-PD-L1 antibody; or
(iv) the inhibitor of PD-L1 is chosen from atezolizumab (MPDL3280A, RG7446, or RO5541267), YW243.55.S70, MDX-1105, durvalumab (MEDI4736), or avelumab (MSB0010718C).

14. A method of selecting a therapy comprising an inhibitor of PD-1 or PD-L1 for a subject having a melanoma, the method comprising:
acquiring a value of responder status to the therapy for the subject,
wherein said value of responder status comprises a measure of the tumor mutational burden (TMB) in a melanoma sample, or in a sample derived from the melanoma, from the subject, wherein the measure of the TMB comprises a determination of the number of one or more somatic alterations in a predetermined set of genes including ABL1, ABL2, ACVR1B, AKT1, AKT2, AKT3, ALK, AMER1, APC, AR, ARAF, ARFRP1, ARID1A, ARID1B, ARID2, ASXL1 ATM, ATR, ATRX, AURKA, AURKB, AXIN1, ALX, BAP1, BARD1, BCL2, BCL2L1, BCL2L2, BCL6, BCOR, BCORL1, BLM, BRAF, BRCA1, BRCA2, BRD4, BRIP1, BTG1, BTK, C11orf30, CARD11, CBFB, CBL, CCND1, CCND2, CCND3, CCNE1, CD274, CD79A, CD79B, CDC73, CDH1, CDK12, CDK4, CDK6, CDK8, CDKN1A, CDKN1B, CDKN2A, CDKN2B, CDKN2C, CEBPA, CHD2, CHD4, CHEK1, CHEK2, CIC, CREBBP, CRKL, CRLF2, CSF1R, CTCF, CTNNA1, CTNNB1, CUL3, CYLD, DAXX, DDR2, DICER1, DNMT3A, DOT1L, EGFR, EP300, EPHA3, EPHA5, EPHA7, EPHB1, ERBB2, ERBB3, ERBB4, ERG, ERRFI1, ESR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR1, FGFR2, FGFR3, FGFR4, FH, FLCN, FLT1, FLT3, FLT4, FOXL2, FOXP1, FRS2, FUBP1, GABRA6, GATA1, GATA2, GATA3, GATA4, GATA6, GID4, GLI1, GNA11, GNA13, GNAQ, GNAS, GPR124, GRIN2A, GRM3, GSK3B, H3F3A, HGF, HNF1A, HRAS, HSD3B1, HSP9OAA1, IDH1, IDH2, IGF1R, IGF2, IKBKE, IKZF1, IL7R, INHBA, IRF2, IRF4, IRS2, JAK1, JAK2, JAK3, JUN, KAT6A, KDM5A, KDM5C, KDM6A, KDR, KEAP1, KEL, KIT, KLHL6, KMT2A, KMT2C, KMT2D, KRAS, LMO1, LRP1B, LYN, LZTR1, MAGI2, MAP2K1, MAP2K2, MAP2K4, MAP3K1, MCL1, MDM2, MDM4, MED12, MEF2B, MEN1, MET, MITF, MLH1, MPL, MRE11A, MSH2, MSH6, MTOR, MUTYH, MYC, MYCL, MYCN, MYD88, NF1, NF2, NFE2L2, NFKB1A, NKX2-1, NOTCH1, NOTCH2, NOTCH3, NPM1, NRAS, NSD1, NTRK1, NTRK2, NTRK3, NUP93, PAK3, PALB2, PARK2, PAX5, PBRM1, PDCD1LG2, PDGFRA, PDGFRB, PDK1, PIK3C2B, PIK3CA, PIK3CB, PIK3CG, PIK3R1, PLCG2, PMS2, POLD1, POLE, PPP2R1A, PRDM1, PREX2, PRKAR1A, PRKCI, PRKDC, PRSS8, PTCH1, PTEN, PTPN11, QKI, RAC1, RAD50, RAD51, RAF1, RANBP2, RARA, RB1, RBM10, RET, RICTOR, RNF43, ROS1, RPTOR, RUNX1, RUNX1T1, SDHA, SDHB, SDHC, SDHD, SETD2, SF3B1, SLIT2, SMAD2, SMAD3, SMAD4, SMARCA4, SMARCB1, SMO, SNCAIP, SOCS1, SOX10, SOX2, SOX9, SPEN, SPOP, SPTA1, SRC, STAG2, STAT3, STAT4, STK11, SUFU, SYK, TAF1, TBX3, TERC, TERT (promoter only), TET2, TGFBR2, TNFAIP3, TNFRSF14, TOP1, TOP2A, TP53, TSC1, TSC2, TSHR, U2AF1, VEGFA, VHL, WISP3, WT1, XPO1, ZBTB2, ZNF217, or ZNF703; wherein the one or more somatic alterations do not comprise one or more of the following: a rearrangement, a translocation, a functional alteration, or a germline mutation, and wherein the one or more somatic alterations are detected in the sample by hybrid capture followed by sequencing; and
wherein an increased value of responder status, compared to a reference value of responder status, indicates that: said subject is, or is likely to be, a responder to the therapy; or said subject will respond, or will likely respond, to the therapy,
thereby selecting the therapy.

15. A method of evaluating a subject having a melanoma, the method comprising:
(a) acquiring a value of responder status to a therapy comprising an inhibitor of PD-1 or PD-L1 for the subject, wherein said value of responder status comprises a measure of the tumor mutational burden (TMB) in a melanoma sample, or in a sample derived from the melanoma, from the subject, wherein the measure of the TMB comprises a determination of the number of one or more somatic alterations in a predetermined set of genes including ABL1, ABL2, ACVR1B, AKT1, AKT2, AKT3, ALK, AMER1, APC, AR, ARAF, ARFRP1, ARID1A, ARID1B, ARID2, ASXL1, ATM, ATR, ATRX, AURKA, AURKB, AXIN1, ALX, BAP1, BARD1, BCL2, BCL2L1, BCL2L2, BCL6, BCOR, BCORL1, BLM, BRAF, BRCA1, BRCA2, BRD4, BRIP1, BTG1, BTK, C11orf30, CARD11, CBFB, CBL, CCND1, CCND2, CCND3, CCNE1, CD274, CD79A, CD79B, CDC73, CDH1, CDK12, CDK4, CDK6, CDK8, CDKN1A, CDKN1B, CDKN2A, CDKN2B, CDKN2C, CEBPA, CHD2, CHD4, CHEK1, CHEK2, CIC, CREBBP, CRKL, CRLF2, CSF1R, CTCF, CTNNA1, CTNNB1, CUL3, CYLD, DAXX, DDR2, DICER1, DNMT3A, DOT1L, EGFR, EP300, EPHA3, EPHA5, EPHA7, EPHB1, ERBB2, ERBB3, ERBB4, ERG, ERRFI1, ESR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR1, FGFR2, FGFR3, FGFR4, FH, FLCN, FLT1, FLT3, FLT4, FOXL2, FOXP1, FRS2, FUBP1, GABRA6, GATA1, GATA2, GATA3, GATA4, GATA6, GID4, GLI1, GNA11, GNA13, GNAQ, GNAS, GPR124, GRIN2A, GRM3, GSK3B, H3F3A, HGF, HNF1A, HRAS, HSD3B1, HSP9OAA1, IDH1, IDH2, IGF1R, IGF2, IKBKE, IKZF1, IL7R, INHBA, IRF2, IRF4, IRS2, JAK1, JAK2, JAK3, JUN, KAT6A, KDM5A, KDM5C, KDM6A, KDR, KEAP1, KEL, KIT, KLHL6, KMT2A, KMT2C, KMT2D, KRAS, LMO1, LRP1B, LYN, LZTR1, MAGI2, MAP2K1, MAP2K2, MAP2K4, MAP3K1, MCL1, MDM2, MDM4, MED12, MEF2B, MEN1, MET, MITF, MLH1, MPL, MRE11A, MSH2, MSH6, MTOR, MUTYH, MYC, MYCL, MYCN, MYD88, NF1, NF2, NFE2L2, NFKB1A, NKX2-1, NOTCH1, NOTCH2, NOTCH3, NPM1, NRAS, NSD1, NTRK1, NTRK2, NTRK3, NUP93, PAK3, PALB2, PARK2, PAX5, PBRM1, PDCD1LG2, PDGFRA, PDGFRB, PDK1, PIK3C2B, PIK3CA, PIK3CB, PIK3CG, PIK3R1, PLCG2, PMS2, POLD1, POLE, PPP2R1A, PRDM1, PREX2, PRKAR1A, PRKCI, PRKDC, PRSS8, PTCH1, PTEN, PTPN11, QKI, RAC1, RAD50, RAD51, RAF1, RANBP2, RARA, RB1, RBM10, RET, RICTOR, RNF43, ROS1, RPTOR, RUNX1, RUNX1T1, SDHA, SDHB, SDHC, SDHD, SETD2, SF3B1, SLIT2, SMAD2, SMAD3, SMAD4, SMARCA4, SMARCB1, SMO, SNCAIP, SOCS1, SOX10, SOX2, SOX9, SPEN, SPOP, SPTA1, SRC, STAG2, STAT3, STAT4, STK11, SUFU, SYK, TAF1, TBX3, TERC, TERT (promoter only), TET2, TGFBR2, TNFAIP3, TNFRSF14, TOP1, TOP2A, TP53, TSC1, TSC2, TSHR, U2AF1, VEGFA, VHL, WISP3, WT1, XPO1, ZBTB2, ZNF217, or ZNF703; wherein the one or more somatic alterations do not comprise one or more of the following: a rearrangement, a translocation, a functional alteration, or a germline mutation, and wherein the one or more somatic alterations are detected in the sample by hybrid capture followed by sequencing; and (b) identifying the subject as a responder, a complete responder, a partial responder, or a non-responder to the therapy, wherein a value of responder status equal to or greater than a reference value of responder status indicates that: said subject is, or is likely to be, a responder to the therapy; or said subject will respond, or will likely respond, to the therapy; or wherein a value of responder status less than a reference value of responder status indicates that: said subject is, or is likely to be, a non-responder to the therapy; or said subject will not respond, or will likely not respond, to the therapy, thereby evaluating the subject.

16. A system for evaluating a subject having a melanoma, comprising:

at least one processor operatively connected to a memory, the at least one processor when executing is configured to:

(a) acquire a value of responder status to a therapy comprising an inhibitor of PD-1 or PD-L1 for the subject, wherein said value of responder status comprises a measure of the tumor mutational burden (TMB) in a melanoma sample, or a sample derived from the melanoma, from the subject, wherein the measure of the TMB comprises a determination of the number of one or more somatic alterations in a predetermined set of genes including ABL1, ABL2, ACVR1B, AKT1, AKT2, AKT3, ALK, AMER1, APC, AR, ARAF, ARFRP1, ARID1A, ARID1B, ARID2, ASXL1, ATM, ATR, ATRX, AURKA, AURKB, AXIN1, ALX, BAP1, BARD1, BCL2, BCL2L1, BCL2L2, BCL6, BCOR, BCORL1, BLM, BRAF, BRCA1, BRCA2, BRD4, BRIP1, BTG1, BTK, C11orf30, CARD11, CBFB, CBL, CCND1, CCND2, CCND3, CCNE1, CD274, CD79A, CD79B, CDC73, CDH1, CDK12, CDK4, CDK6, CDK8, CDKN1A, CDKN1B, CDKN2A, CDKN2B, CDKN2C, CEBPA, CHD2, CHD4, CHEK1, CHEK2, CIC, CREBBP, CRKL, CRLF2, CSF1R, CTCF, CTNNA1, CTNNB1, CUL3, CYLD, DAXX, DDR2, DICER1, DNMT3A, DOT1L, EGFR, EP300, EPHA3, EPHA5, EPHA7, EPHB1, ERBB2, ERBB3, ERBB4, ERG, ERRFI1, ESR1, EZH2, FAM46C, FANCA, FANCC, FANCD2, FANCE, FANCF, FANCG, FANCL, FAS, FAT1, FBXW7, FGF10, FGF14, FGF19, FGF23, FGF3, FGF4, FGF6, FGFR1, FGFR2, FGFR3, FGFR4, FH, FLCN, FLT1, FLT3, FLT4, FOXL2, FOXP1, FRS2, FUBP1, GABRA6, GATA1, GATA2, GATA3, GATA4, GATA6, GID4, GLI1, GNA11, GNA13, GNAQ, GNAS, GPR124, GRIN2A, GRM3, GSK3B, H3F3A, HGF, HNF1A, HRAS, HSD3B1, HSP9OAA1, IDH1, IDH2, IGF1R, IGF2, IKBKE, IKZF1, IL7R, INHBA, IRF2, IRF4, IRS2, JAK1, JAK2, JAK3, JUN, KAT6A, KDM5A, KDM5C, KDM6A, KDR, KEAP1, KEL, KIT, KLHL6, KMT2A, KMT2C, KMT2D, KRAS, LMO1, LRP1B, LYN, LZTR1, MAGI2, MAP2K1, MAP2K2, MAP2K4, MAP3K1, MCL1, MDM2, MDM4, MED12, MEF2B, MEN1, MET, MITF, MLH1, MPL, MRE11A, MSH2, MSH6, MTOR, MUTYH, MYC, MYCL, MYCN, MYD88, NF1, NF2, NFE2L2, NFKB1A, NKX2-1, NOTCH1, NOTCH2, NOTCH3, NPM1, NRAS, NSD1, NTRK1, NTRK2, NTRK3, NUP93, PAK3, PALB2, PARK2, PAX5, PBRM1, PDCD1LG2, PDGFRA, PDGFRB, PDK1, PIK3C2B, PIK3CA, PIK3CB, PIK3CG, PIK3R1, PLCG2, PMS2, POLD1, POLE, PPP2R1A, PRDM1, PREX2, PRKAR1A, PRKCI, PRKDC, PRSS8, PTCH1, PTEN, PTPN11, QKI, RAC1, RAD50, RAD51, RAF1, RANBP2, RARA, RB1, RBM10, RET, RICTOR, RNF43, ROS1, RPTOR, RUNX1, RUNX1T1, SDHA, SDHB, SDHC, SDHD, SETD2, SF3B1, SLIT2, SMAD2, SMAD3, SMAD4, SMARCA4, SMARCB1, SMO, SNCAIP, SOCS1, SOX10, SOX2, SOX9, SPEN, SPOP, SPTA1, SRC, STAG2, STAT3, STAT4, STK11, SUFU, SYK, TAF1, TBX3, TERC, TERT (promoter only), TET2, TGFBR2, TNFAIP3, TNFRSF14, TOP1, TOP2A, TP53, TSC1, TSC2, TSHR, U2AF1, VEGFA, VHL, WISP3, WT1, XPO1, ZBTB2, ZNF217, or ZNF703; wherein the one or more somatic alterations do not comprise one or more of the following: a rearrangement, a translocation, a functional alteration, or a germline mutation, and wherein the one or more somatic alterations are detected in the sample by hybrid capture followed by sequencing; and (b) identify the subject as a responder, a complete responder, a partial responder, or non-responder to the therapy,
  wherein a value of responder status equal to or greater than a reference value of responder status indicates that: said subject is, or is likely to be, a responder to the therapy; or said subject will respond, or will likely respond, to the therapy; or
  wherein a value of responder status less than a reference value of responder status indicates that: said subject is, or is likely to be, a non-responder to the therapy; or said subject will not respond, or will not likely respond, to the therapy,
thereby evaluating the subject.

\* \* \* \* \*